United States Patent [19]

Sprecker et al.

[11] Patent Number: 4,962,090

[45] Date of Patent: Oct. 9, 1990

[54] 2,4-DISUBSTITUTED AND 2,2,4-TRISUBSTITUTED TETRAHYDROPYRANYL-4-ETHERS, PROCESS FOR PREPARING SAME AND PERFUMERY USES THEREOF

[75] Inventors: Mark A. Sprecker, Sea Bright; Robert P. Belko, Woodbridge; Salvatore M. Brucato, Carteret; Charles E. J. Beck, Summit; Marie R. Hanna, Keyport, all of N.J.

[73] Assignee: International Flavors & Fragrances Inc., New York, N.Y.

[21] Appl. No.: 497,593

[22] Filed: Mar. 22, 1990

[51] Int. Cl.$^5$ ............................................... A61K 7/46
[52] U.S. Cl. .......................................... 512/9; 512/11; 549/416; 252/174.11; 252/108; 252/94
[58] Field of Search ................... 512/9, 12; 549/416; 252/174.11, 94, 108

[56] References Cited

U.S. PATENT DOCUMENTS

| | | | |
|---|---|---|---|
| 3,681,263 | 8/1972 | van der Linde et al. | 252/522 |
| 4,010,286 | 4/1977 | Hall et al. | 426/536 |
| 4,057,515 | 11/1977 | Boelens et al. | 512/1 |
| 4,070,491 | 1/1978 | Vinals et al. | 426/536 |
| 4,071,034 | 1/1978 | Vinals et al. | 131/17 R |
| 4,071,535 | 1/1978 | Vinals et al. | 260/345.1 |
| 4,115,406 | 9/1978 | Vinals et al. | 260/345.1 |
| 4,120,830 | 10/1978 | Renold et al. | 512/9 |
| 4,186,103 | 1/1980 | Hall et al. | 252/174.11 |
| 4,192,782 | 3/1980 | Hall et al. | 252/522 R |
| 4,240,447 | 12/1980 | Hall et al. | 131/9 |

FOREIGN PATENT DOCUMENTS

| | | | |
|---|---|---|---|
| 618374 | 8/1978 | U.S.S.R. | 512/1 |
| 620487 | 8/1978 | U.S.S.R. | 512/1 |
| 638597 | 12/1978 | U.S.S.R. | 512/1 |

OTHER PUBLICATIONS

Abstract of Dutch Patent Application 68,08496 (12/19/69) Chemische Fabriek Naarden.

Primary Examiner—James H. Reamer
Attorney, Agent, or Firm—Arthur L. Liberman

[57] ABSTRACT

Described are 2,4-disubstituted and 2,2,4-trisubstituted tetrahydropyranyl-4-ethers defined according to the generic structure:

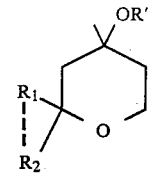

wherein R' represents methyl or ethyl; $R_1$ and $R_2$ taken alone are the same or different hydrogen, phenyl, $C_1$–$C_8$ alkyl or $C_2$–$C_8$ alkenyl (with the proviso that $R_1$ and $R_2$ are not both hydrogen) and $R_1$ and $R_2$ taken together represent $C_5$–$C_{12}$ cycloalkyl or alkyl cycloalkyl, and reaction products containing said 2,4-disubstituted and 2,2,4-trisubstituted tetrahydropyranyl-4-ethers taken alone or taken further together in admixture with compounds defined according to the generic structure:

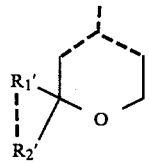

wherein in the compounds defined according to the structure:

(Abstract continued on next page.)

one of the dashed lines in the moiety:

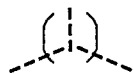

represents a carbon-carbon double bond and each of the other dashed lines represent carbon-carbon single bonds; and $R_1'$ and $R_2'$ taken alone or taken together are defined in the same manner that $R_1$ and $R_2$ are defined, supra; and organoleptic uses thereof in augmenting or enhancing the aroma of perfume compositions, colognes and perfumed articles including but not limited to bleach compositions, solid or liquid anionic, cationic, nonionic or zwitterionic detergents, perfume polymers, fabric softener compositions, fabric softener articles, cosmetic powders and hair preparations.

50 Claims, 47 Drawing Sheets

GLC PROFILE FOR EXAMPLE I.

FIG. 2 NMR SPECTRUM FOR EXAMPLE I, FRACTION II

GLC PROFILE FOR EXAMPLE II.

NMR SPECTRUM FOR EXAMPLE II, PEAKS 31 AND 32 OF FIG. 3

GLC PROFILE FOR EXAMPLE III.

FIG. 6 NMR SPECTRUM FOR EXAMPLE III, FRACTION 14

NMR SPECTRUM FOR EX. III, FRACTION II.

FIG. 9 NMR SPECTRUM FOR EXAMPLE IV, PEAKS 81 & 82 OF FIG. 8.

GLC PROFILE FOR EXAMPLE V.

NMR SPECTRUM FOR EXAMPLE V, PEAK 103 OF FIG. 10.

GLC PROFILE FOR EXAMPLE VI.

NMR SPECTRUM FOR EXAMPLE VI, FRACTION 14.

GLC PROFILE FOR EXAMPLE VII.

FIG. 15 NMR SPECTRUM FOR EXAMPLE VII, PEAKS 140 & 141 OF FIG. 14.

GLC PROFILE FOR EXAMPLE VIII.

FIG. 17 NMR SPECTRUM FOR EXAMPLE VIII, PEAKS 160 & 161 OF FIG. 16.

GLC PROFILE FOR EXAMPLE IX.

FIG. 19 NMR SPECTRUM FOR EXAMPLE IX, PEAKS 180 & 181 OF FIG. 18

GLC PROFILE FOR EXAMPLE X.

NMR SPECTRUM FOR EXAMPLE X FRACTION 14.

GLC PROFILE FOR EXAMPLE XI.

FIG. 23 NMR SPECTRUM FOR EXAMPLE XI, PEAKS 2202, 2203 & 2204 OF FIG. 22.

NMR SPECTRUM FOR EXAMPLE XI, PEAKS 2201 & 2200 OF FIG. 22.

GLC PROFILE FOR EXAMPLE XII.

FIG. 26  NMR SPECTRUM FOR EXAMPLE XII, PEAKS 2500 & 2501 OF FIG. 25.

GLC PROFILE FOR EXAMPLE XIII

NMR SPECTRUM FOR EXAMPLE XIII
PEAKS 2700 & 2701 OF FIG. 27.

GLC PROFILE FOR EXAMPLE XIV.

FIG. 30 — NMR SPECTRUM FOR EXAMPLE XIV, FRACTION 9

GLC PROFILE FOR EXAMPLE XV.

FIG. 32  NMR SPECTRUM FOR EXAMPLE XV, PEAKS 312, 313 & 314 OF FIG. 31.

NMR SPECTRUM FOR EXAMPLE XV, PEAKS 310 & 311 OF FIG. 31.

GLC PROFILE FOR EXAMPLE XVI.

FIG. 35 NMR SPECTRUM FOR EXAMPLE XVI, PEAKS 340 & 341 OF FIG. 34.

NMR SPECTRUM FOR EXAMPLE XVI PEAKS 342 & 343 OF 1

GLC PROFILE FOR EXAMPLE XVII.

FIG. 39 NMR SPECTRUM FOR EXAMPLE XVII, FRACTION 5

GLC PROFILE FOR EXAMPLE XVIII.

NMR SPECTRUM FOR EXAMPLE XVIII
PEAKS 400 & 401 OF FIG. 40.

FIG. 42 NMR SPECTRUM FOR EXAMPLE XVIII, PEAKS 402, 403 & 404 OF FIG. 40.

GLC PROFILE FOR EXAMPLE XIX.

NMR SPECTRUM FOR EXAMPLE XIX PEAK 430 OF FIG. 43.

GLC PROFILE FOR EXAMPLE XX.

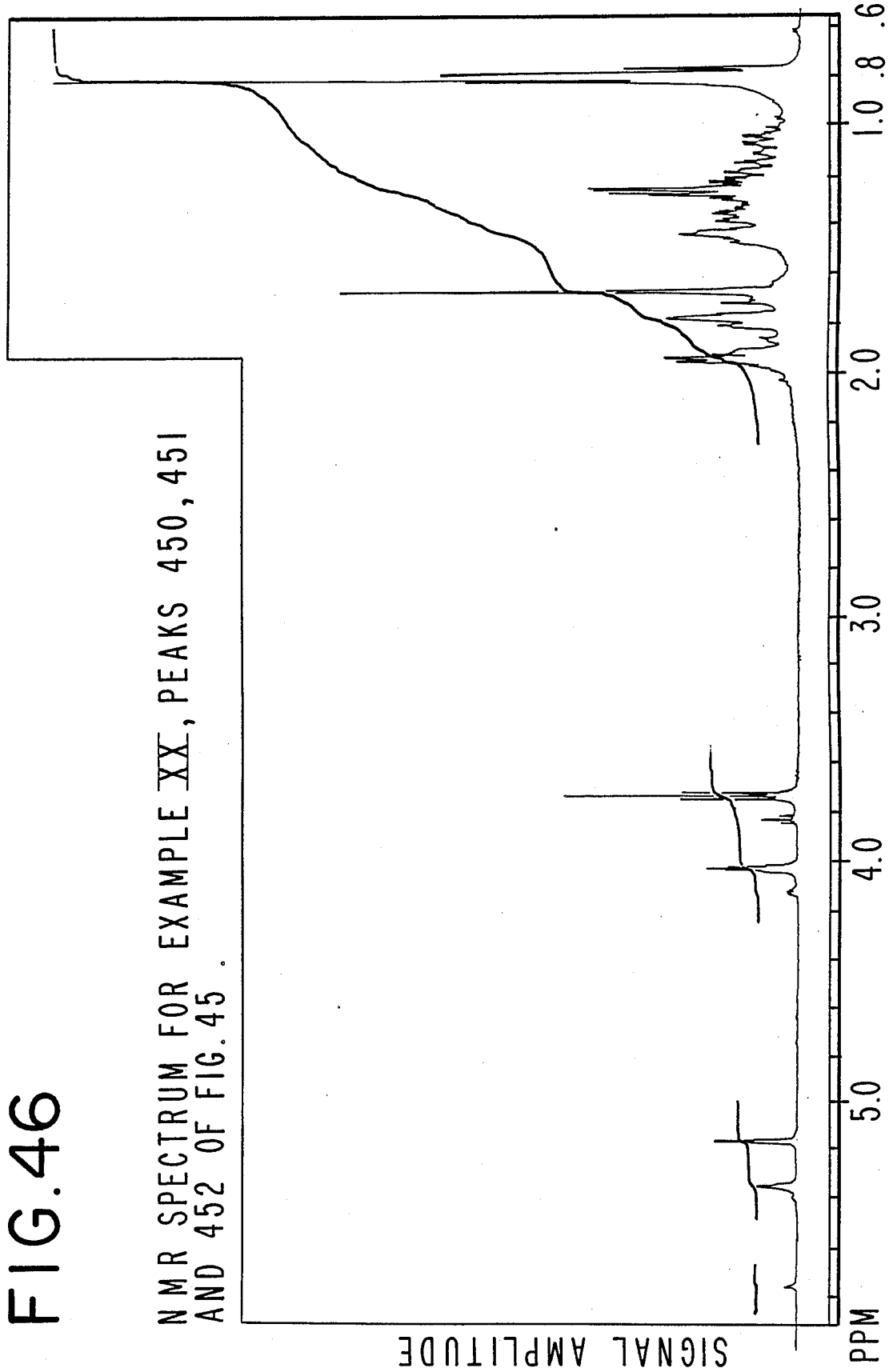
FIG. 46 NMR SPECTRUM FOR EXAMPLE XX, PEAKS 450, 451 AND 452 OF FIG. 45.

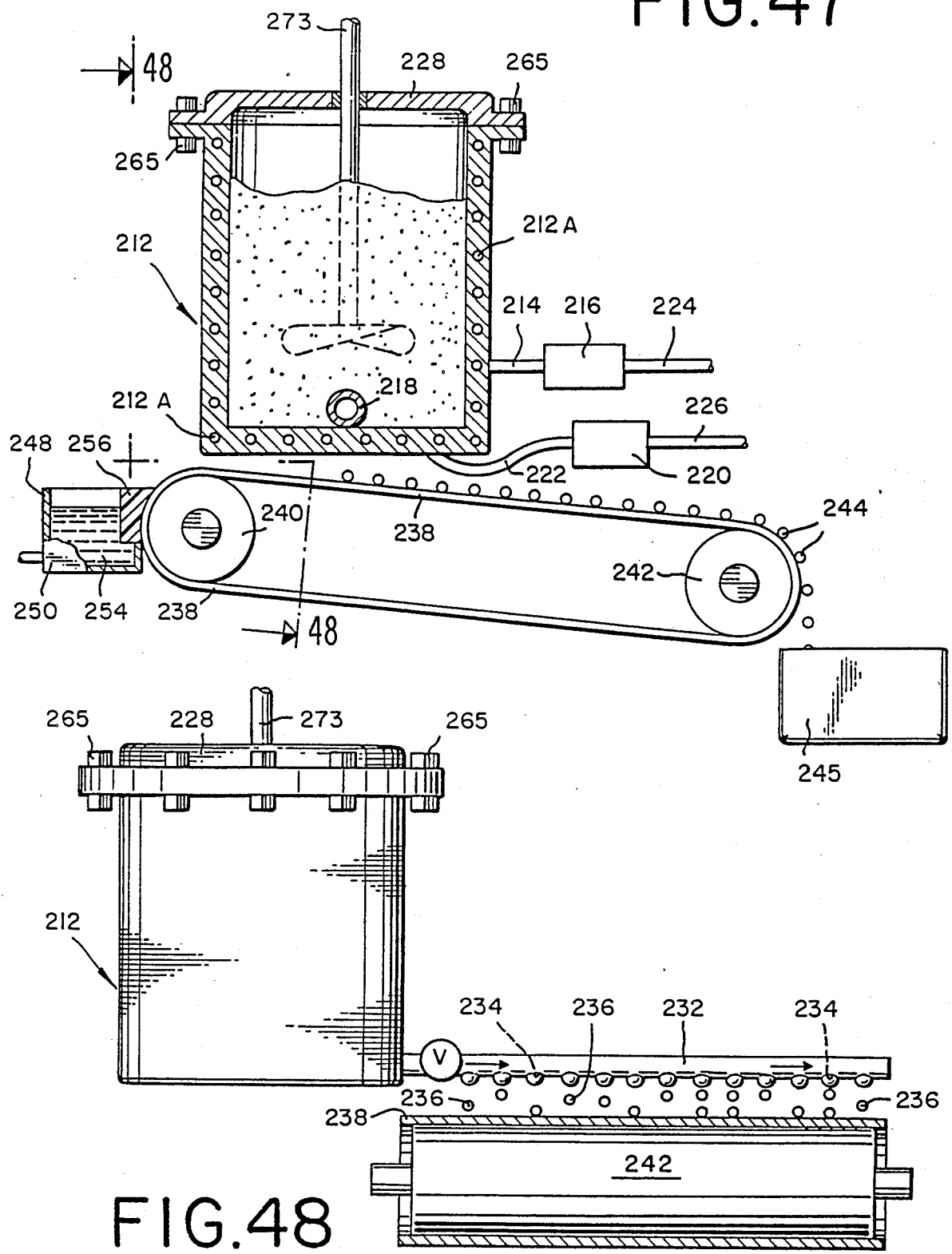

2,4-DISUBSTITUTED AND 2,2,4-TRISUBSTITUTED TETRAHYDROPYRANYL-4-ETHERS, PROCESS FOR PREPARING SAME AND PERFUMERY USES THEREOF

BACKGROUND OF THE INVENTION

The present invention relates to 2,4-disubstituted and 2,2,4-trisubstituted tetrahydropyranyl-4-ethers defined according to the structure:

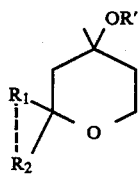

wherein R' represents methyl or ethyl and wherein $R_1$ and $R_2$ taken alone are the same or different hydrogen, phenyl, $C_1$–$C_8$ alkyl or $C_2$–$C_8$ alkenyl (with the proviso that $R_1$ and $R_2$ are not both hydrogen) and $R_1$ and $R_2$ taken together represent $C_5$–$C_{12}$ cycloalkyl or alkyl cycloalkyl, and reaction products containing same as well as uses thereof in order to alter, modify or enhance the aroma of consumable materials.

There has been considerable work performed relating to substances which can be used to impart (alter, modify or enhance) fragrances to (or in) various consumable materials. These substances are used to diminish the use of natural materials some of which may be in short supply and to provide more uniform properties in the finished product.

Green, herbaceous, basil, parsley, rose, fruity, mandarin orange peel, spicy, earthy, rooty, sauge sclaree, minty, woody, celery-like, citrusy, seashore, fresh, clean, ozoney, tangerine-like, grapefruit-like, Nootkatone-like, jasmine, dill, caraway, nutty, coconut, floral, peach-like, apricot-like, caramel-like, maple syrup and new mown hay aromas, with galbanum, jasmine, celery-like, green, pineapple, cinnamon, pineapple, oak moss, almond oil, animalic, herbaceous, camphoraceous and eucalyptus-like topnotes, and fruity, floral, jasmine, lily of the valley, green, herbaceous, animalic, dill, caraway, citrusy, sweet citrus, straw-like and bergamot undertones are highly desirable in several types of perfume compositions, perfumed articles and colognes.

The perfume use of 2,4-disubstituted tetrahydropyranols having the structures:

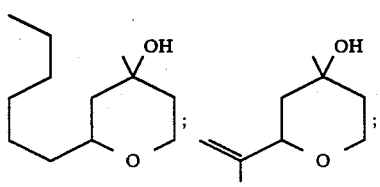

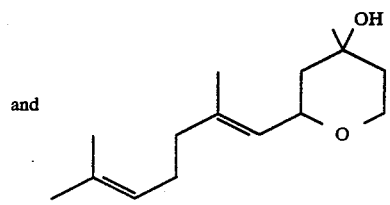

is disclosed in the literature as follows:

(a) the perfume use of the compound having the structure:

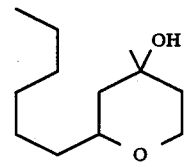

USSR Patent 620487 of July 17, 1978 (Chemical Abstracts 89: 185929p);

(b) the compound having the structure:

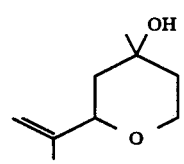

USSR Patent 638597 of Dec. 28, 1978 (Chemical Abstracts, Volume 90: 109812a);

(c) the compound having the structure:

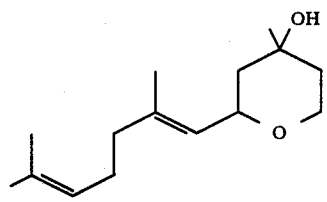

USSR Patent 618374 of Aug. 5, 1978 (Chemical Abstracts 89: 179861u).

The perfumery uses of compounds defined according to the generic structure:

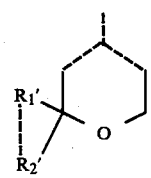

wherein $R_1'$ and $R_2'$ are defined, supra, including compounds of the subgenuses:

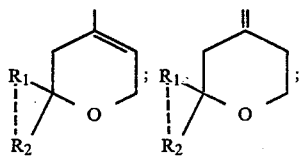 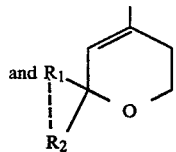

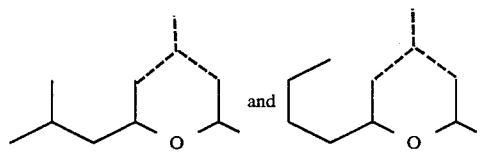

is well known in the prior art. Thus, for example, U.S. Letters Patent 3,681,263 (Van der Linde, et al) discloses the use of the compounds having the structures:

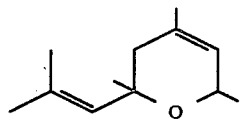

in perfumery (mixtures wherein in the mixtures in each of the compounds one of the dashed lines is a carbon-carbon double bond and each of the other of the dashed lines represent carbon-carbon single bonds) using as an intermediate to form such compounds the compound having the structure:

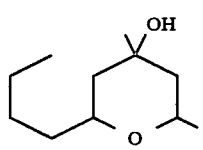

Van der Linde, et al also discloses the perfumery use of the compound having the structure:

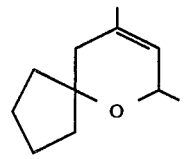

and the synthesis process, to wit:

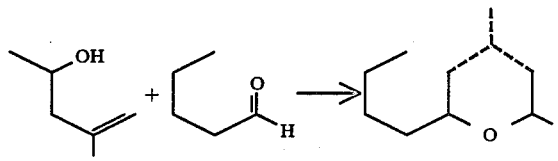

Hall, et al, U.S. Letters Patent 4,240,447 discloses the genus of compounds defined according to the structure:

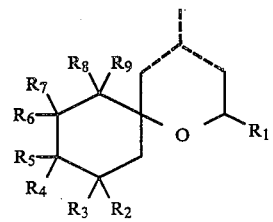

for use in perfumery wherein the moieties $R_1$, $R_2$, $R_3$, $R_4$, $R_5$, $R_6$, $R_7$, $R_8$ and $R_9$ may be hydrogen or alkyl and one of the dashed lines is a carbon-carbon double bond and each of the other of the dashed lines are carbon-carbon single bonds in each of the compounds disclosed.

Netherlands Published Patent Application 68/08496 discloses the genus of compounds defined according to the structure:

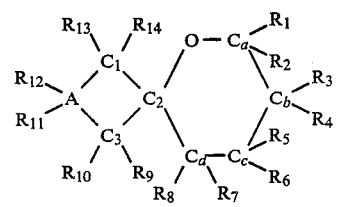

wherein A completes a cycloalkyl moiety and the moieties $R_1$, $R_2$, $R_3$, $R_4$, $R_5$, $R_6$, $R_7$, $R_8$, $R_9$, $R_{10}$, $R_{11}$, $R_{12}$, $R_{13}$ and $R_{14}$ represent hydrogen or alkyl . . . including the compound having the structure:

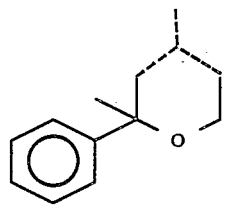

(formula 15).

Vinals, et al, U.S. Letters Patent 4,070,491, at columns 15 and 16, discloses the organoleptic uses of the compound having the structure:

wherein one of the dashed lines is a carbon-carbon double bond and each of the other of the dashed lines represent carbon-carbon single bonds.

Nothing in the prior art discloses the 2,4-disubstituted and 2,2,4-trisubstituted tetrahydropyranyl-4-ethers of our invention for their organoleptic utilities.

In addition, the prior art discloses synthetic routes to the genus of compounds having the structure:

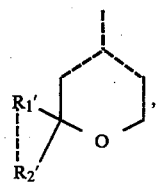

to wit: Chem. Abstracts Volume 101: 54857g disclosing the genus of compounds having the structure:

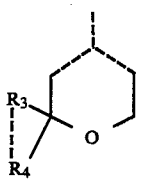

wherein $R_3$ and $R_4$ represent alkyl, hydrogen, phenyl, vinyl, cyclohexyl and cyclopentyl; Chem. Abstracts Volume 87: 5757h disclosing the synthesis route:

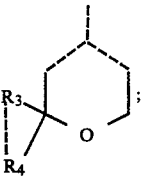

Chem. Abstracts Volume 101: 54857 disclosing the synthesis route:

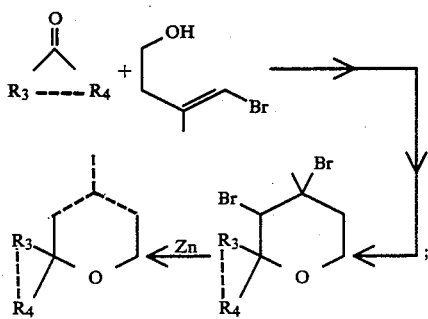

Chem. Abstracts Volume 94: 47139h disclosing the synthesis route:

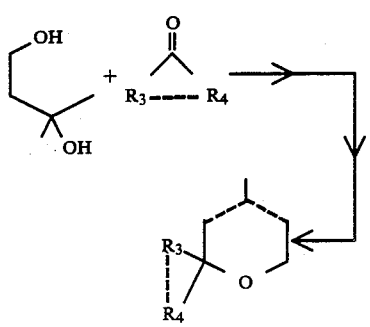

Nothing in the prior art shows synthesis routes which will effect production of the 2,4-disubstituted and 2,2,4-trisubstituted tetrahydropyranyl-4-ethers of our invention.

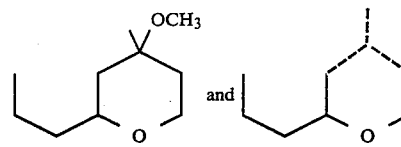

wherein the compounds having the structure:

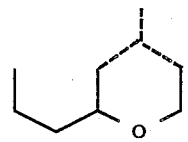

one of the dashed lines is a carbon-carbon double bond and each of the other of the dashed lines represent carbon-carbon single bonds (Conditions: SE-30 column programmed at 180° C. isothermal).

Figure 2:
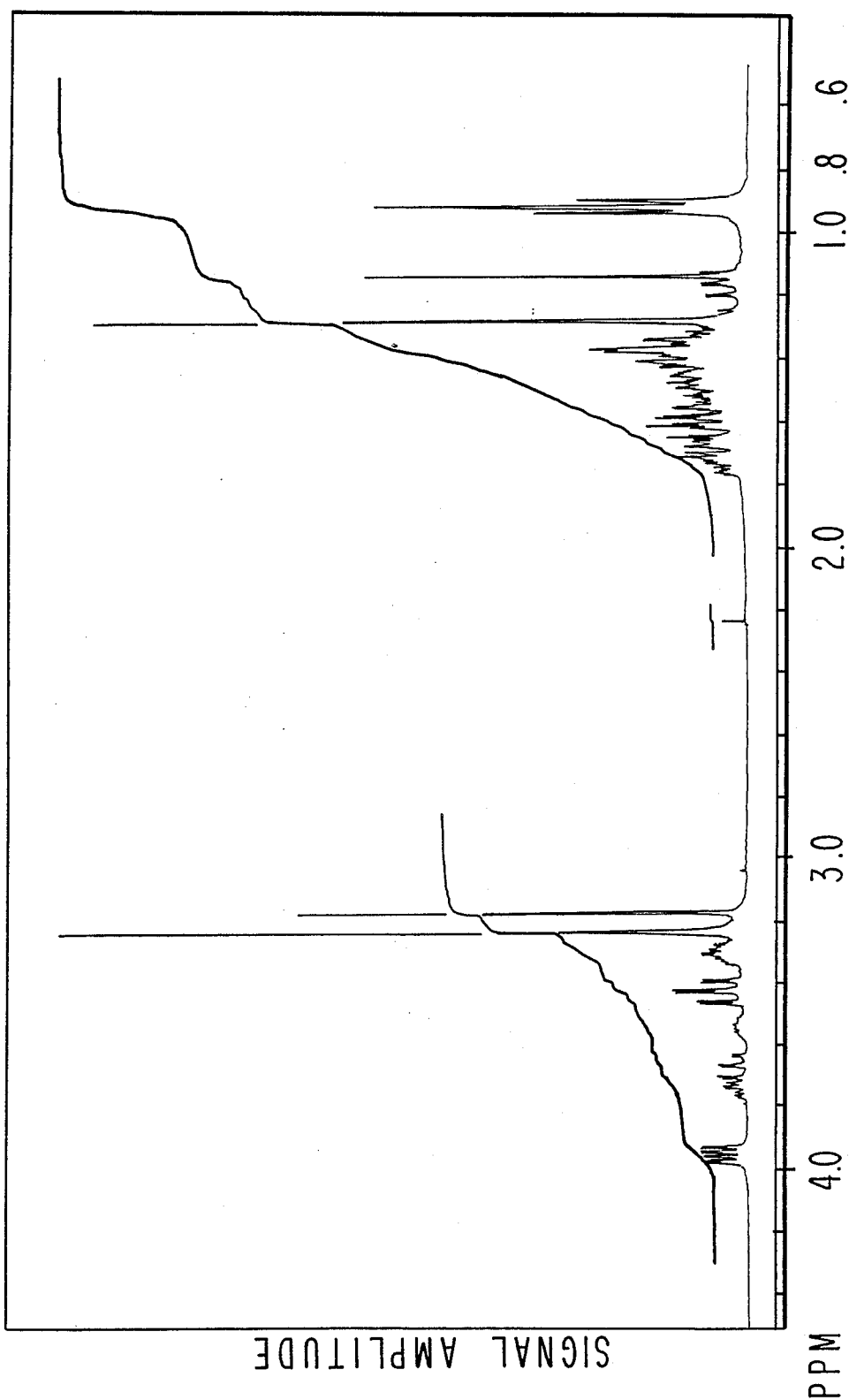

FIG. 2 is the NMR spectrum for the compound having the structure:

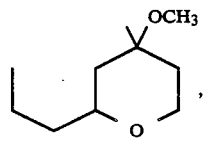

fraction 11 of the distillation product of the reaction product of Example I.

Figure 3:
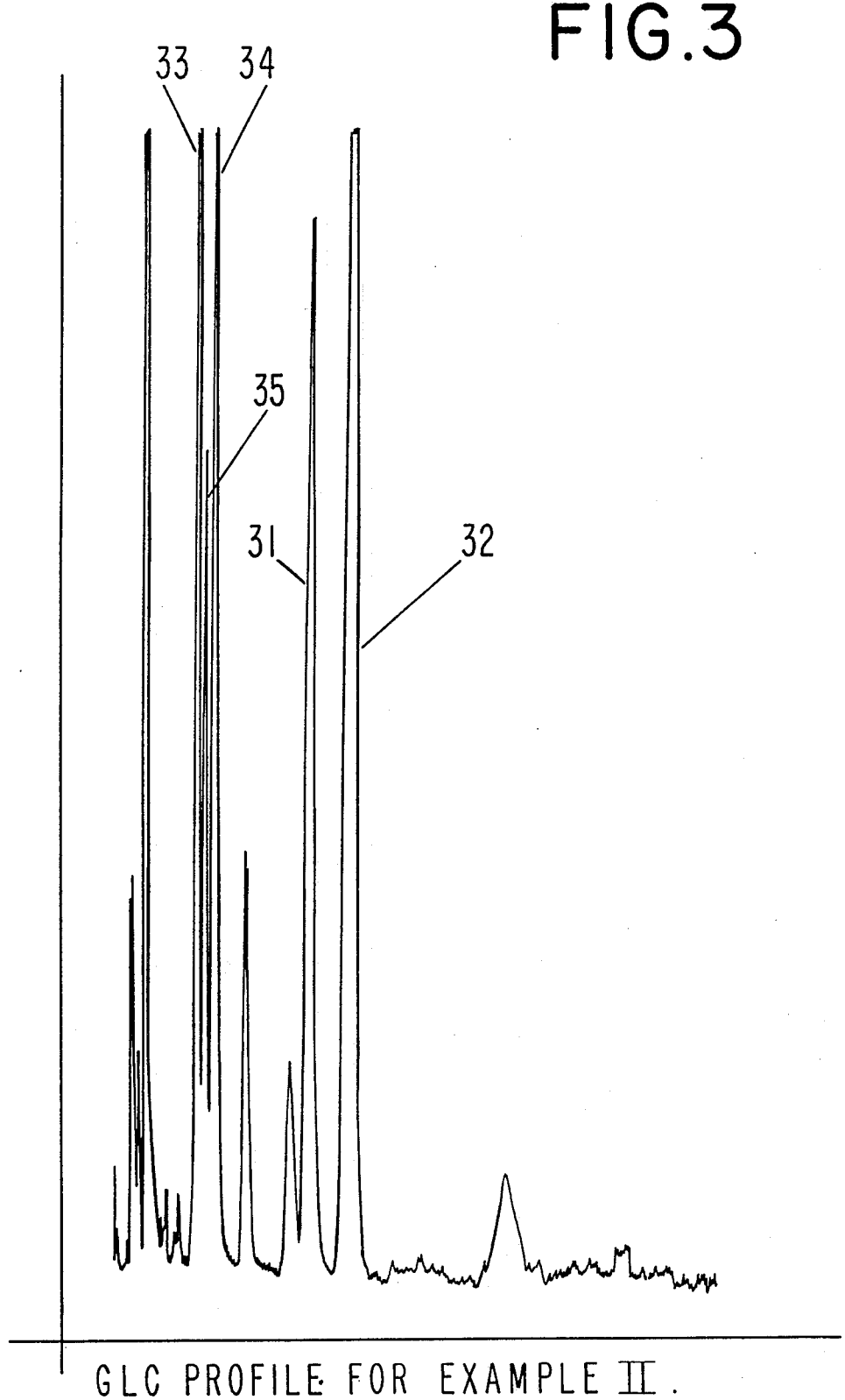

FIG. 3 is the GLC profile for the reaction product of Example II containing the compounds having the structures:

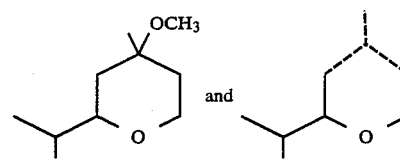

wherein in the compounds having the structure:

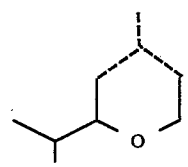

one of the dashed lines is a carbon-carbon double bond and each of the other of the dashed lines are carbon-carbon single bonds (Conditions: SE-30 column programmed at 180° C. isothermal).

Figure 4:
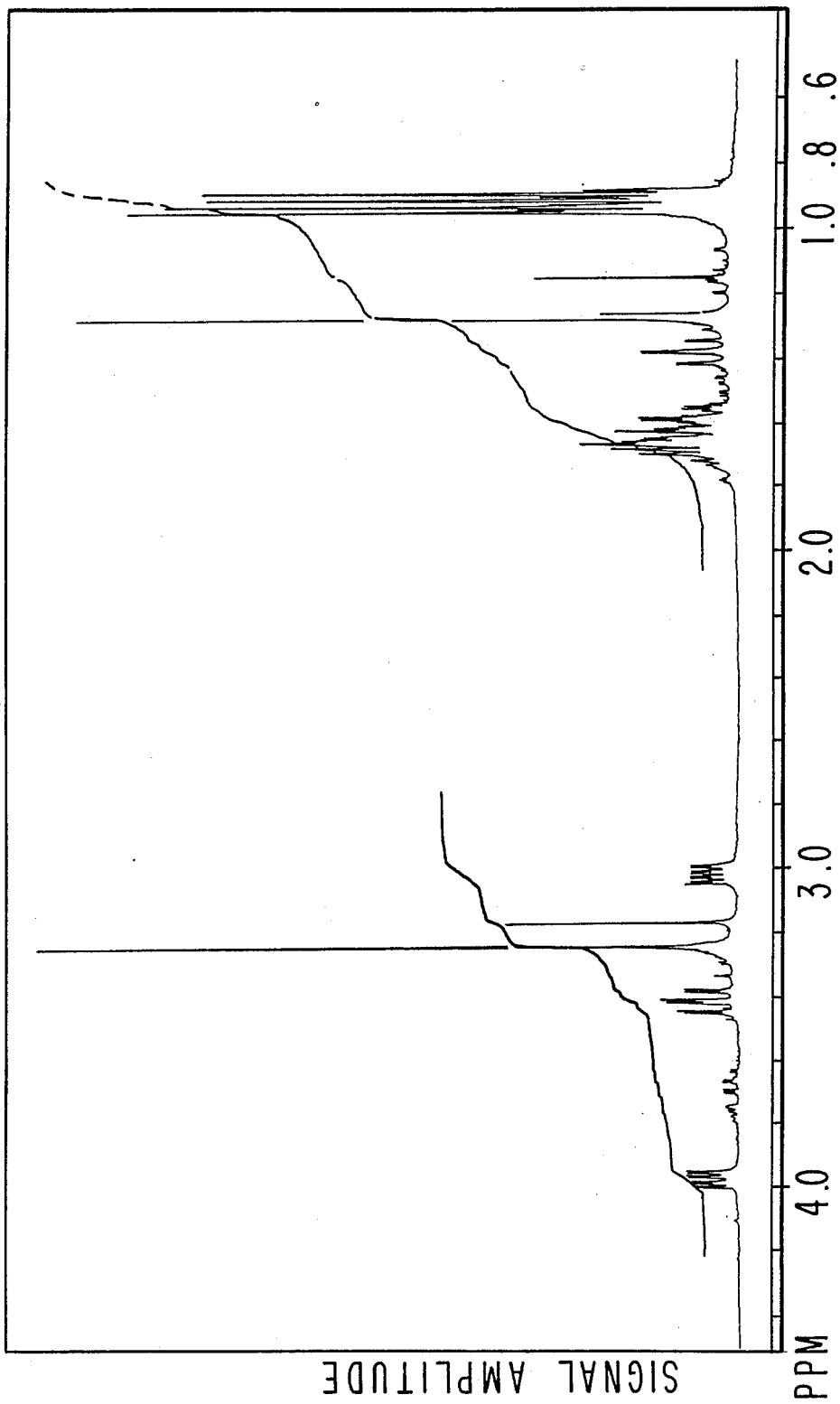

FIG. 4 is the NMR spectrum for the peaks indicated by reference numerals 31 and 32 of the GLC profile of FIG. 3; for the compound having the structure:

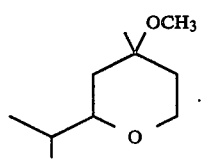

Figure 5:
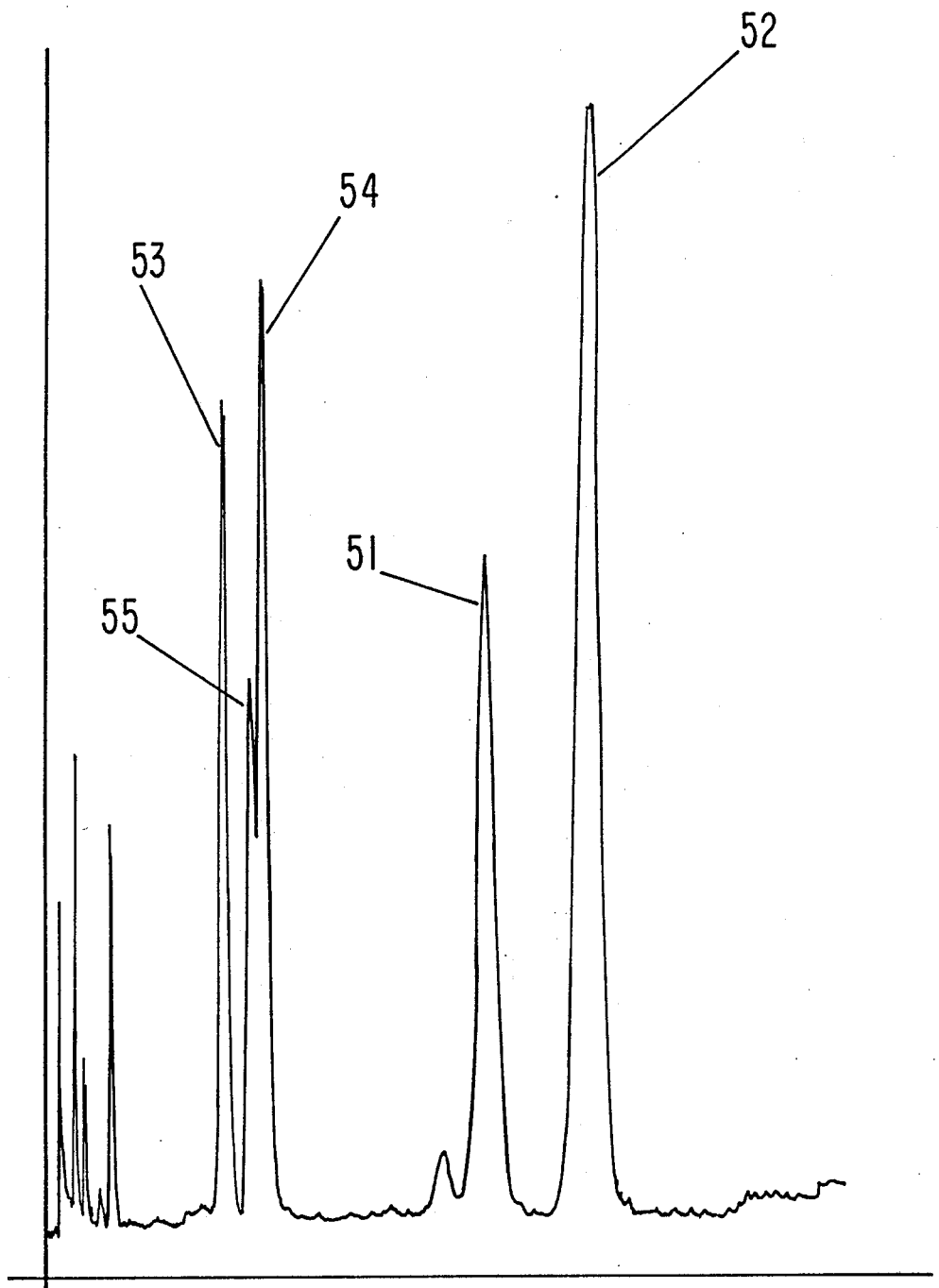

FIG. 5 is the GLC profile for the reaction product of Example III containing the compounds having the structures:

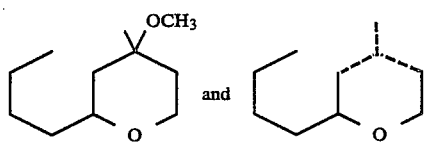

wherein in the compounds having the structure:

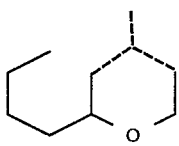

one of the dashed lines is a carbon-carbon double bond and each of the other of the dashed lines represent carbon-carbon single bonds (Conditions: SE-30 column programmed at 120° C. isothermal).

Figure 6:
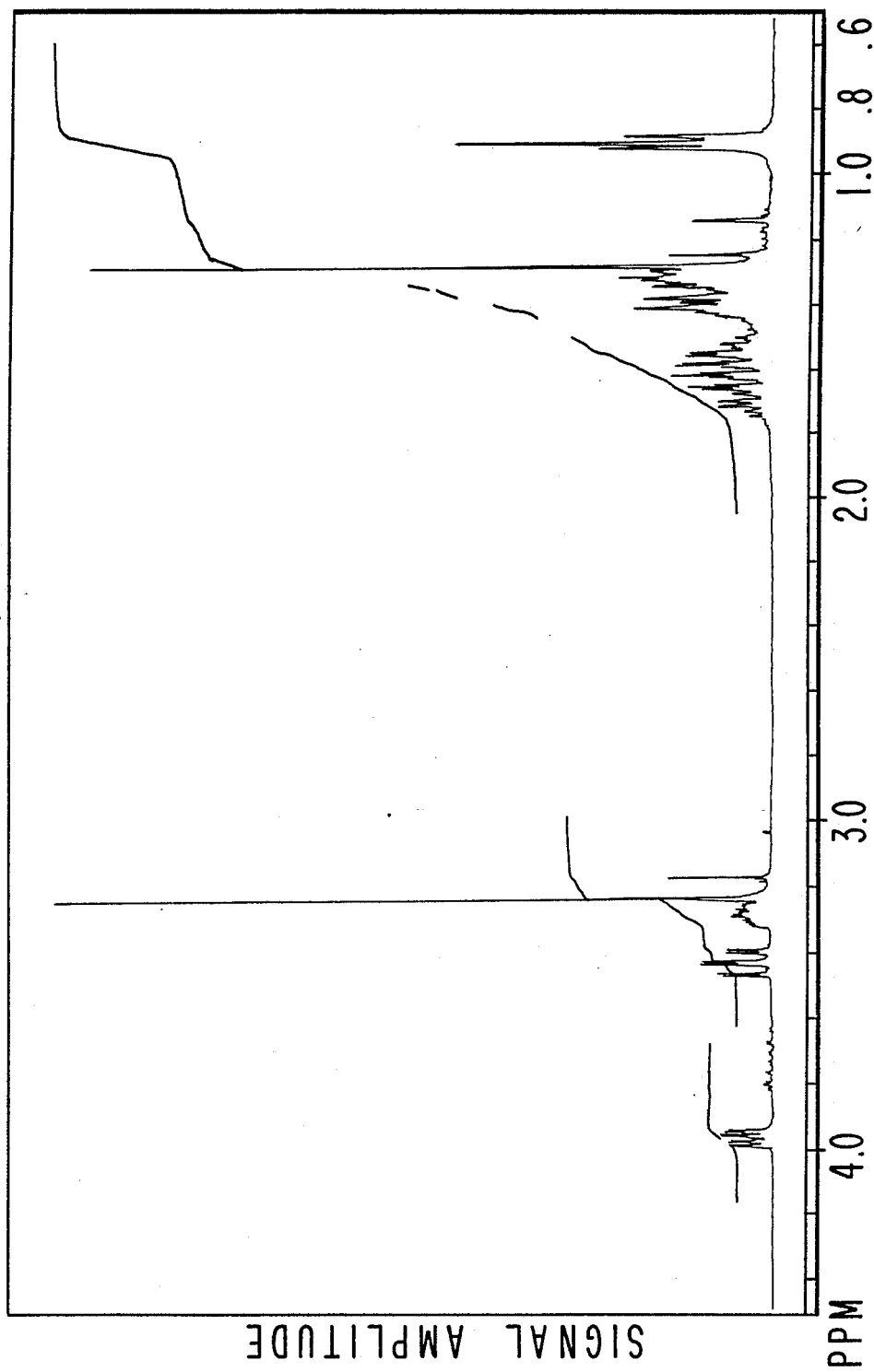

FIG. 6 is the NMR spectrum for Fraction 14 of the distillation product of the reaction product of Example III which is for the compound having the structure:

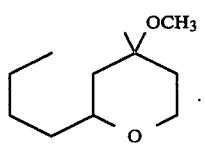

Figure 7:
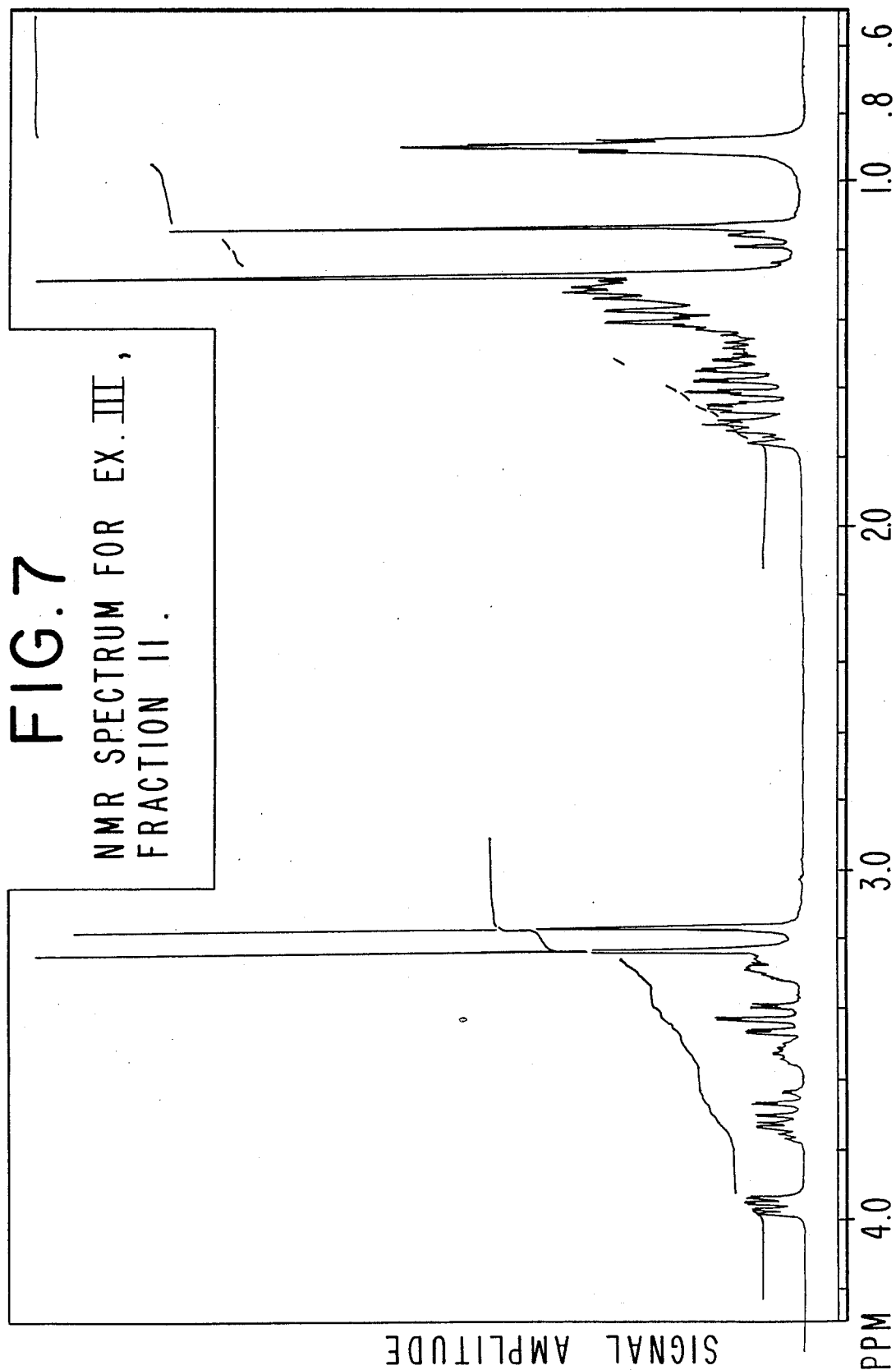

FIG. 7 is the NMR spectrum for Fraction 11 of the distillation product of the reaction product of Example III which is for the compound having the structure:

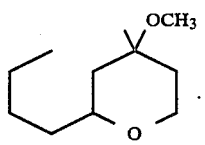

Figure 8:
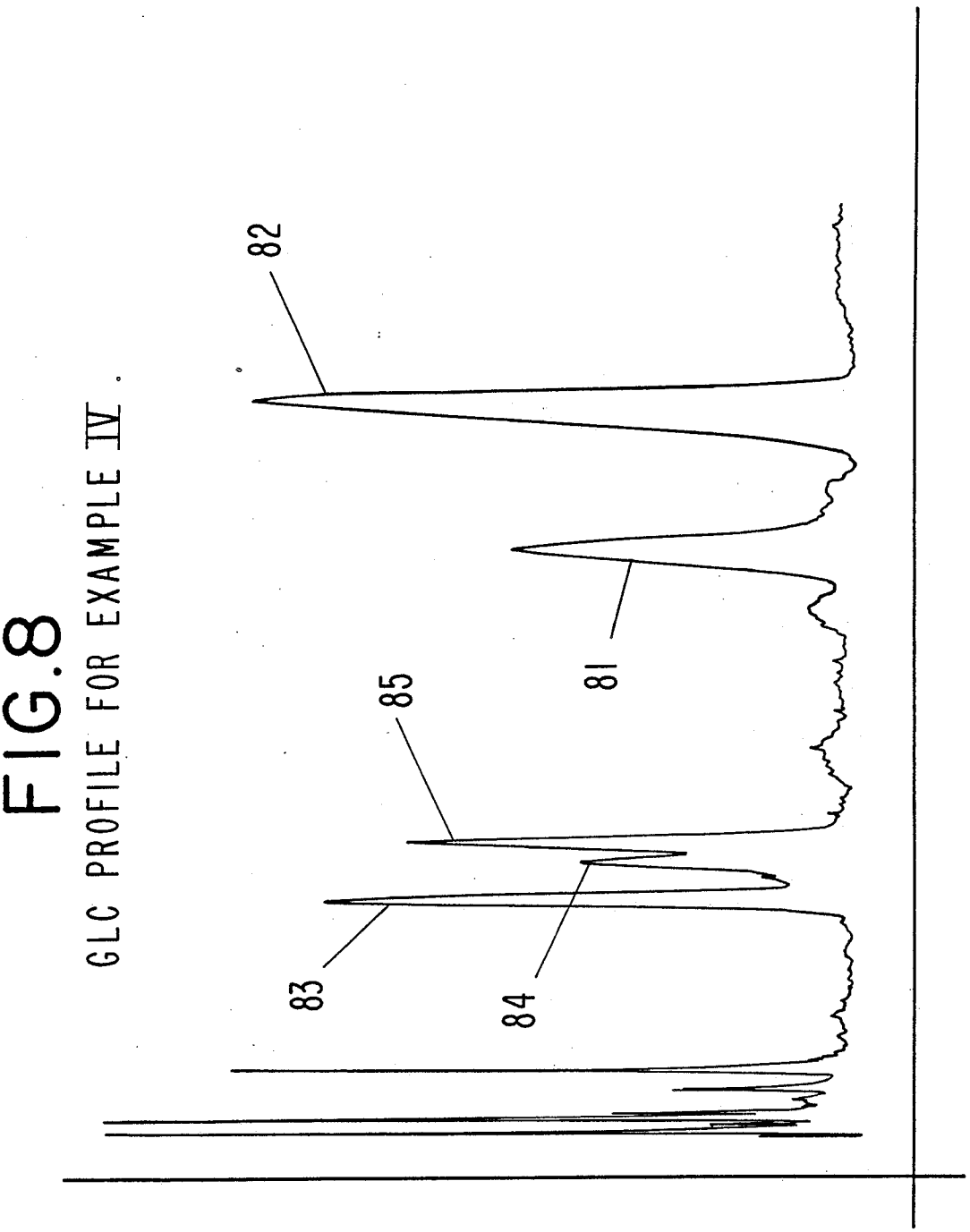

FIG. 8 is the GLC profile for the reaction product of Example IV containing the compounds having the structures:

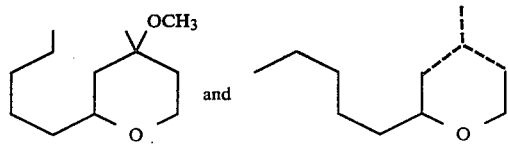

wherein in the compounds having the structure:

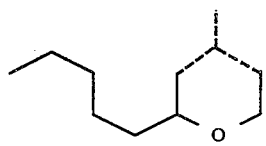

one of the dashed lines is a carbon-carbon double bond and each of the other of the dashed lines represent carbon-carbon single bonds (Conditions: SE-30 column programmed at 120° C. isothermal).

Figure 9:
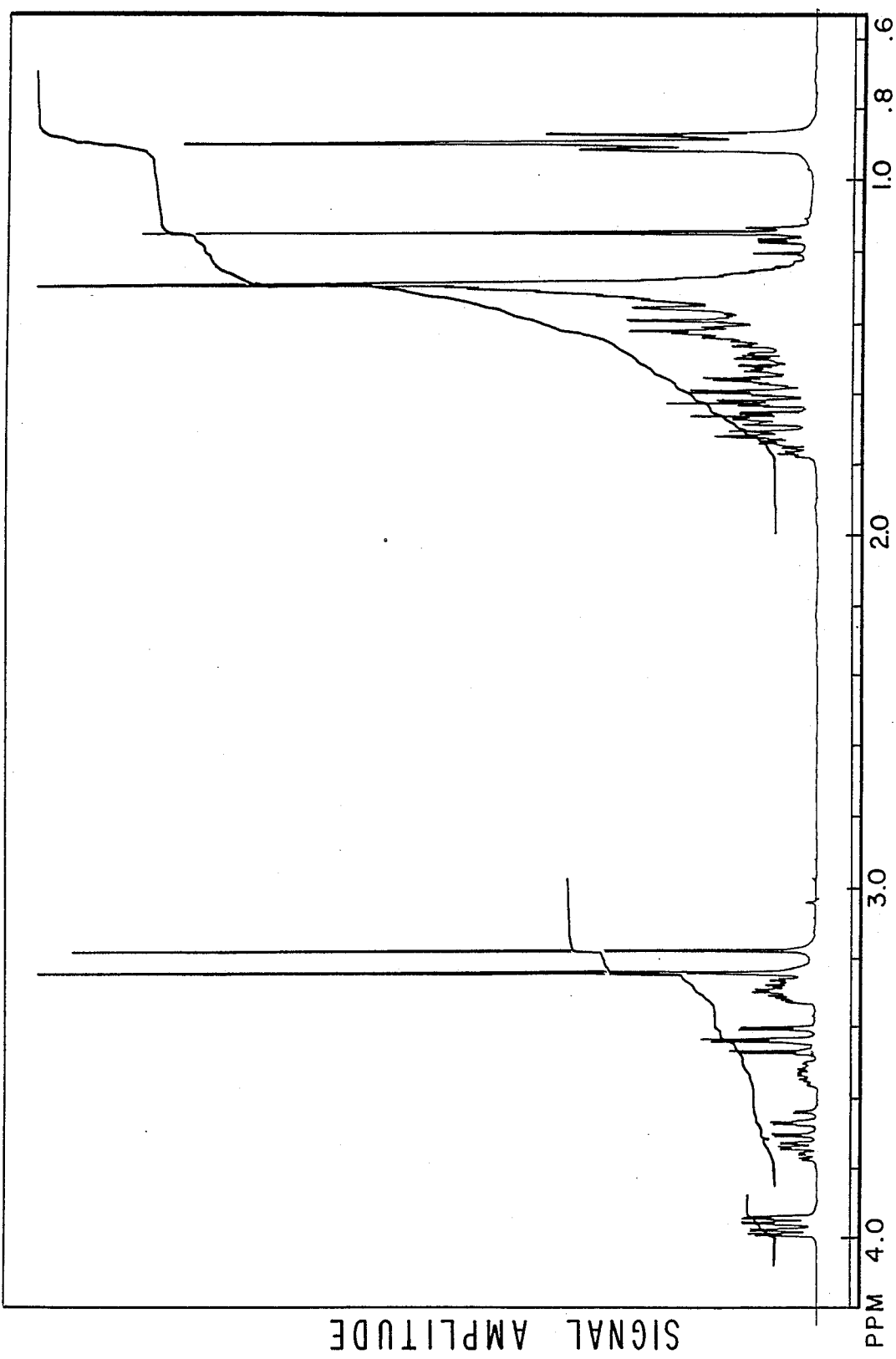

FIG. 9 is the NMR spectrum for the peaks indicated by reference numerals 81 and 82 of the GLC profile of FIG. 8 for the compound having the structure:

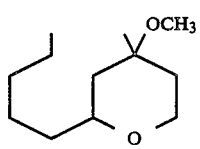

Figure 10:
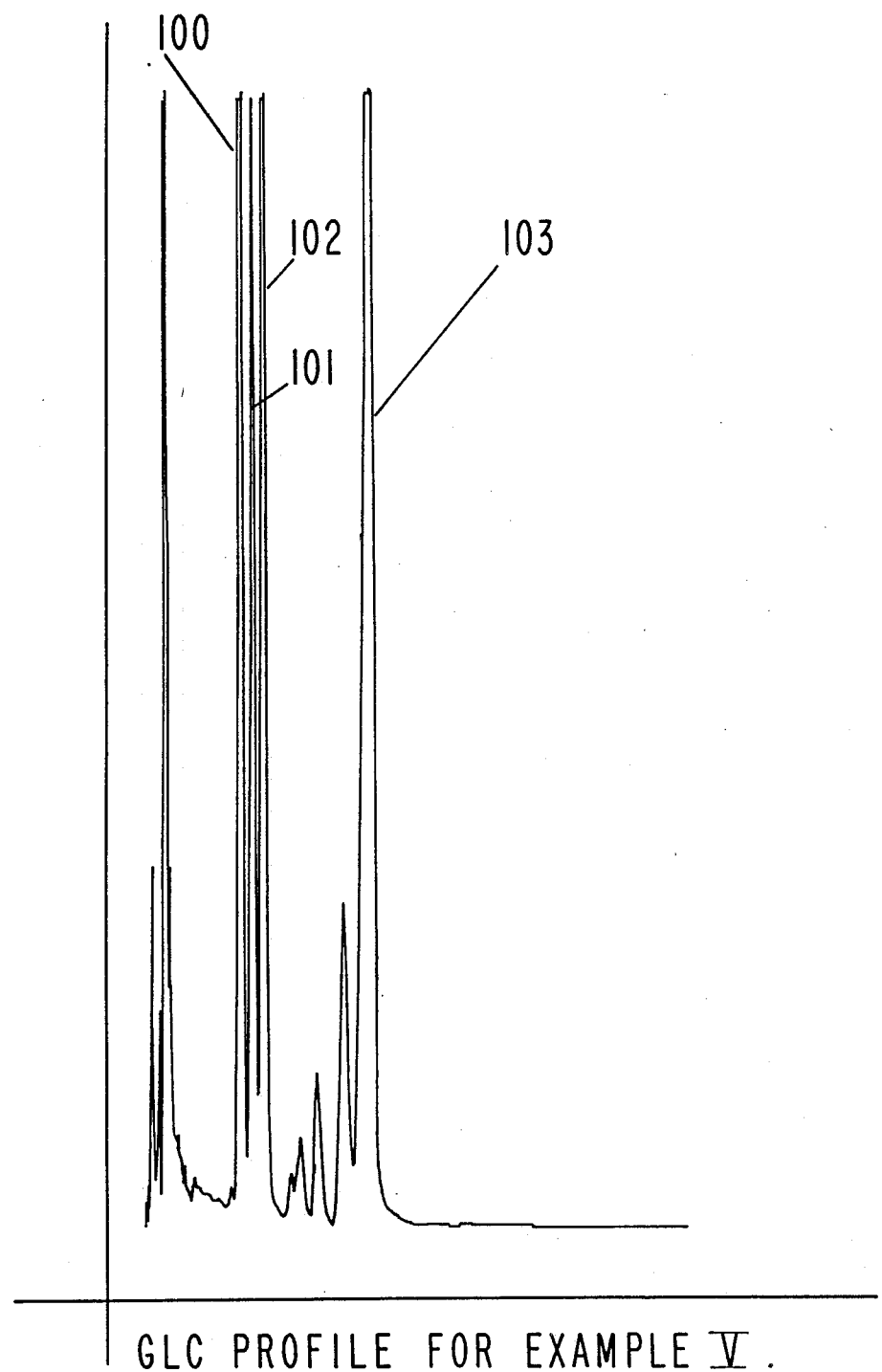

FIG. 10 is the GLC profile for the reaction product of Example V containing the compounds having the structures:

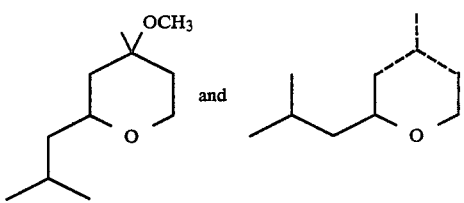

wherein in the compounds having the structure:

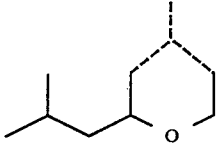

one of the dashed lines represents a carbon-carbon double bond and each of the other of the dashed lines represent carbon-carbon single bonds.

Figure 11:
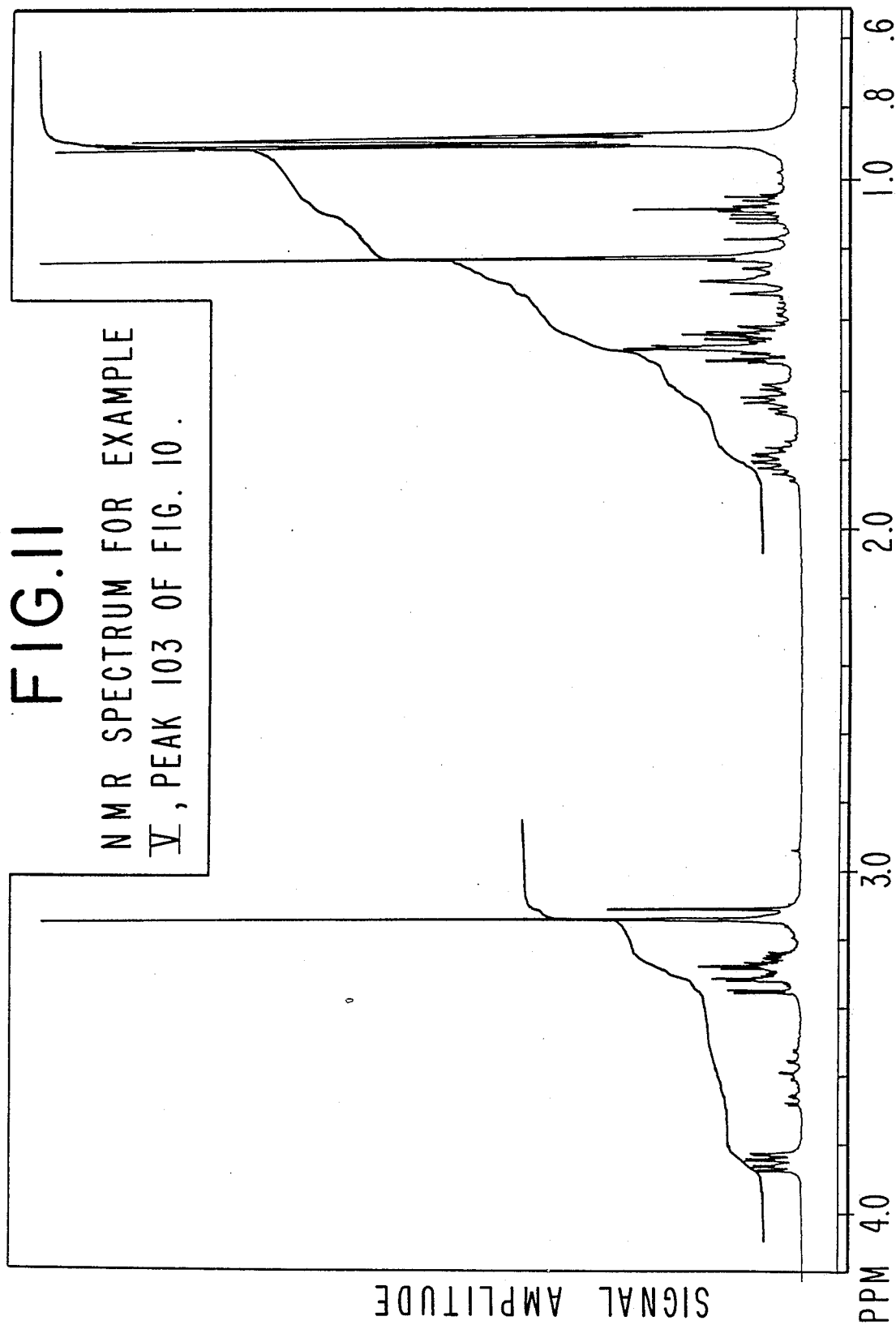

FIG. 11 is the NMR spectrum for peak 103 of the GLC profile of FIG. 10 for the compound having the structure:

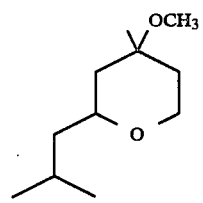

prepared according to Example V.

Figure 12:
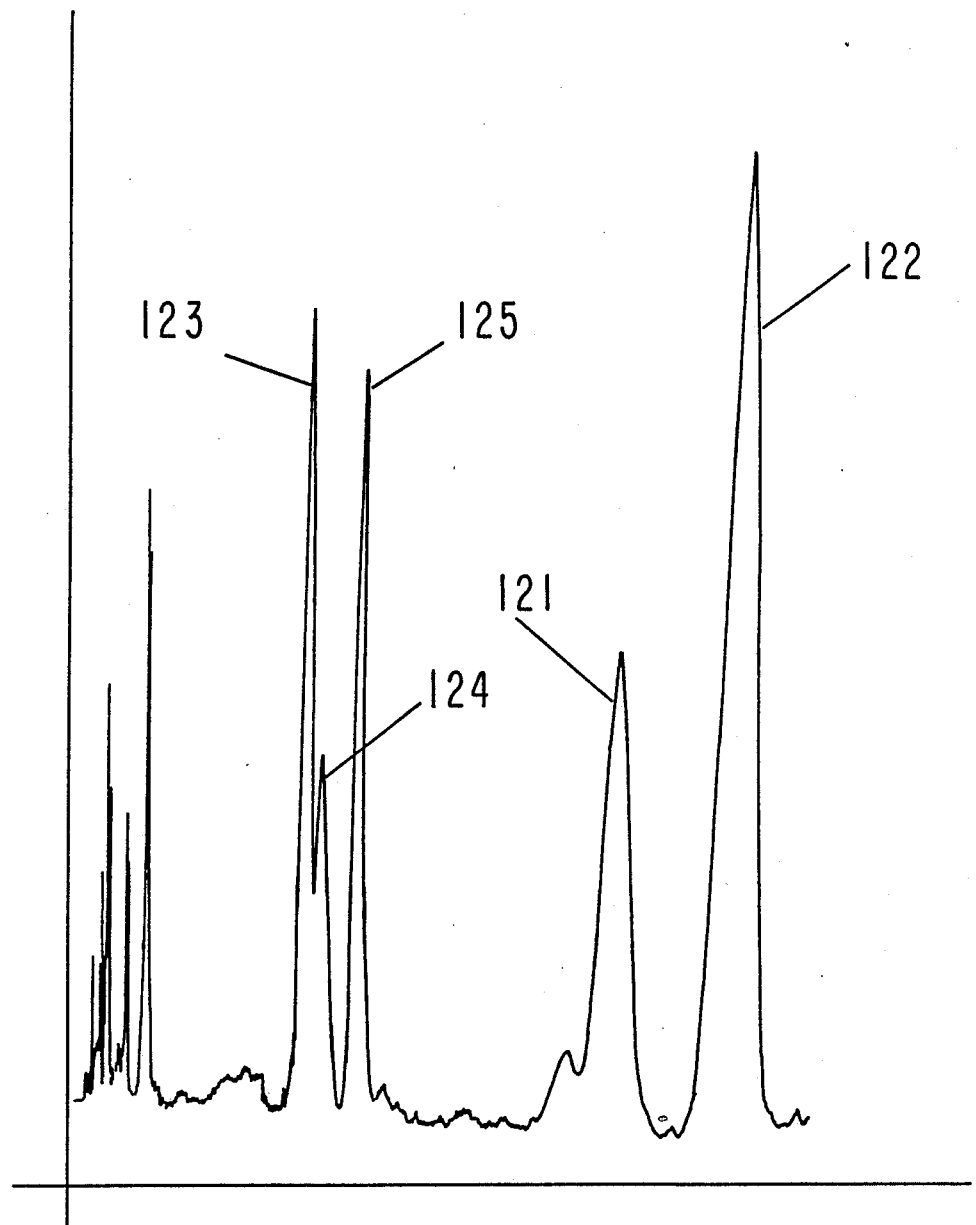

FIG. 12 is the GLC profile for the reaction product of Example VI containing the compounds having the structures:

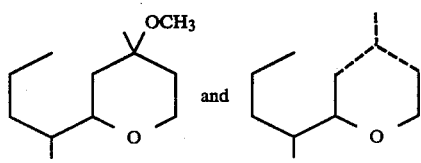

wherein in the compounds having the structure:

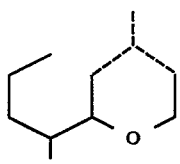

one of the dashed lines represents a carbon-carbon double bond and each of the other of the dashed lines represent carbon-carbon single bonds (Conditions: SE-30 column programmed at 120° C. isothermal).

Figure 13:
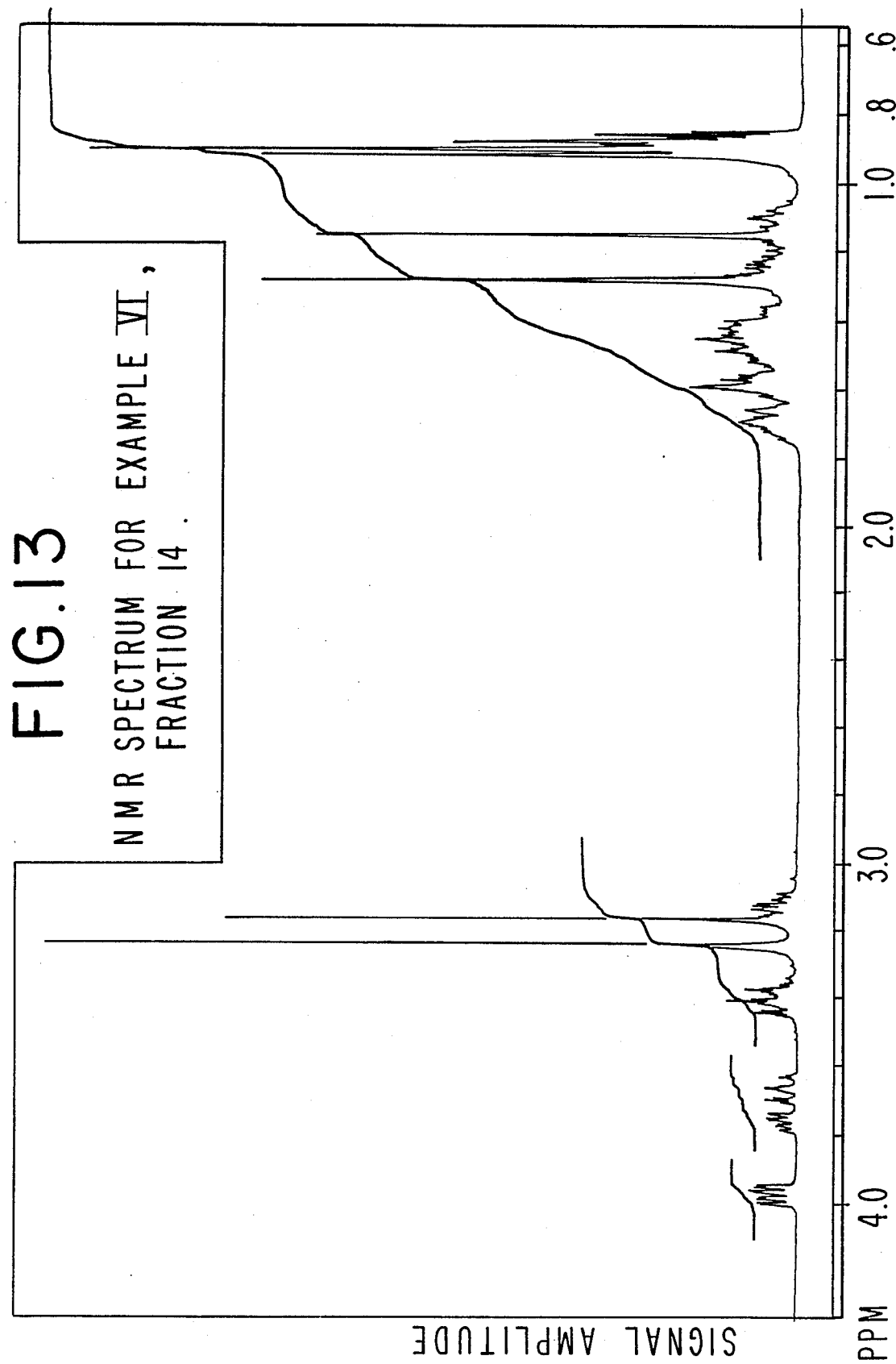

FIG. 13 is the NMR spectrum for Fraction 14 of the distillation product of the reaction product of Example VI which is for the compound having the structure:

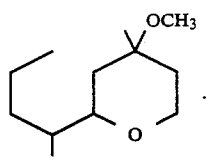

Figure 14:
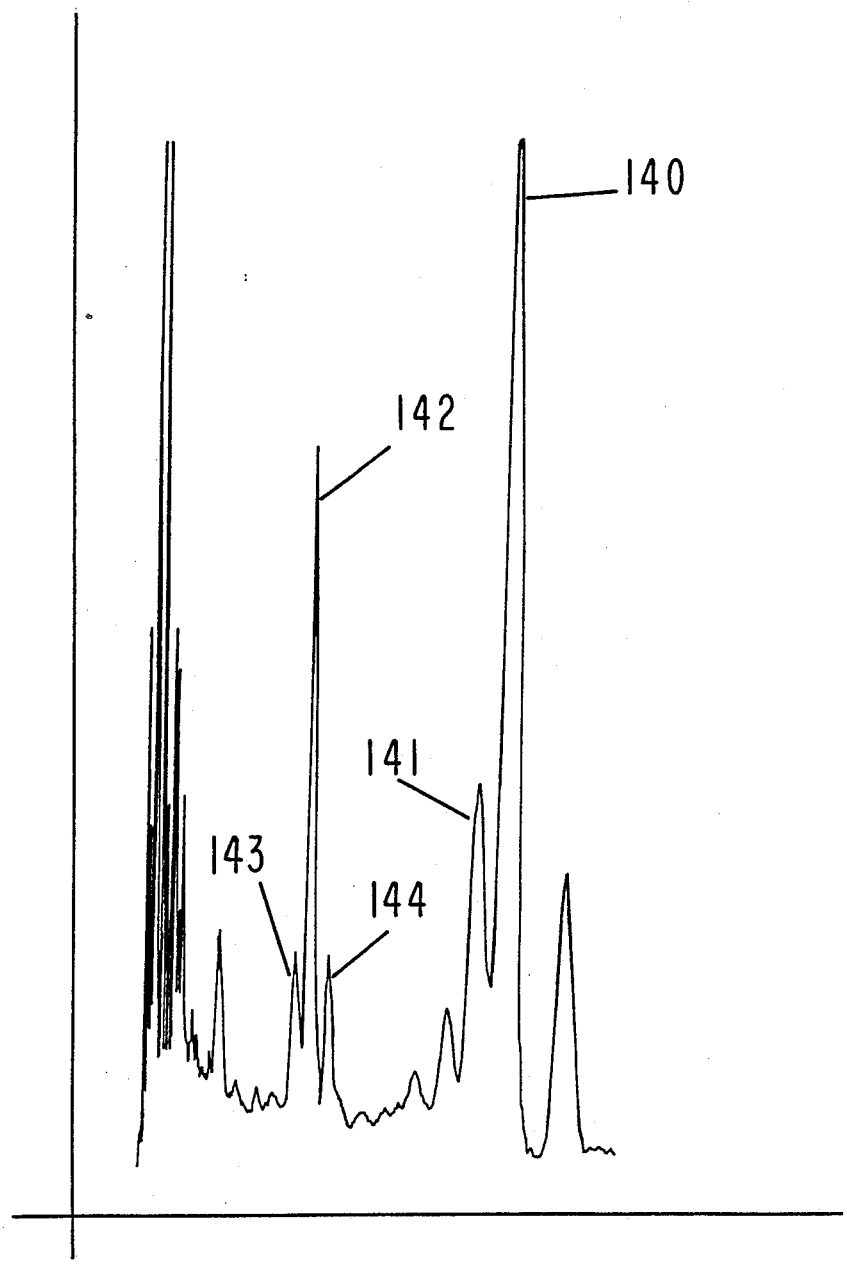

FIG. 14 is the GLC profile for the reaction product of Example VII containing the compounds having the structures:

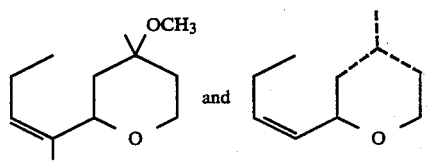

wherein in the compounds having the structure:

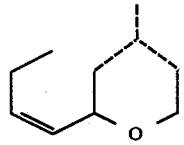

one of the dashed lines represents a carbon-carbon double bond and each of the other of the dashed lines represent carbon-carbon single bonds (Conditions: SE-30 column programmed at 180° C. isothermal).

Figure 15:
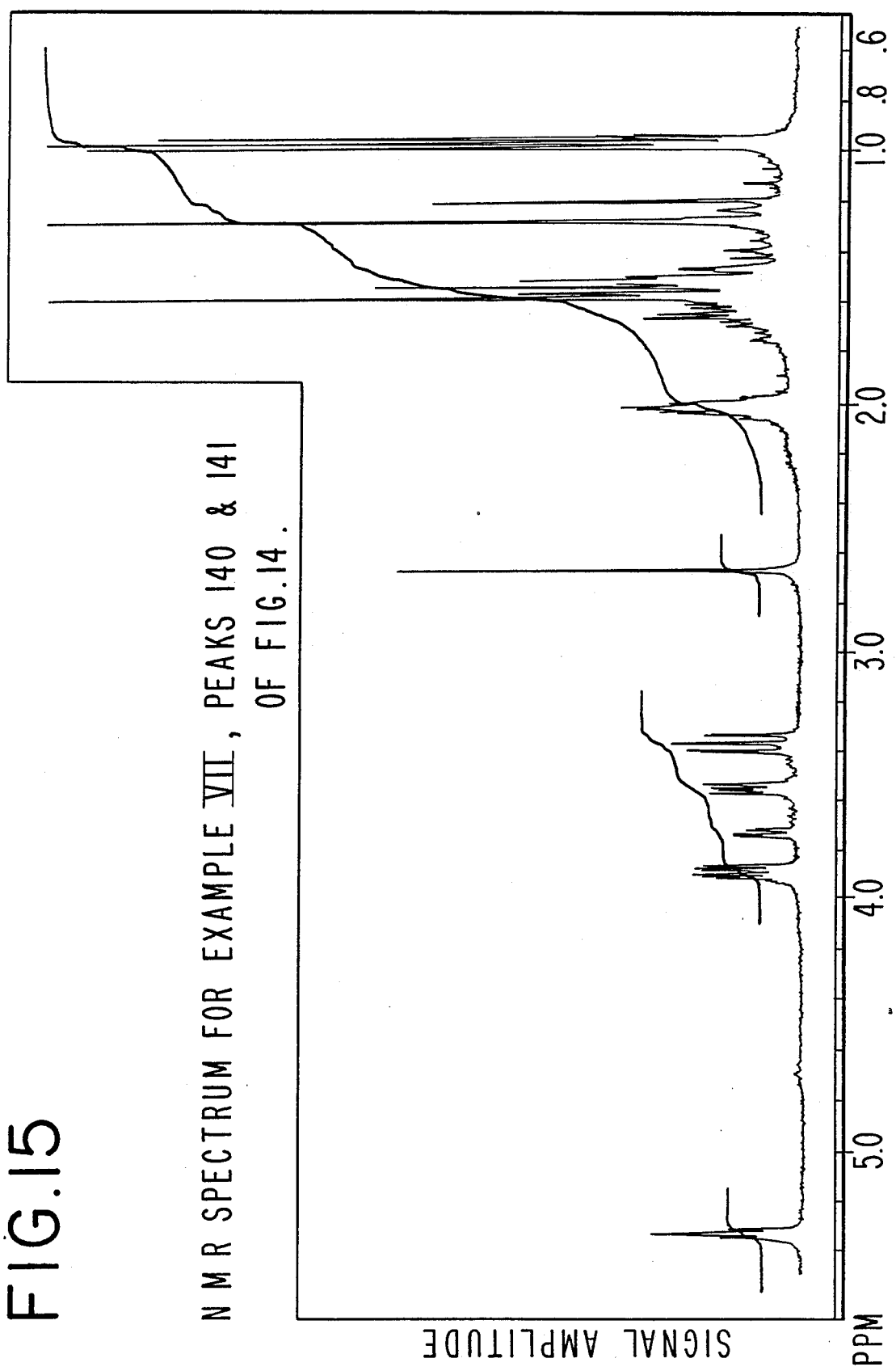

FIG. 15 is the NMR spectrum for the peak indicated by reference numerals 140 and 141 of the GLC profile of FIG. 14 for the compound having the structure:

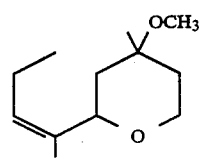

Figure 16:
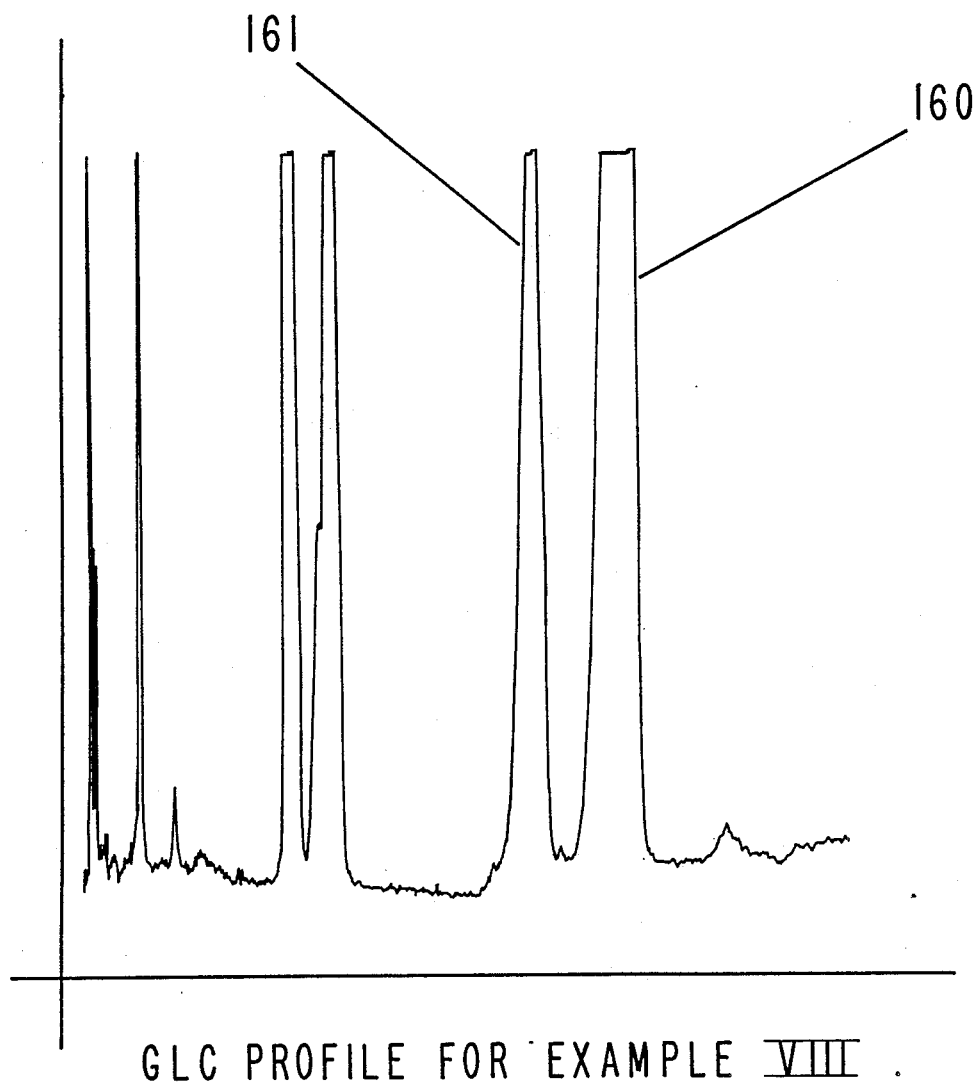

FIG. 16 is the GLC profile for the reaction product of Example VIII containing the compounds having the structures:

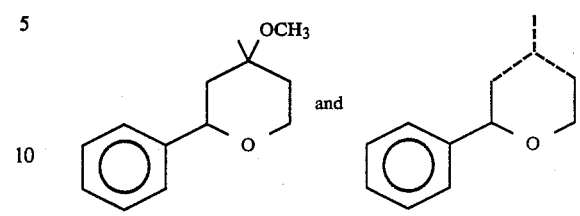

wherein in the compounds having the structure:

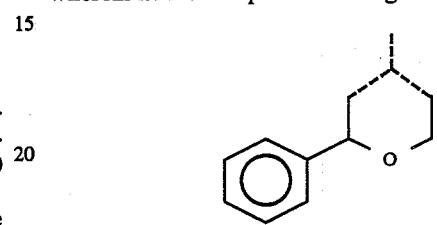

one of the dashed lines represents a carbon-carbon double bond and each of the other of the dashed lines represent carbon-carbon single bonds (Conditions: SE-30 column programmed at 160° C. isothermal).

Figure 17:
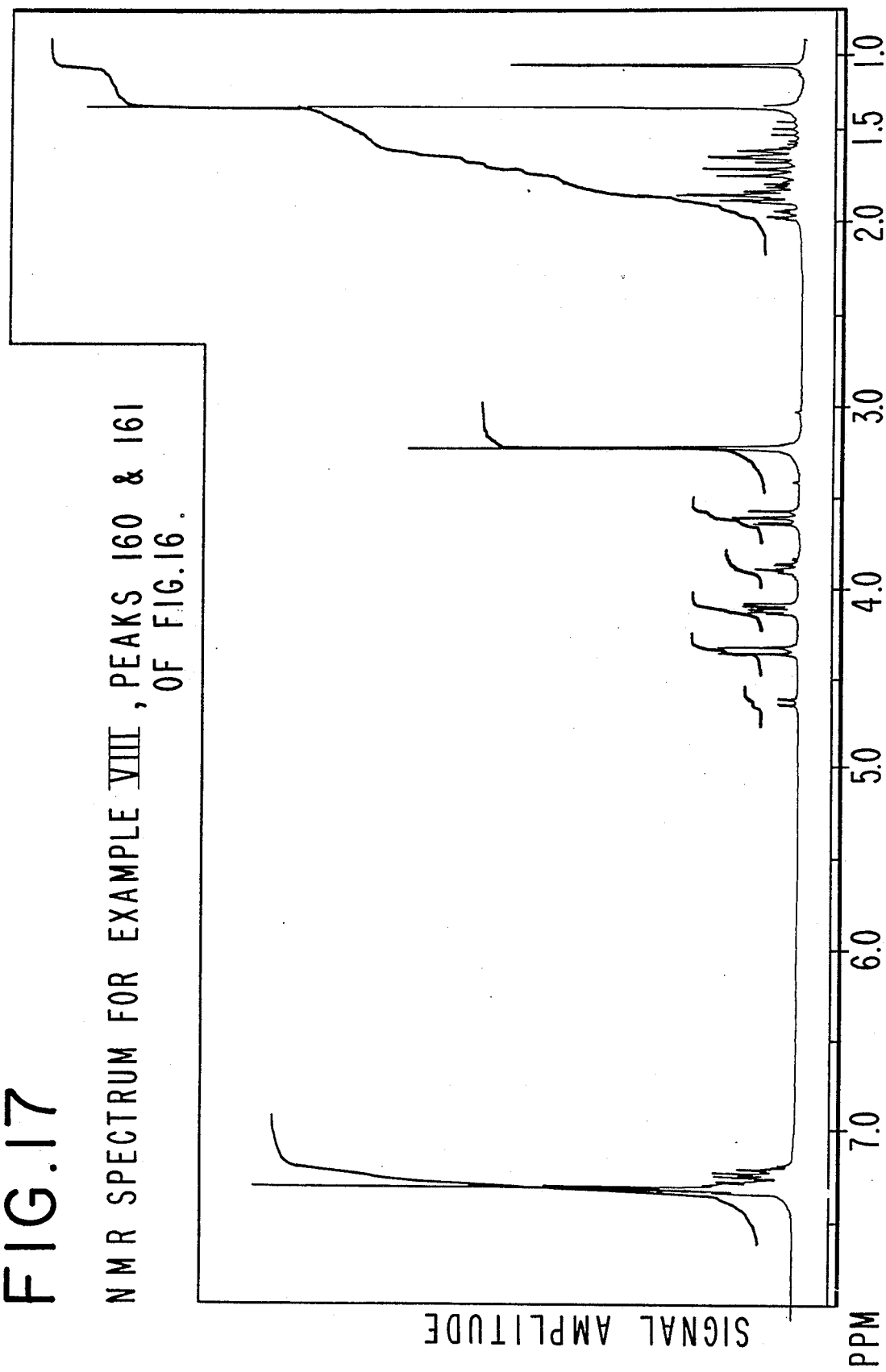

FIG. 17 is the NMR spectrum for the peaks indicated by reference numerals 160 and 161 of the GLC profile of FIG. 16 for the compound having the structure:

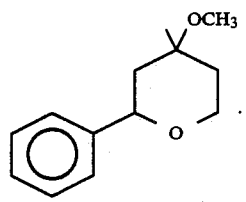

Figure 18:
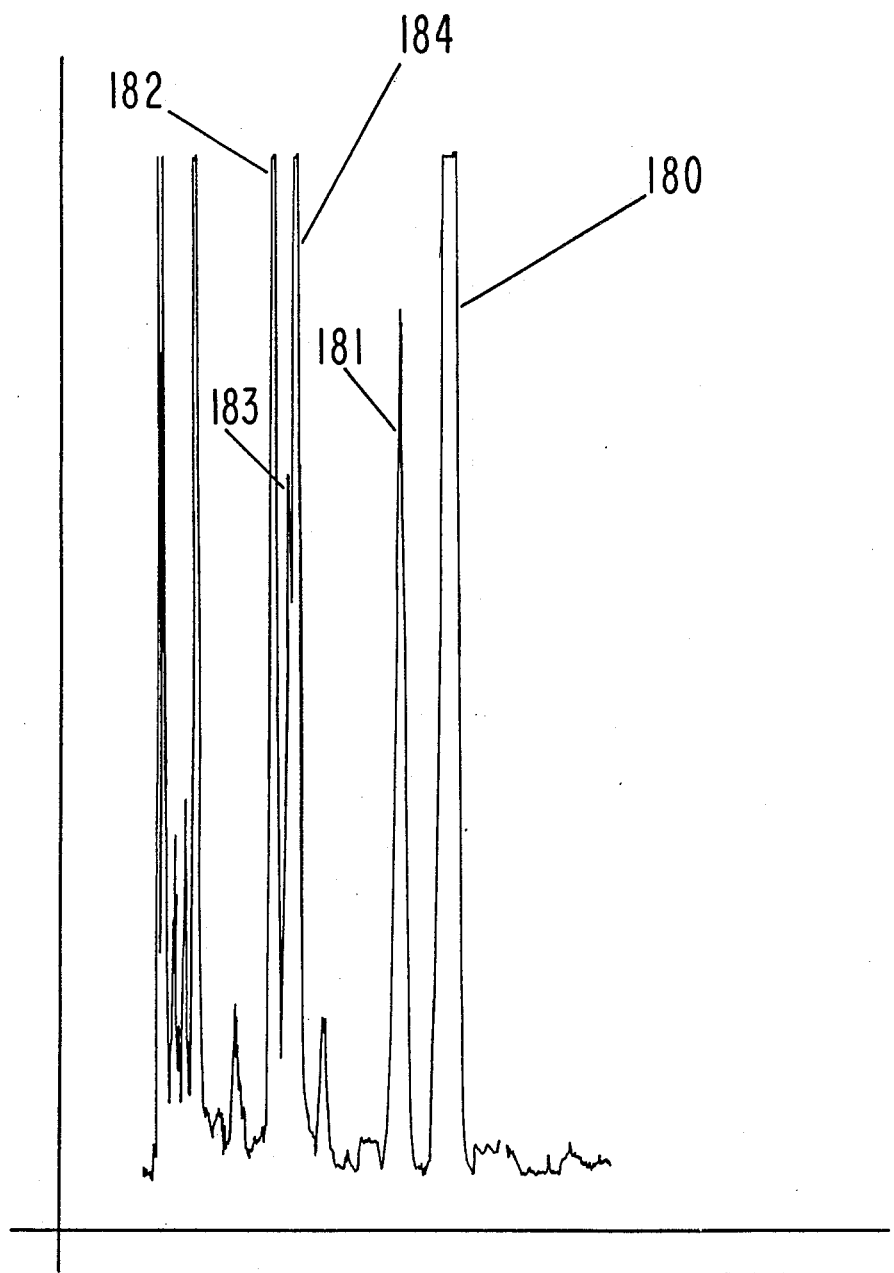

FIG. 18 is the GLC profile for the reaction product of Example IX containing the compounds having the structures:

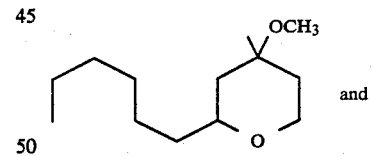

wherein in the compounds having the structure:

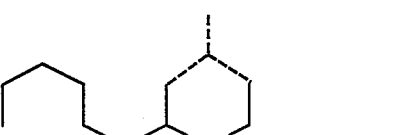

one of the dashed lines represents a carbon-carbon double bond and each of the other of the dashed lines represent carbon-carbon single bonds.

Figure 19:
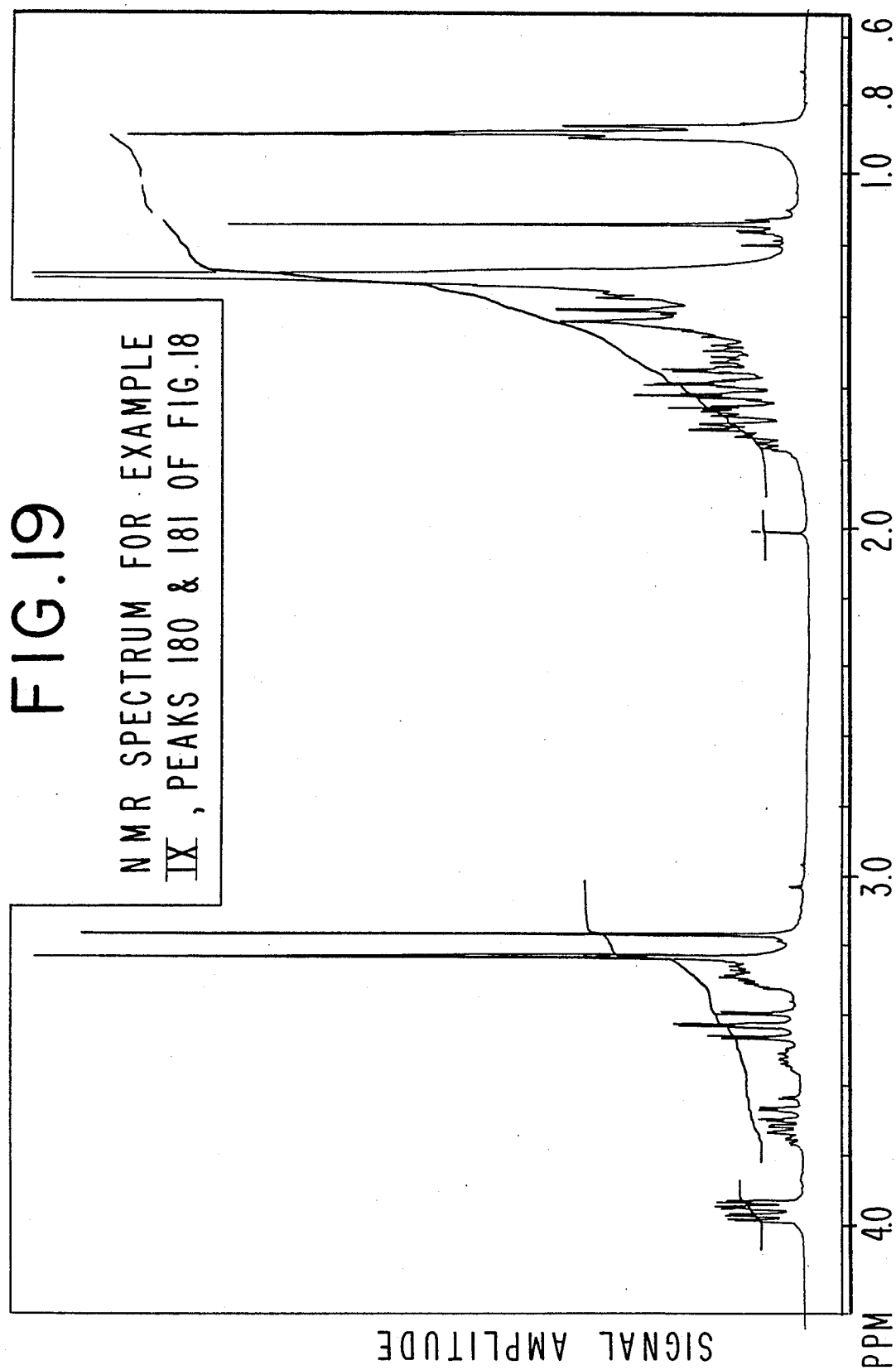

FIG. 19 is the NMR spectrum for the peaks indicated by reference numerals 180 and 181 of the GLC profile of FIG. 18 for the compound having the structure:

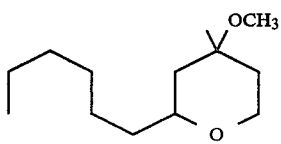

prepared according to Example IX.

Figure 20:
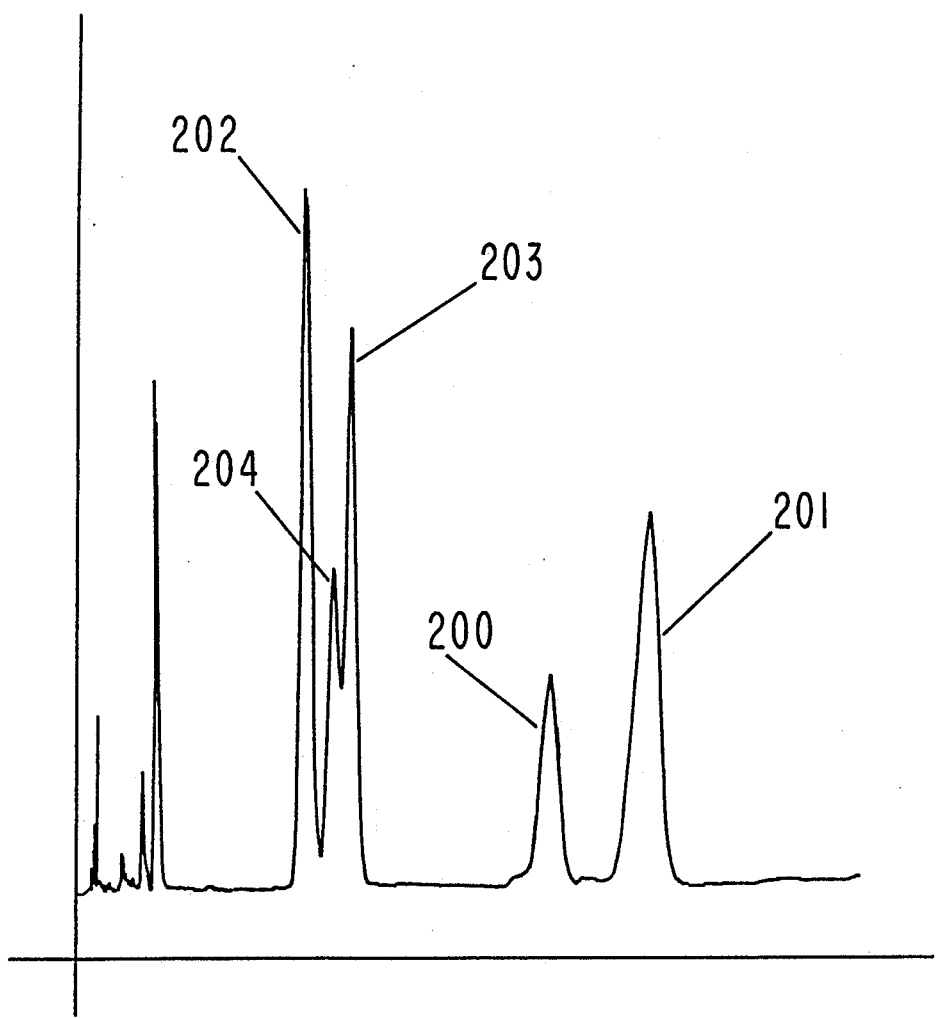

FIG. 20 is the GLC profile for the reaction product of Example X containing the compounds having the structures:

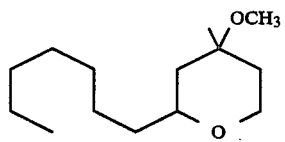

and

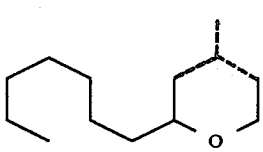

wherein in the compounds having the structure:

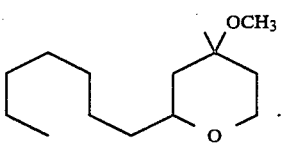

one of the dashed lines represents a carbon-carbon double bond and each of the other of the dashed lines represent carbon-carbon single bonds.

Figure 21:
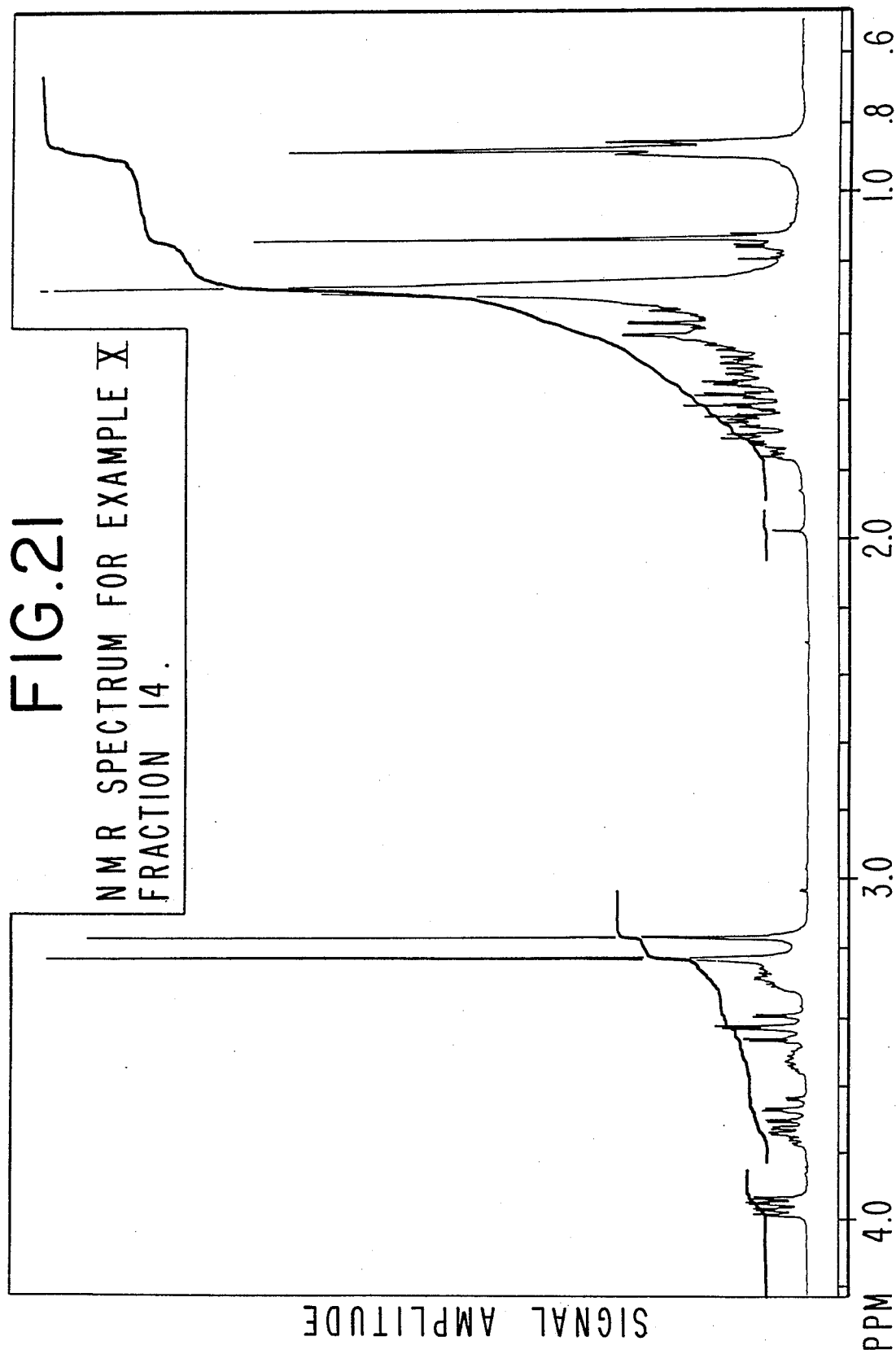

FIG. 21 is the NMR spectrum for Fraction 14 of the distillation product of the reaction product of Example X and is for the compound having the structure:

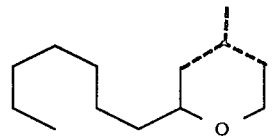

Figure 22:
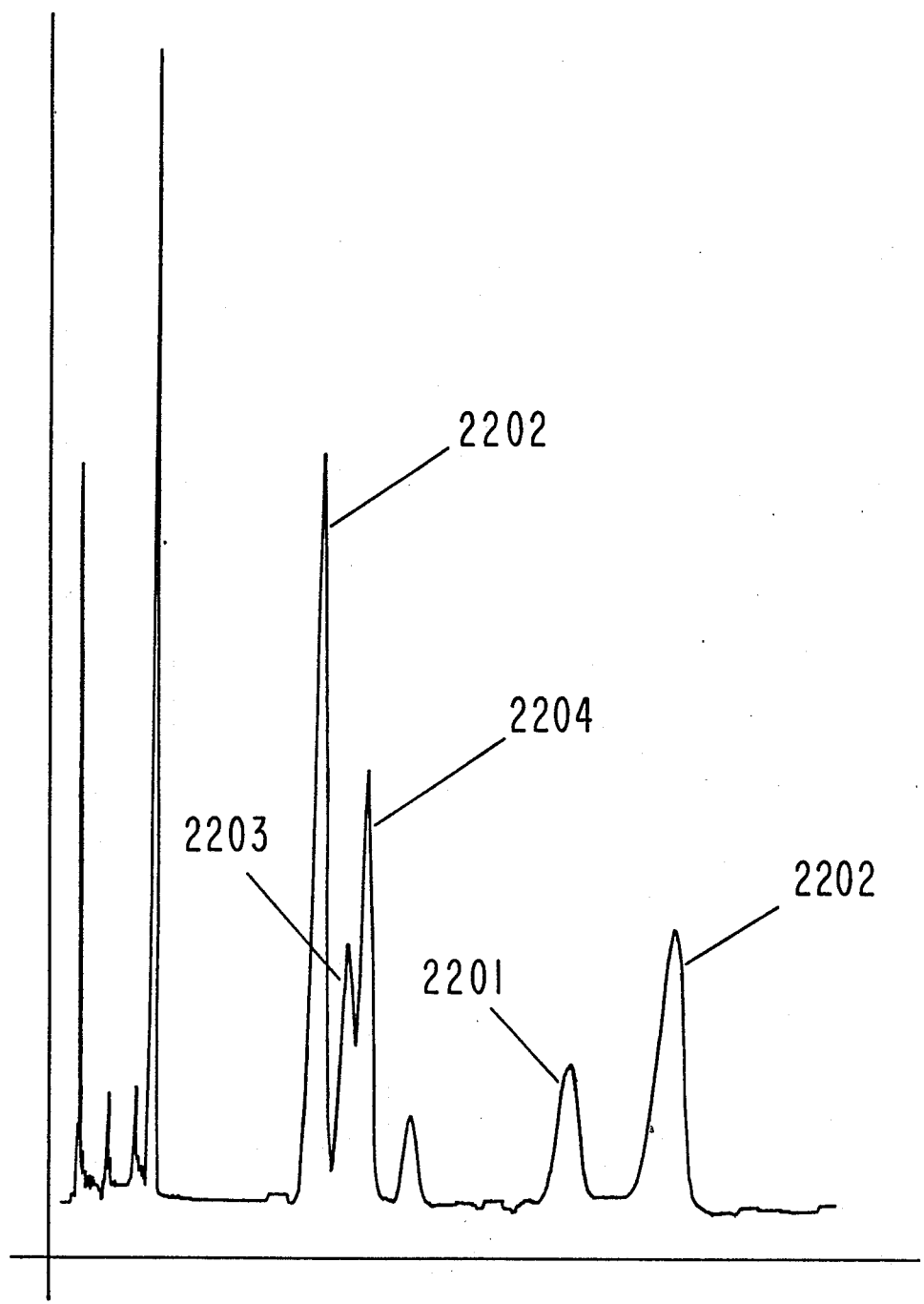

FIG. 22 is the GLC profile for the reaction product of Example XI containing the compounds having the structures:

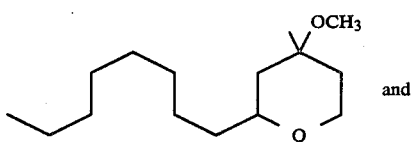

and

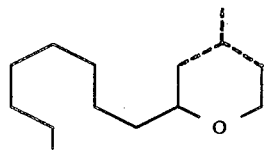

wherein in the compounds having the structure:

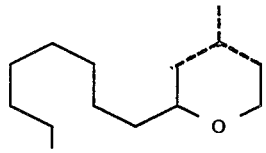

one of the dashed lines represents a carbon-carbon double bond and each of the other of the dashed lines represent carbon-carbon single bonds.

Figure 23:
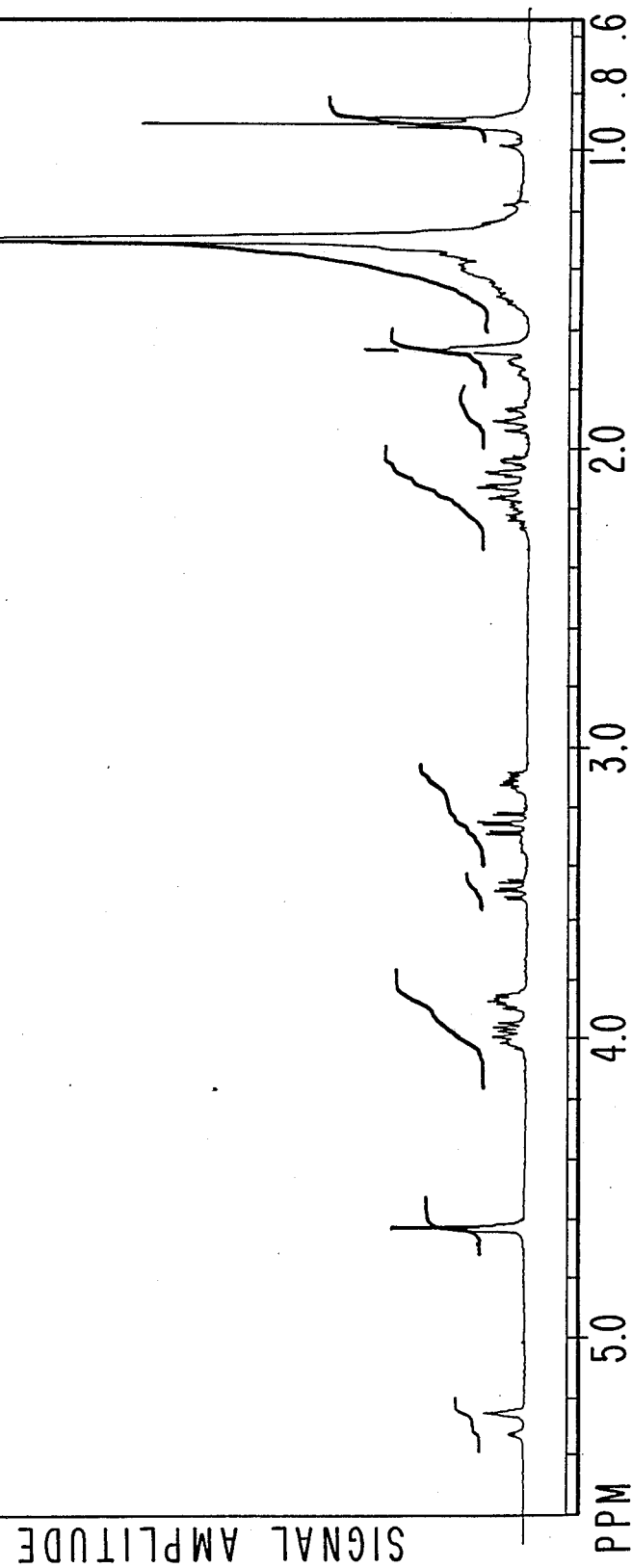

FIG. 23 is the NMR spectrum for the peaks indicated by reference numerals 2202, 2203 and 2204 of the GLC profile of FIG. 22 for the mixture of compounds having the structure:

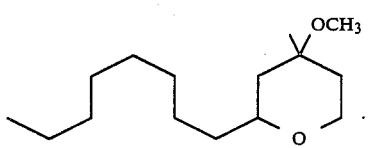

wherein in the mixture of compounds having the structure:

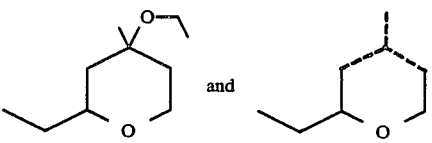

one of the dashed lines represents a carbon-carbon double bond and each of the other of the dashed lines represent carbon-carbon single bonds.

Figure 24:
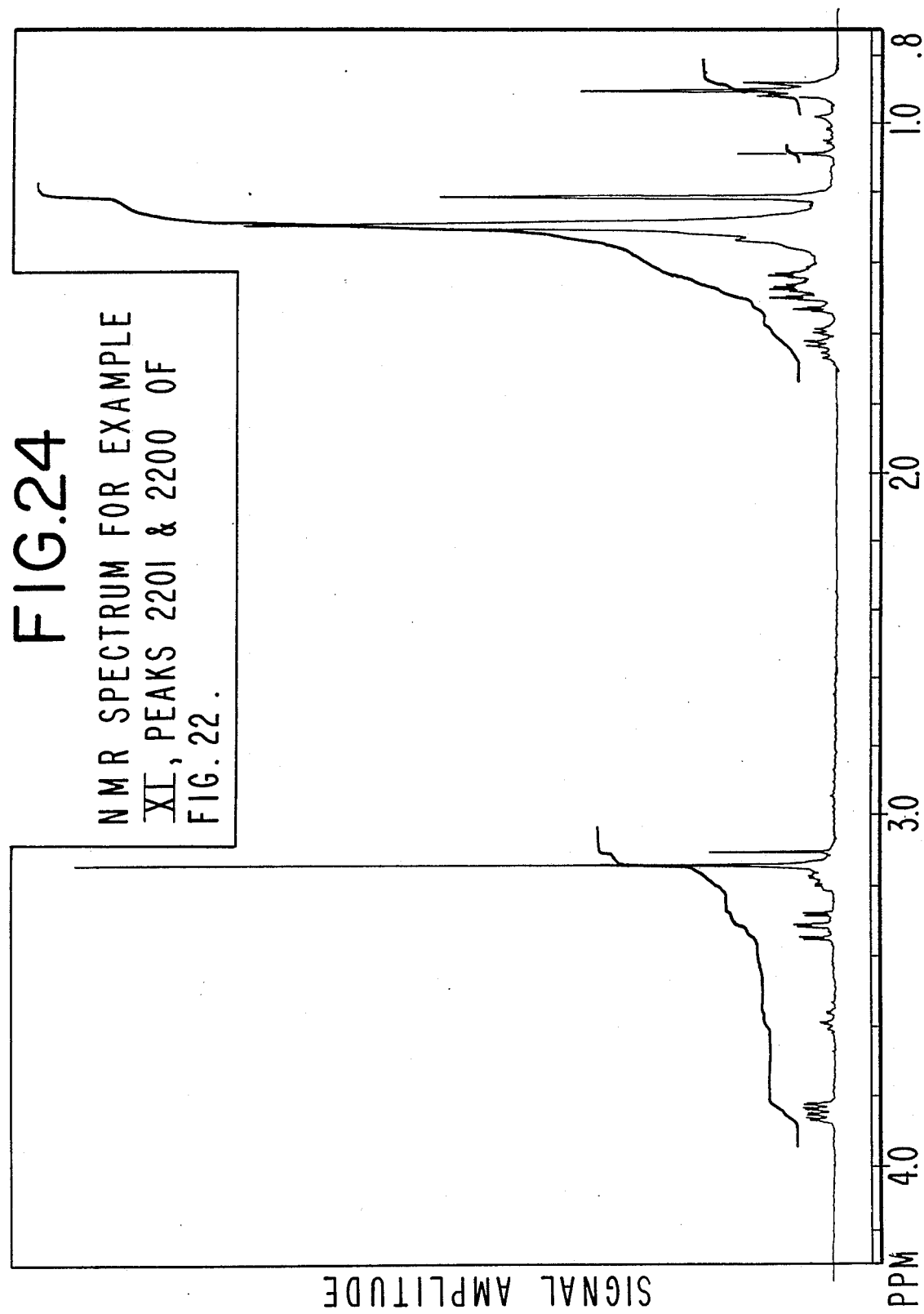

FIG. 24 is the NMR spectrum for the peaks indicated by reference numerals 2201 and 2200 of the GLC profile of FIG. 22 for the compound having the structure:

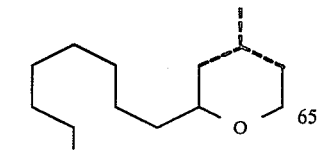

Figure 25:
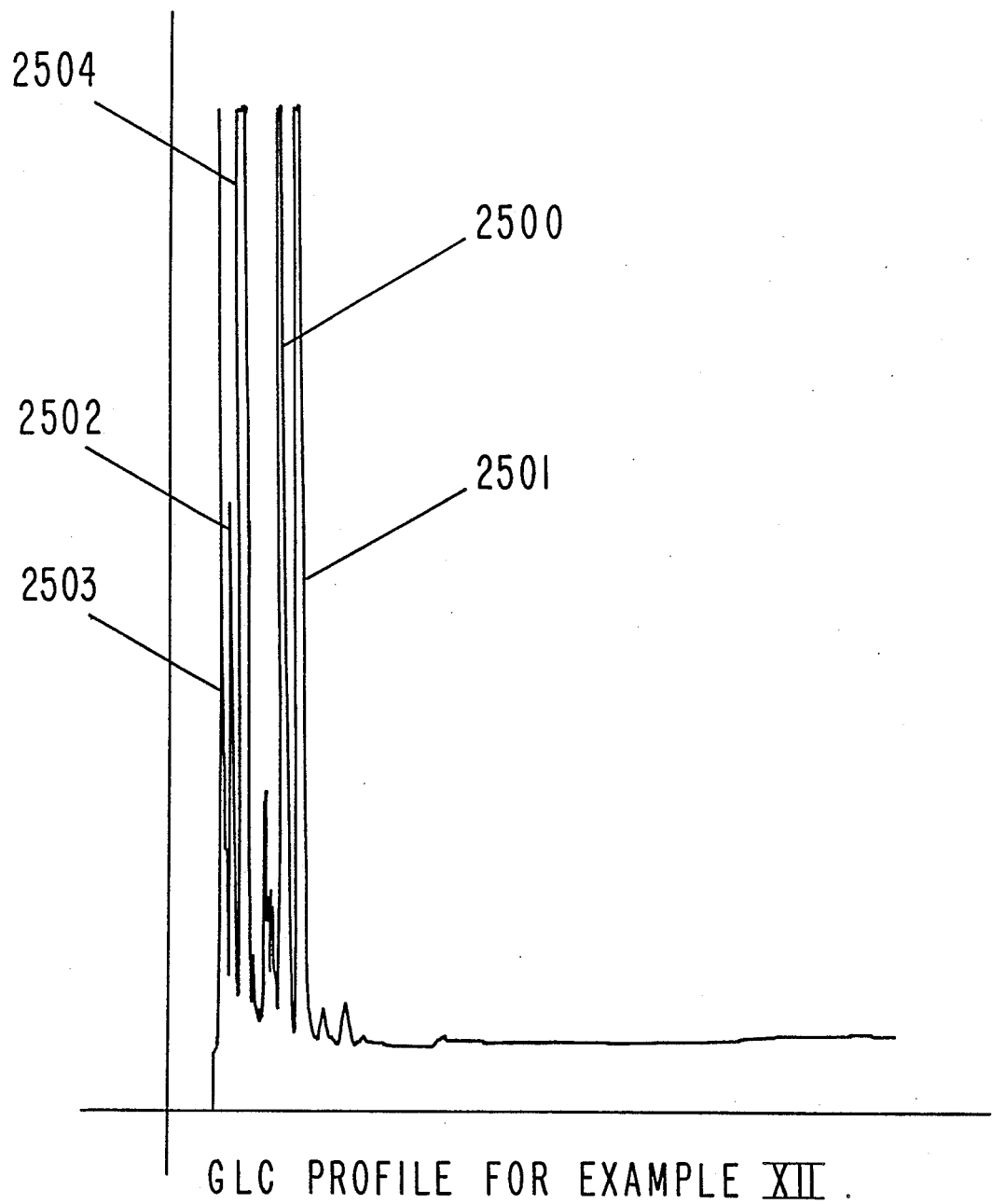

FIG. 25 is the GLC profile for the reaction product of Example XII for the compounds having the structures:

and wherein in the compounds having the structure:

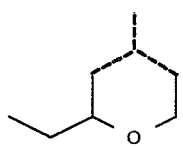

one of the dashed lines represents a carbon-carbon double bond and each of the other of the dashed lines represent carbon-carbon single bonds (Conditions: SE-30 column programmed at 160° C. isothermal).

Figure 26:
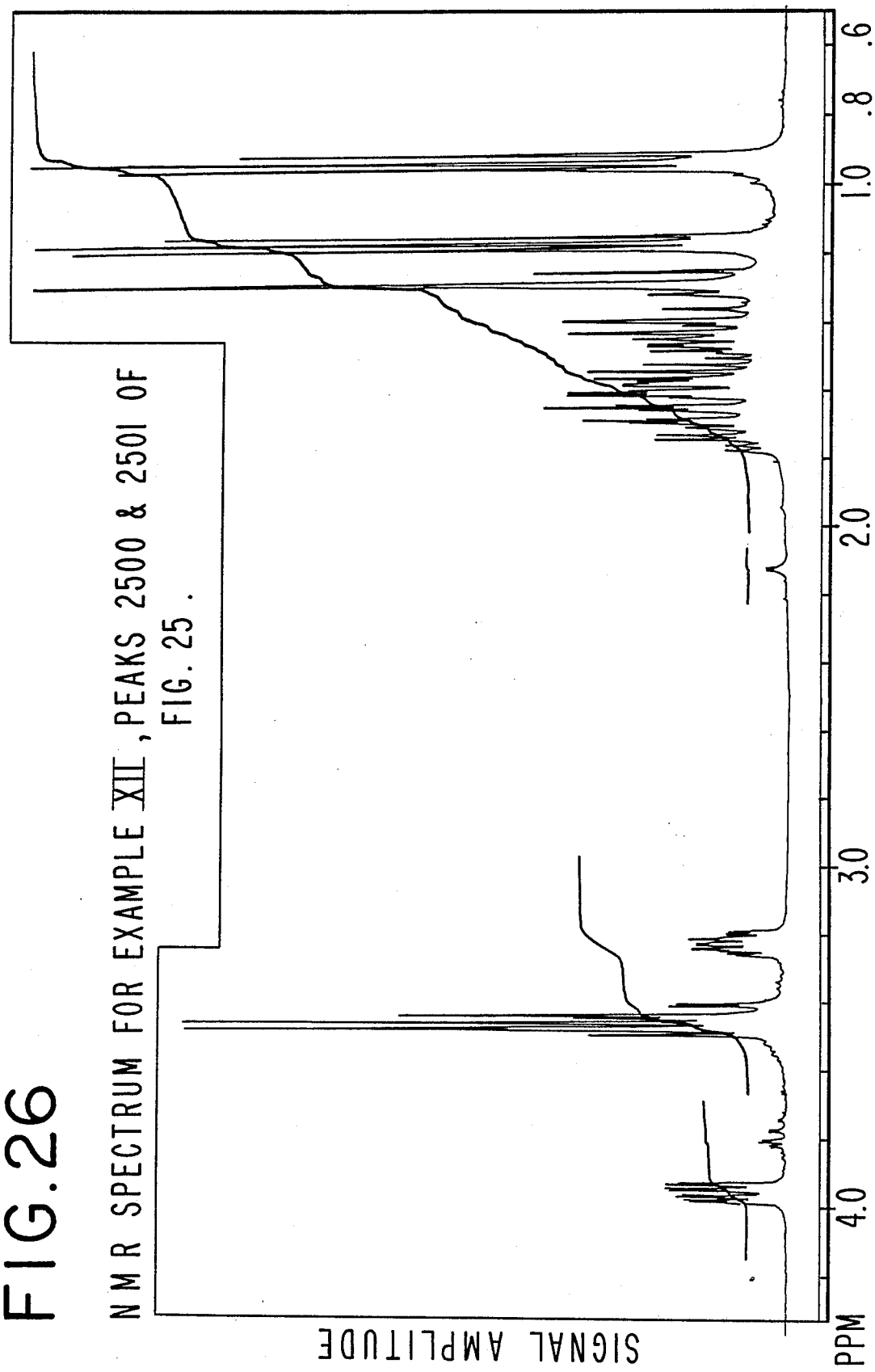

FIG. 26 is the NMR spectrum for the peaks indicated by reference numerals 2500 and 2501 of the GLC profile of FIG. 25 for the compound having the structure:

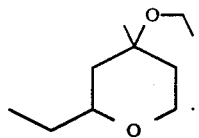

Figure 27:
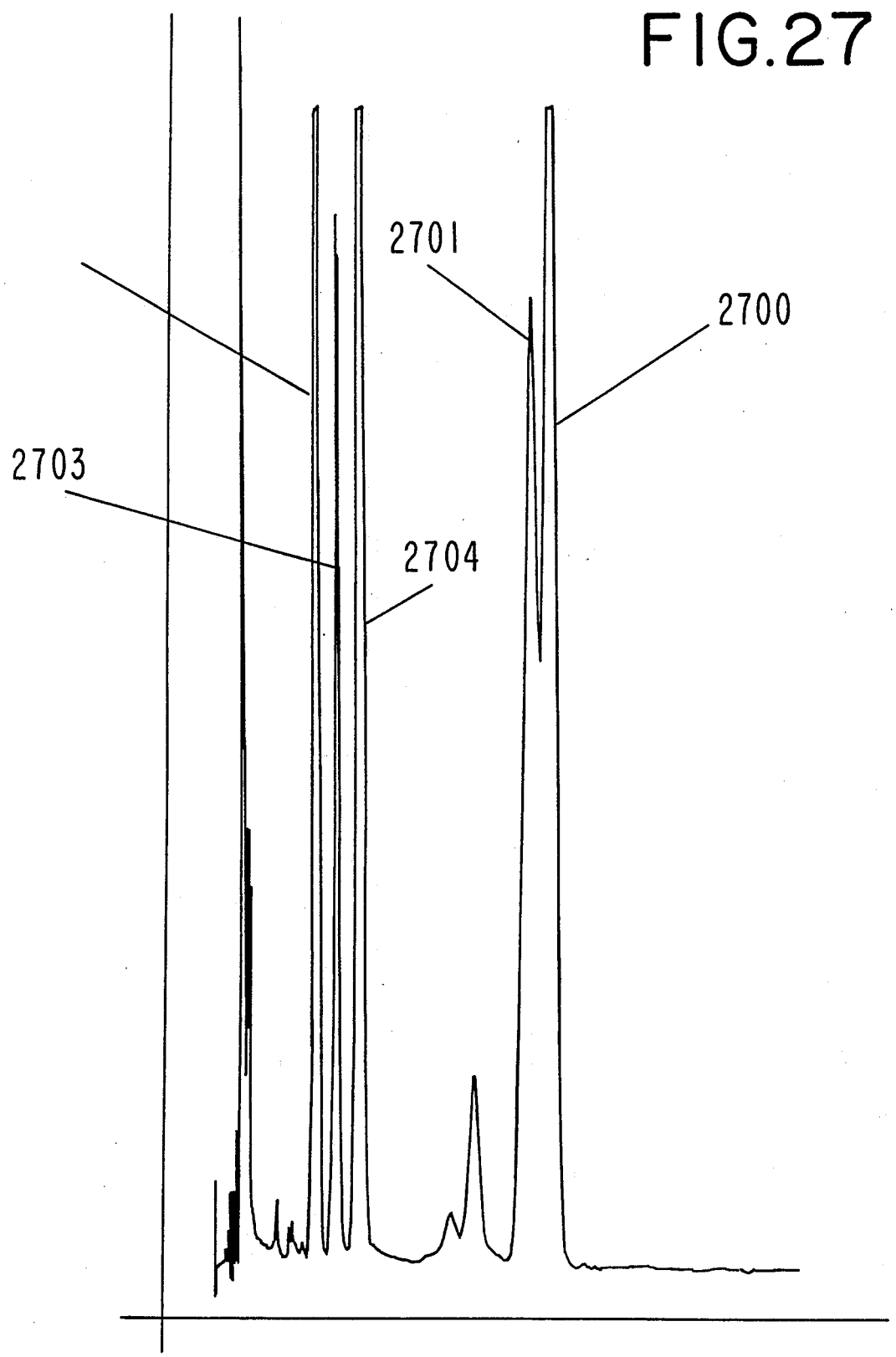

FIG. 27 is the GLC profile for the reaction product of Example XIII containing the compounds having the structures:

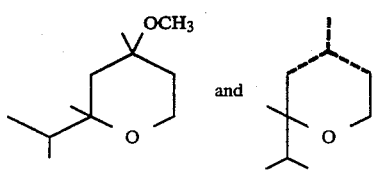

wherein in the compounds having the structure:

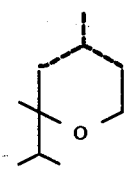

one of the dashed lines represents a carbon-carbon double bond and each of the other of the dashed lines represent carbon-carbon single bonds (Conditions: Carbowax column programmed at 120° C. isothermal).

Figure 28:
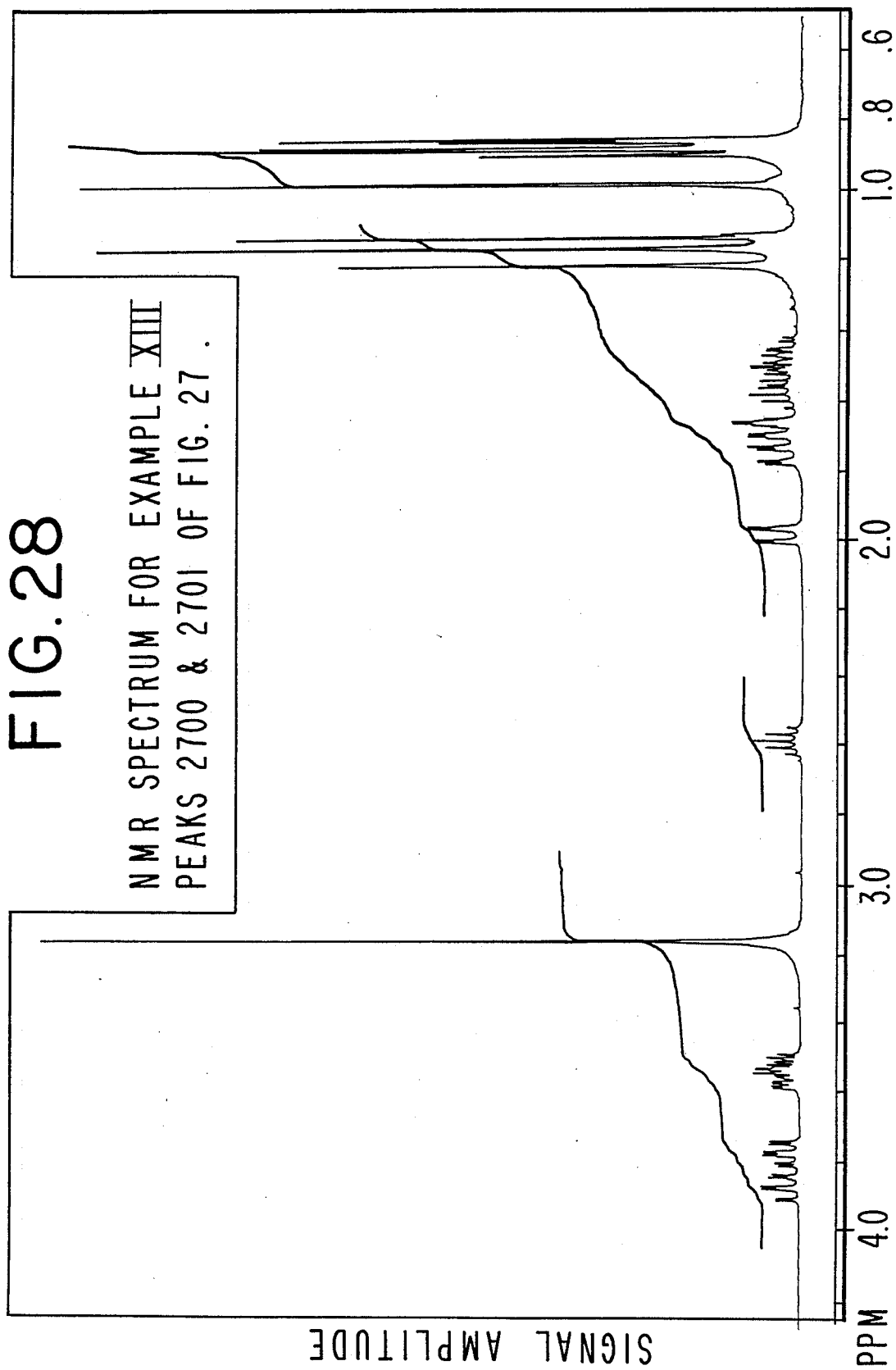

FIG. 28 is the NMR spectrum for the peaks indicated by reference numerals 2700 and 2701 of the GLC profile of FIG. 27 for the compound having the structure:

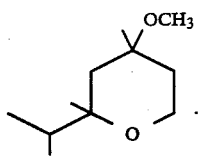

Figure 29:
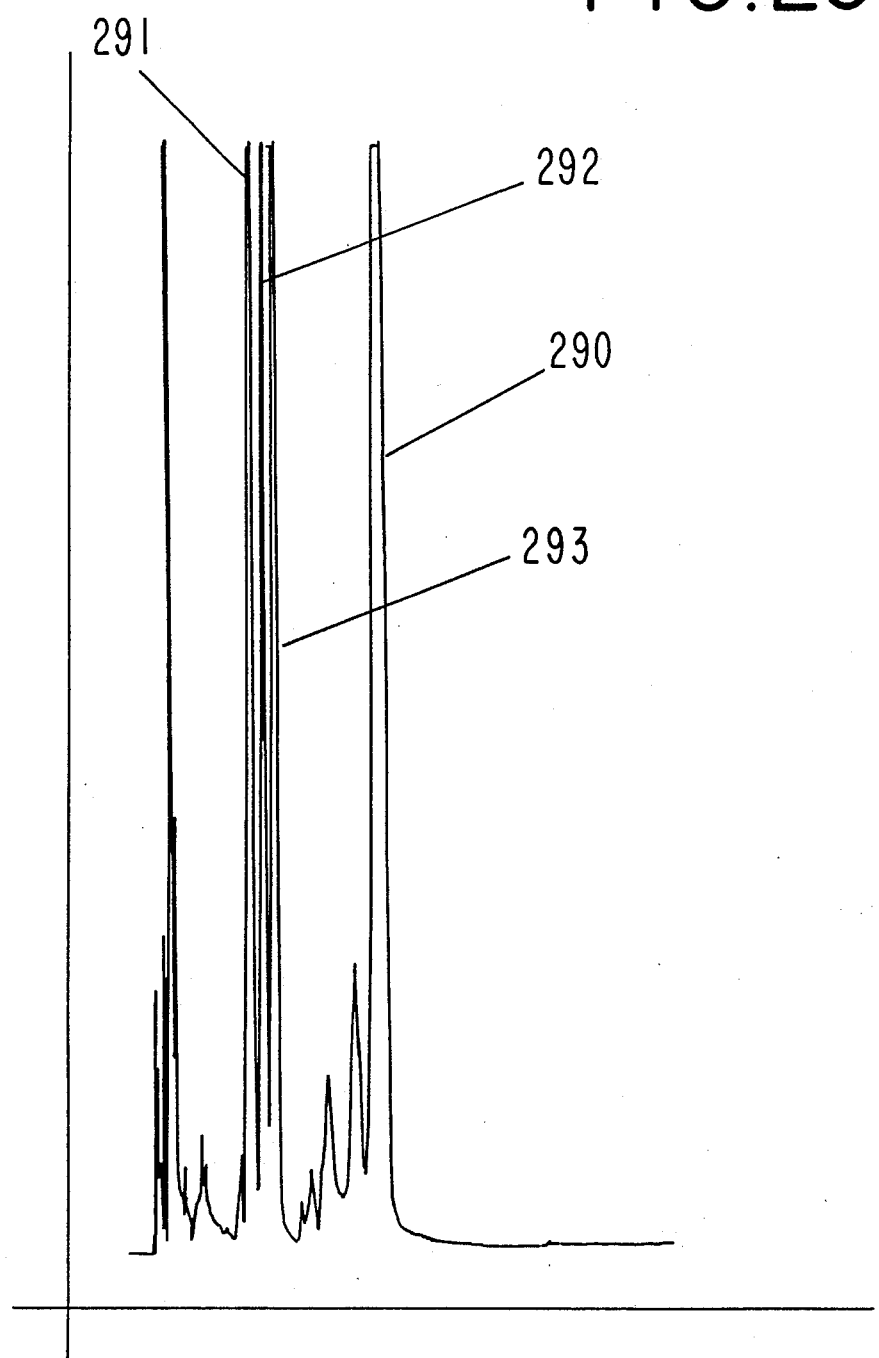

FIG. 29 is the GLC profile for the reaction product of Example XIV containing the compounds having the structures:

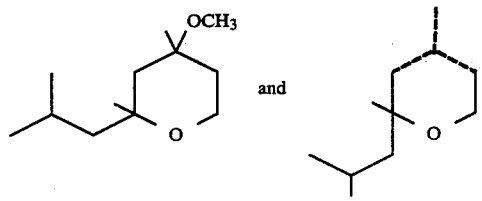

wherein in the compounds having the structure:

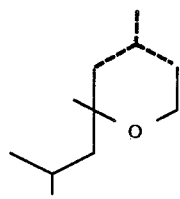

one of the dashed lines represents a carbon-carbon double bond and each of the other of the dashed lines represent carbon-carbon single bonds (Conditions: SE-30 column programmed at 200° C. isothermal).

Figure 30:
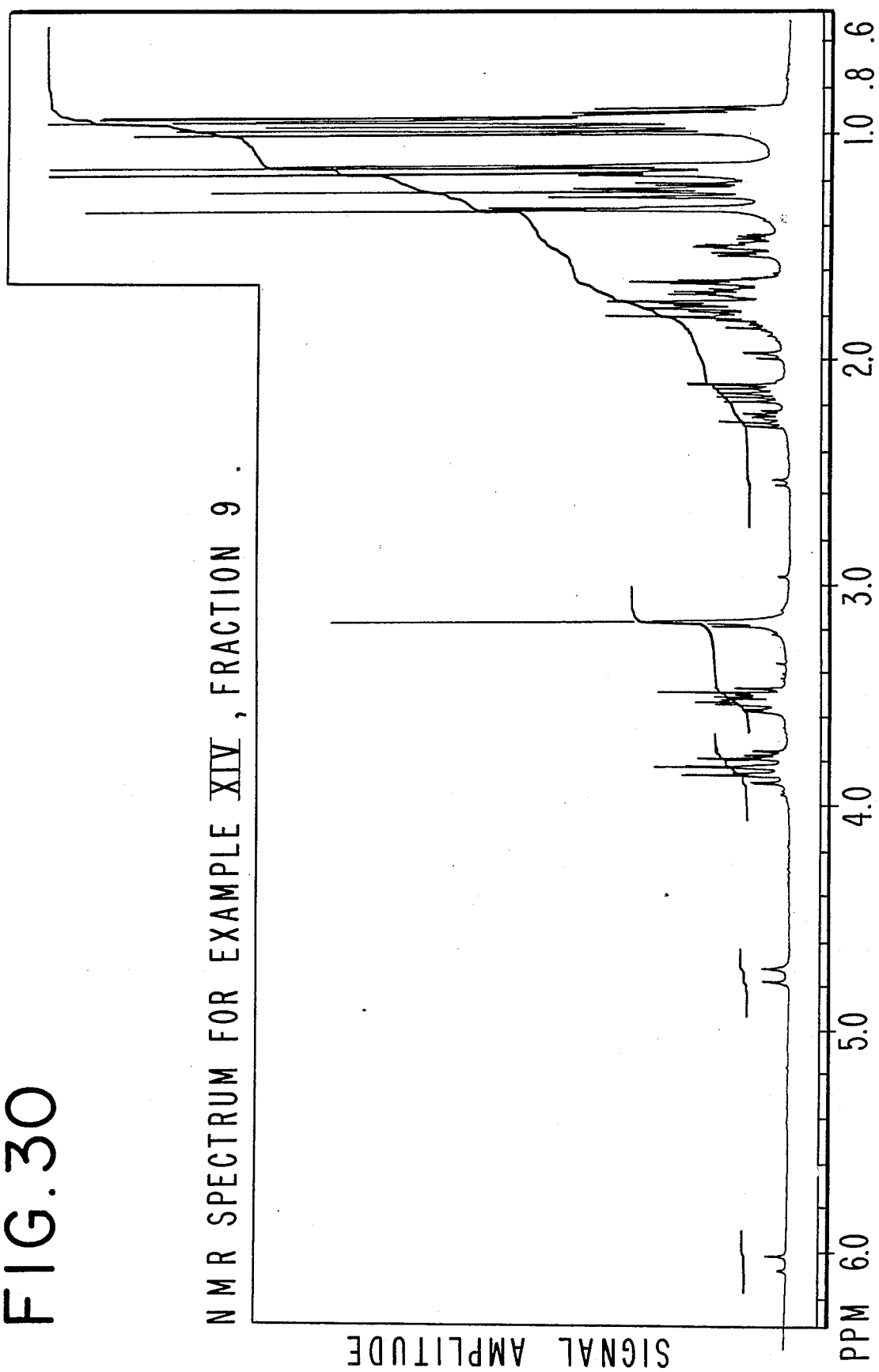

FIG. 30 is the NMR spectrum for Fraction 9 of the distillation product of the reaction product of Example XIV which is for the compound having the structure:

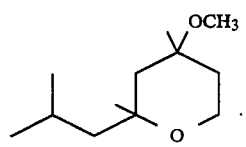

Figure 31:
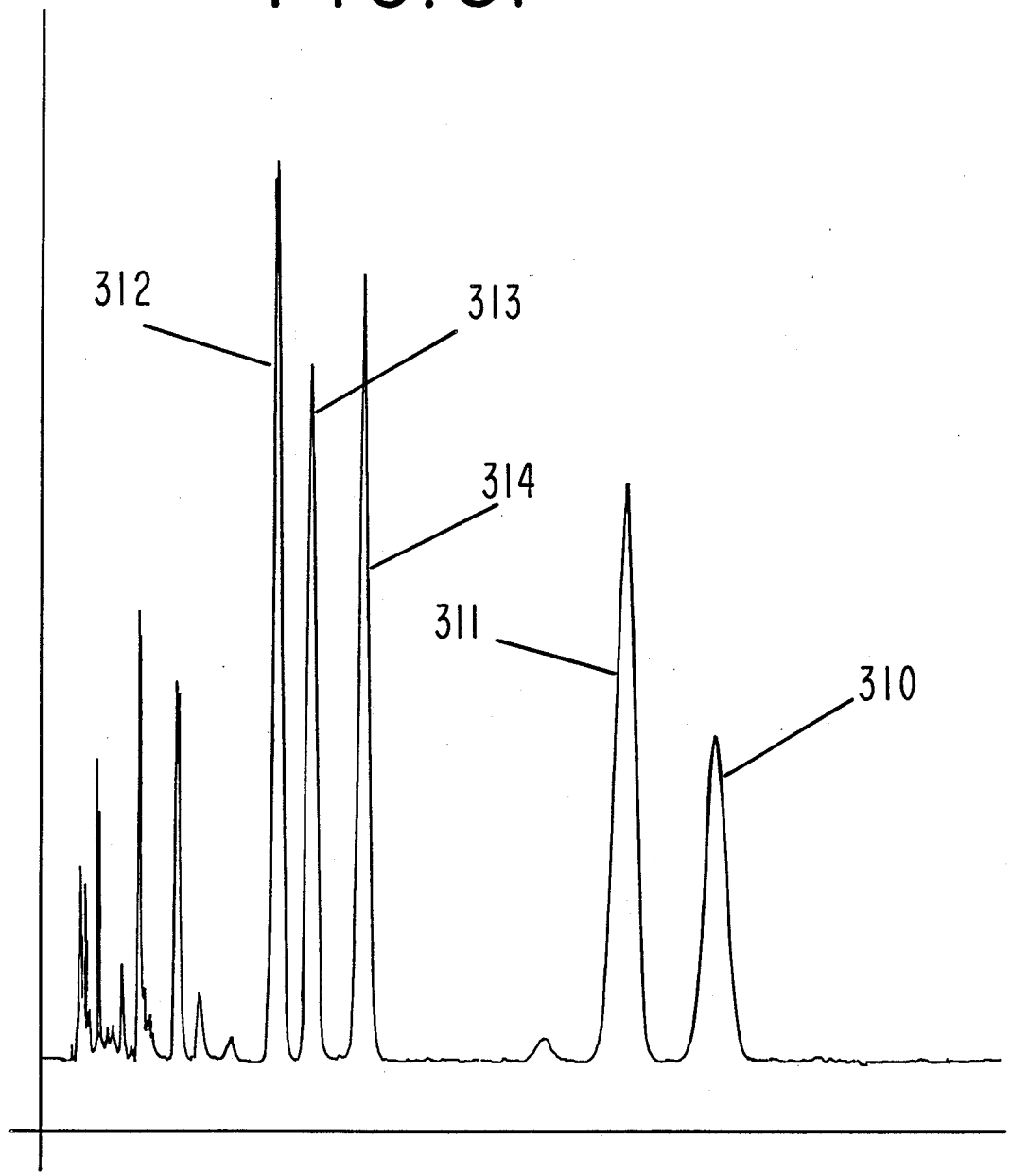

FIG. 31 is the GLC profile for the reaction product of Example XV containing the compounds having the structures:

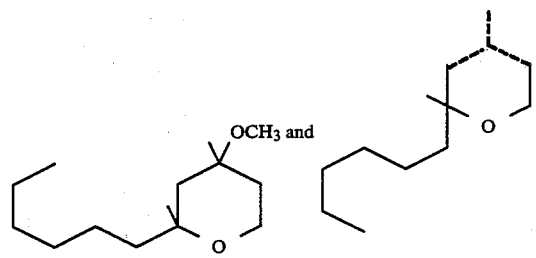

wherein in the compounds having the structure:

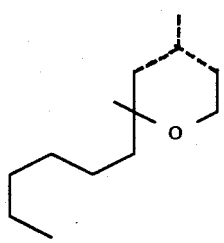

one of the dashed lines represents a carbon-carbon double bond and each of the other of the dashed lines represent carbon-carbon single bonds.

Figure 32:
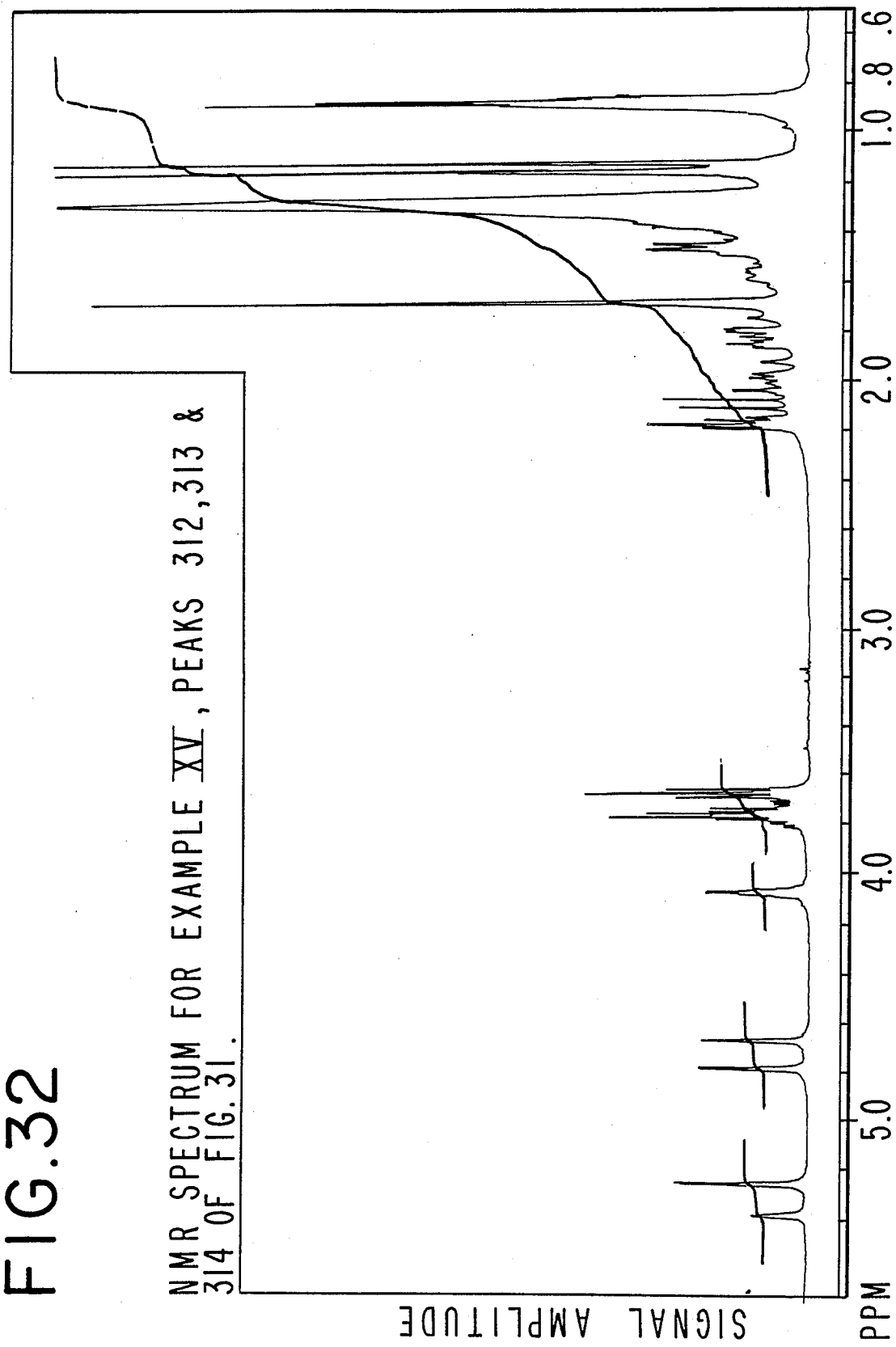

FIG. 32 is the NMR spectrum for the peaks indicated by reference numerals 312, 313 and 314 of the GLC profile of FIG. 31 for the compounds having the structure:

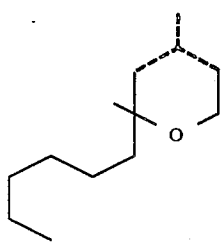

wherein in each of the compounds one of the dashed lines represents a carbon-carbon double bond and each of the other of the dashed lines is a carbon-carbon single bond.

Figure 33:
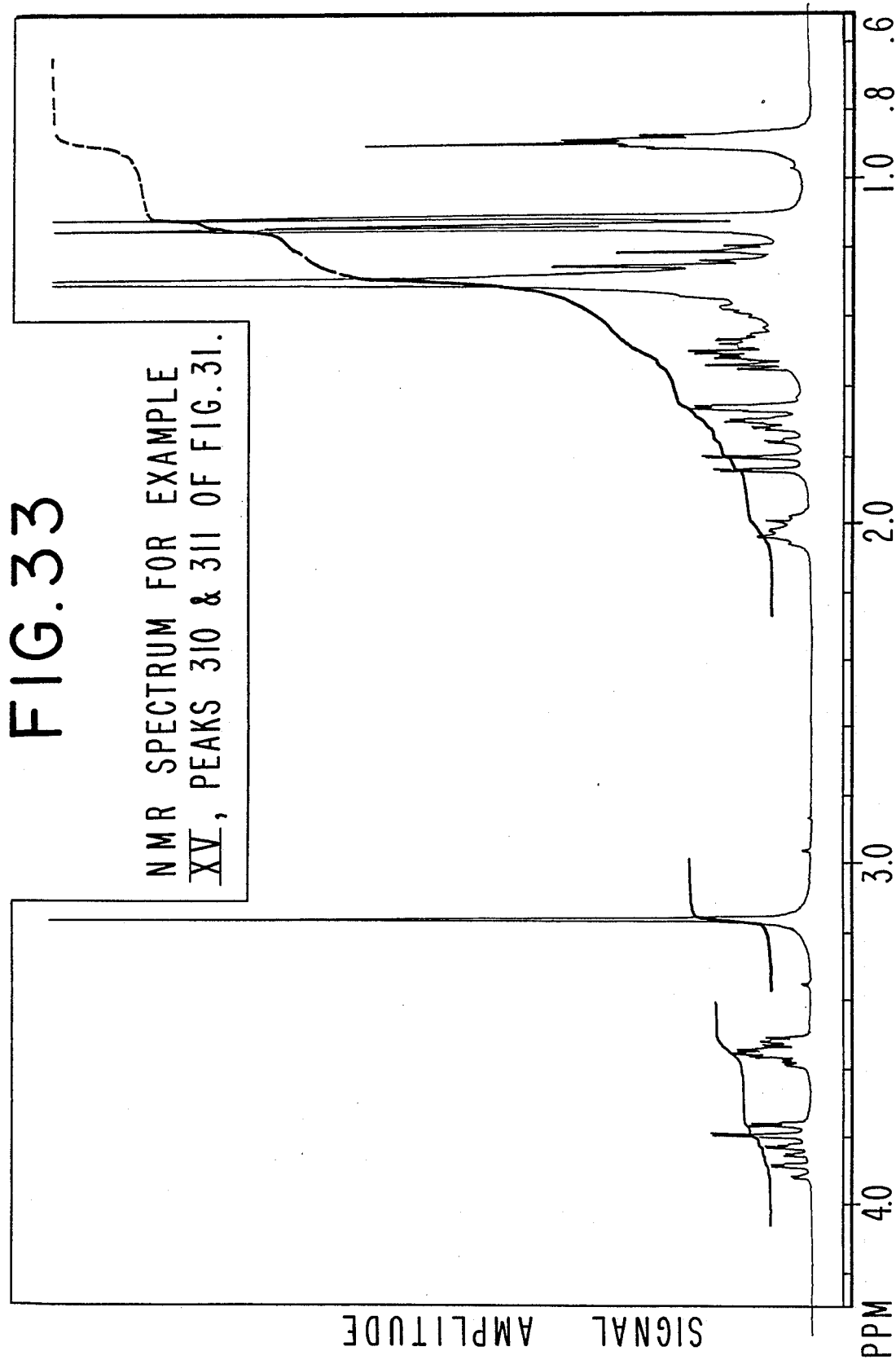

FIG. 33 is the NMR spectrum for peaks 310 and 311 of the GLC profile of FIG. 31 for the compound having the structure:

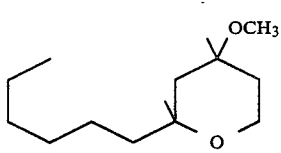

prepared according to Example XV.

Figure 34:
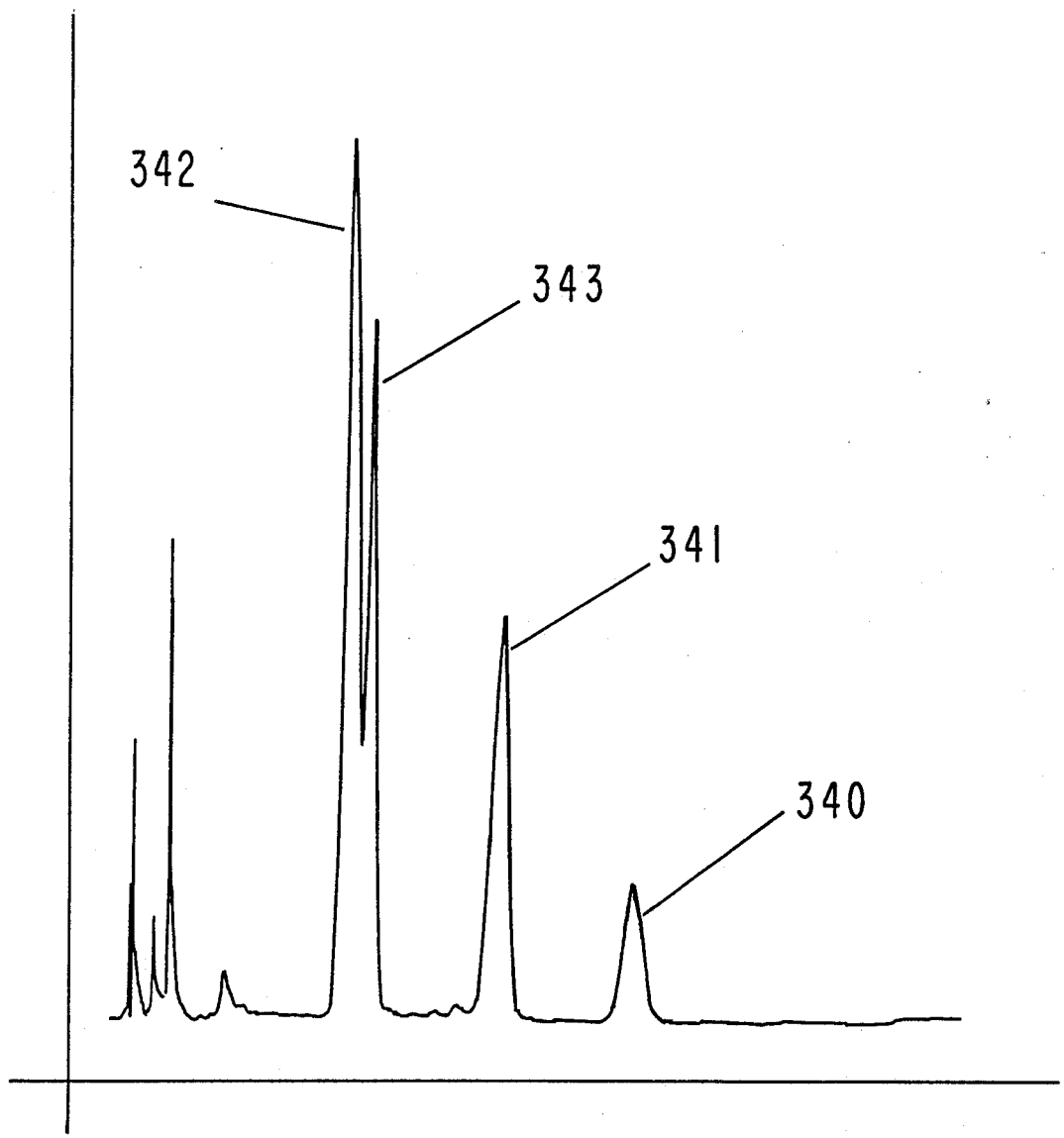

FIG. 34 is the GLC profile for the reaction product of Example XVI containing the compounds having the structures:

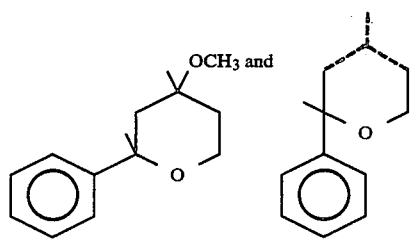

wherein in the compounds having the structure:

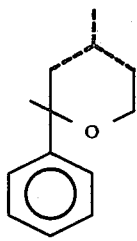

one of the dashed lines is a carbon-carbon double bond and each of the other of the dashed lines represent carbon-carbon single bonds.

Figure 35:
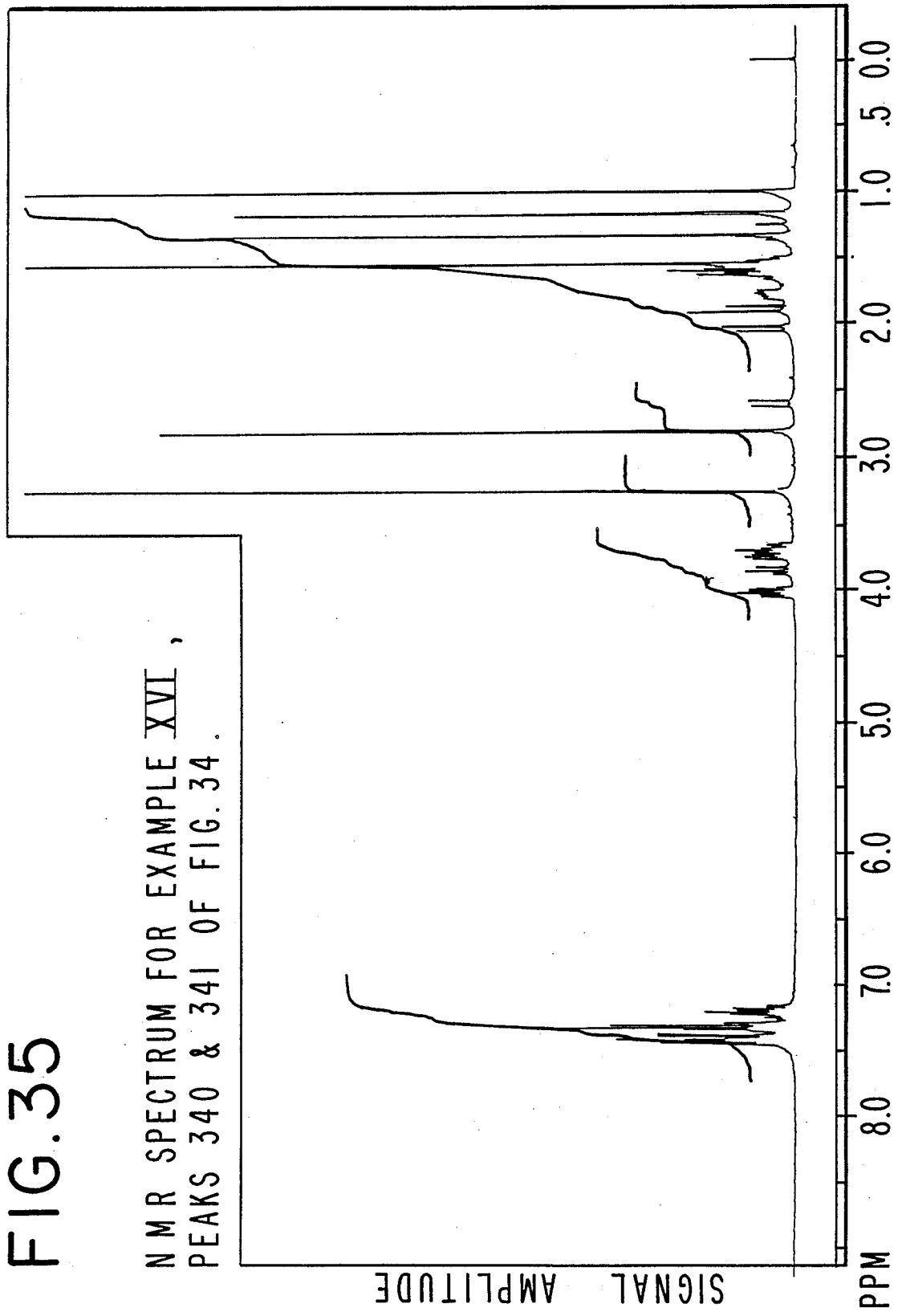

FIG. 35 is the NMR spectrum for the peaks indicated by reference numerals 340 and 341 of the GLC profile of FIG. 34 for the compound having the structure:

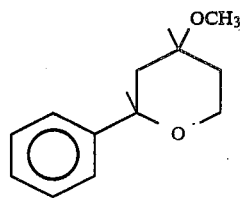

prepared according to Example XVI.

Figures 34, 36:
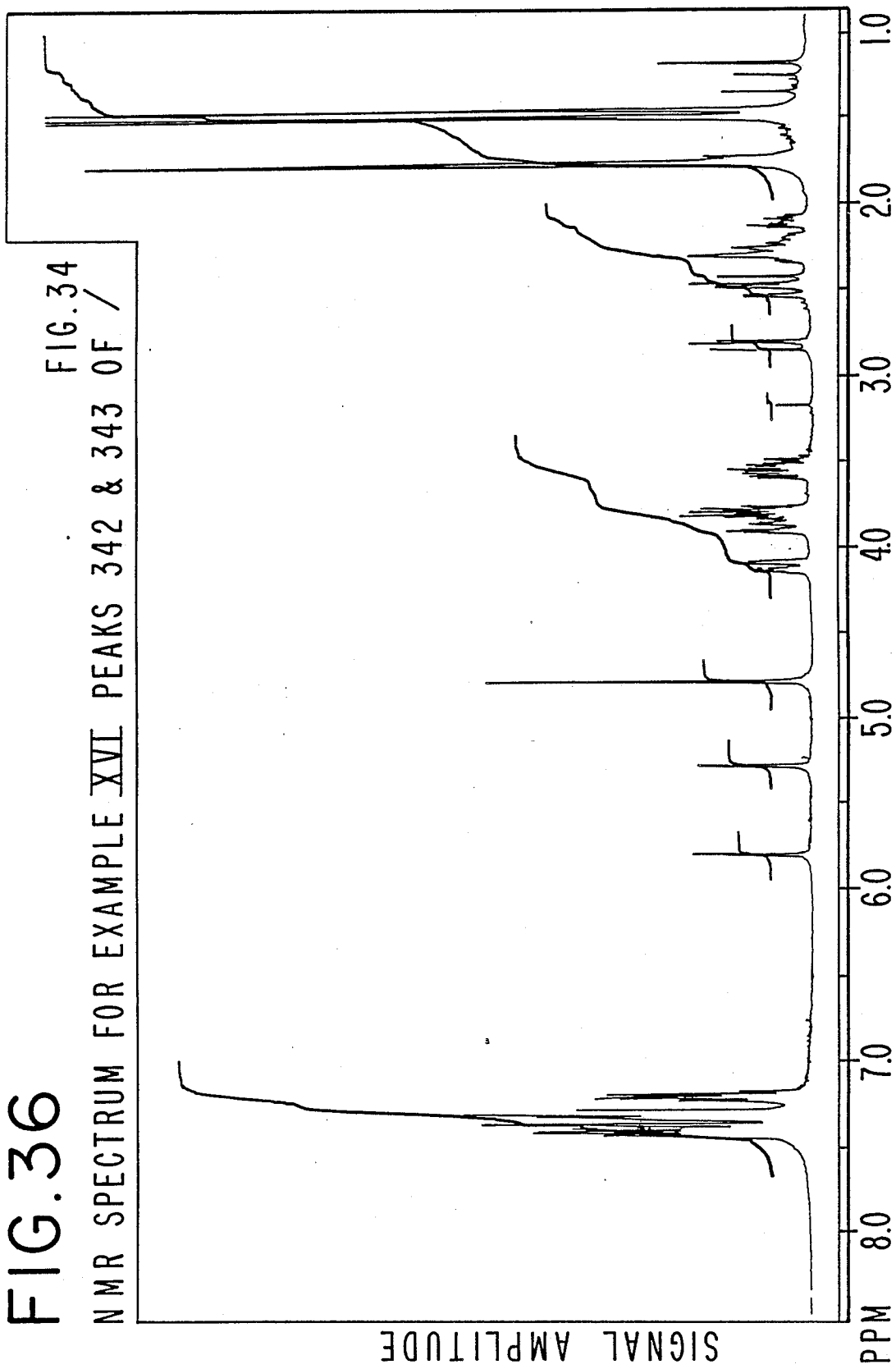

FIG. 36 is the NMR spectrum for the peaks indicated by reference numerals 342 and 343 of the GLC profile of FIG. 34 for the mixture of compounds defined according to the structure:

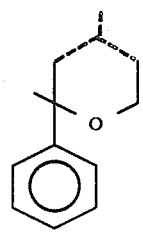

wherein in each of the compounds one of the dashed lines represents a carbon-carbon double bond and each of the other of the dashed lines represent carbon-carbon single bonds.

Figure 37:
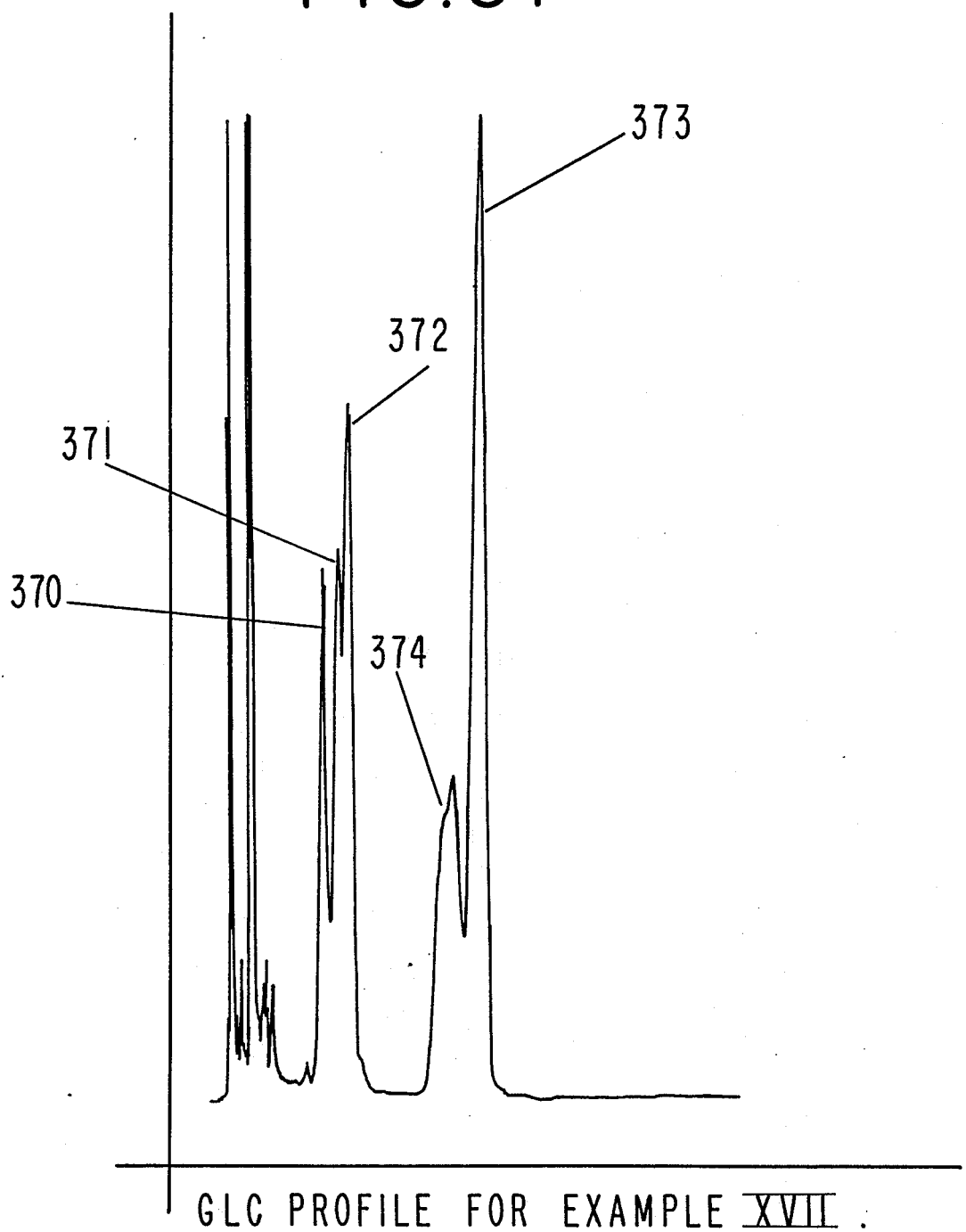

FIG. 37 is the GLC profile for the reaction product of Example XVII containing the compounds having the structures:

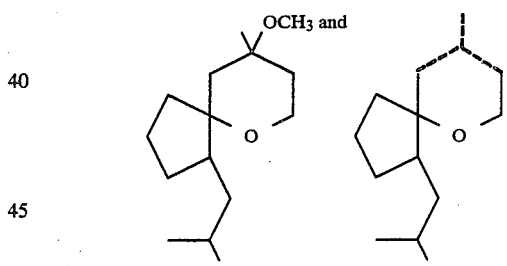

wherein in the compounds having the structures:

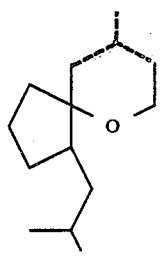

one of the dashed lines represents a carbon-carbon double bond and each of the other of the dashed lines represent carbon-carbon single bonds.

Figure 38:
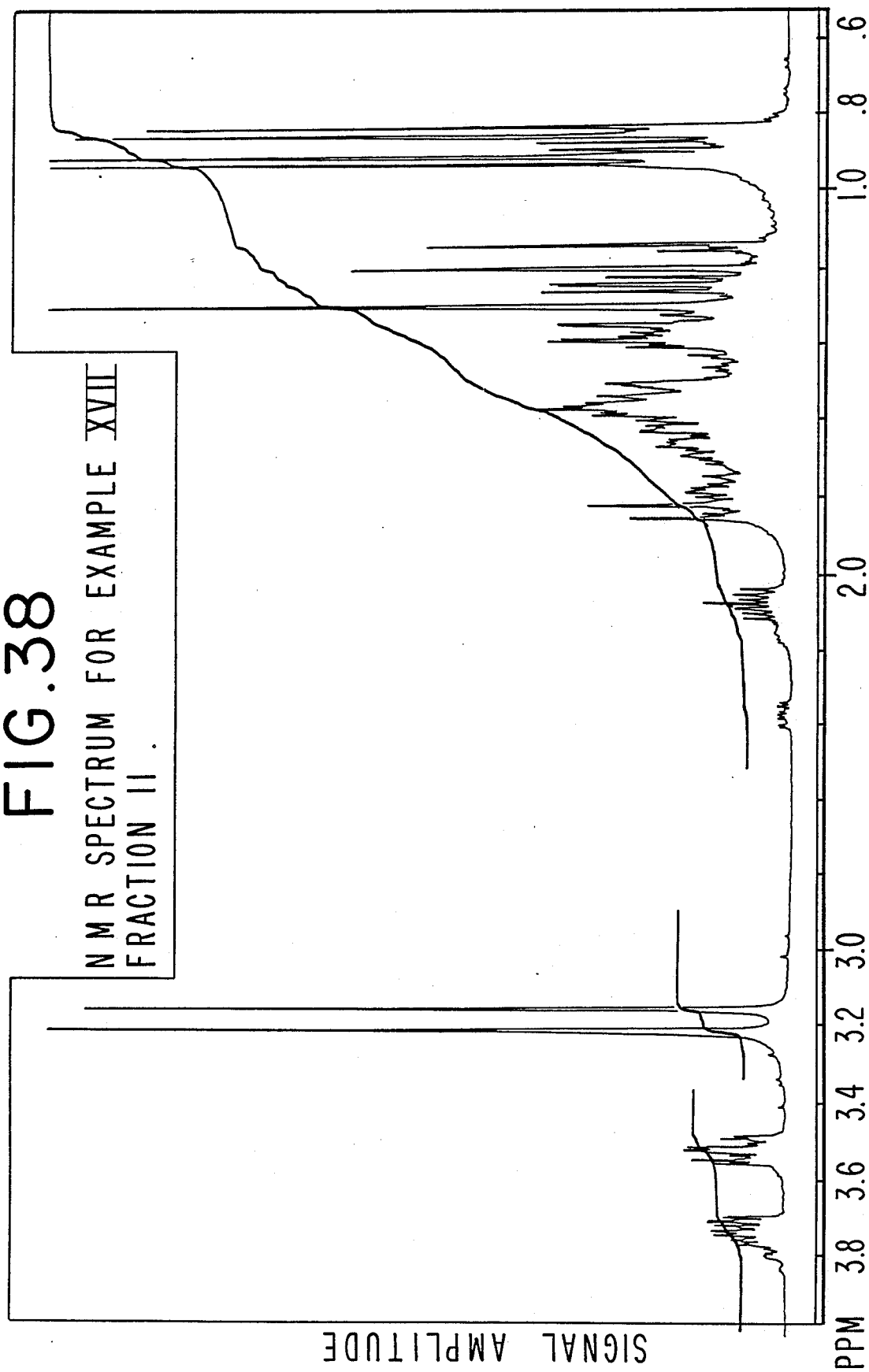

FIG. 38 is the NMR spectrum for Fraction 11 of the distillation product of the reaction product of Example XVII containing the compound having the structure:

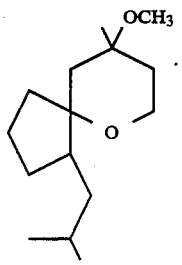

Figure 39:
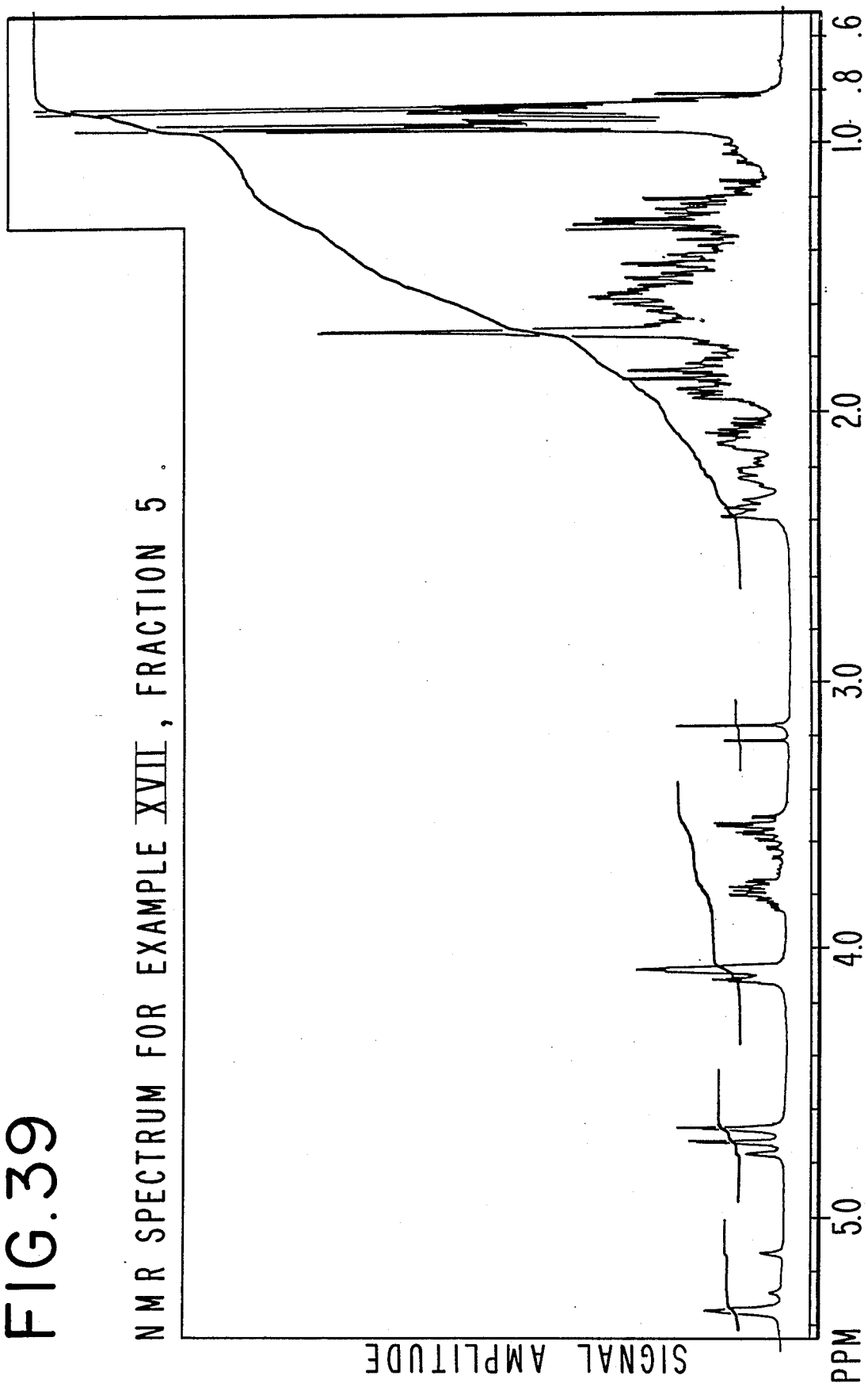

FIG. 39 is the NMR spectrum for Fraction 5 of the distillation product of the reaction product of Example XVII containing the mixture of compounds having the structure:

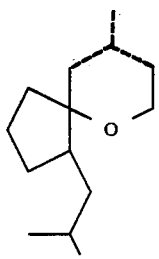

wherein in the mixture in each of the compounds one of the dashed lines represents a carbon-carbon double bond and each of the other of the dashed lines represent carbon-carbon single bonds.

Figure 40:
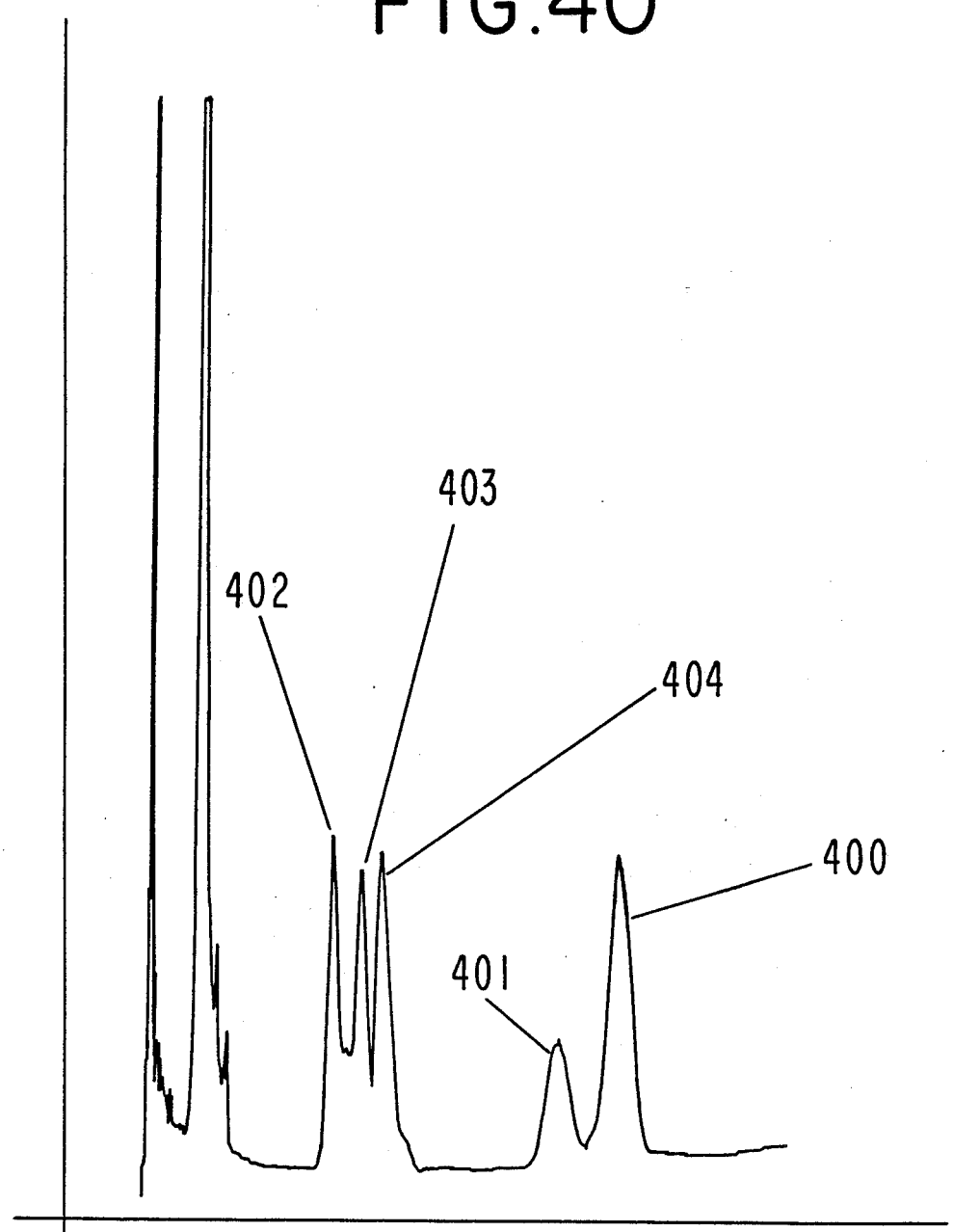

FIG. 40 is the GLC profile for the reaction product of Example XVIII containing the compounds having the structures:

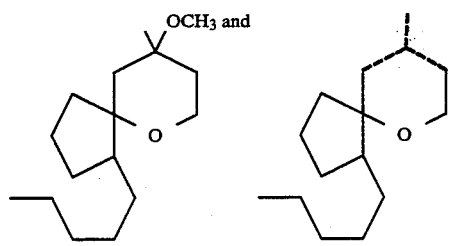

wherein in the compounds having the structure:

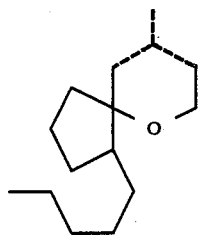

one of the dashed lines represents a carbon-carbon double bond and each of the other of the dashed lines represent carbon-carbon single bonds.

Figure 41:
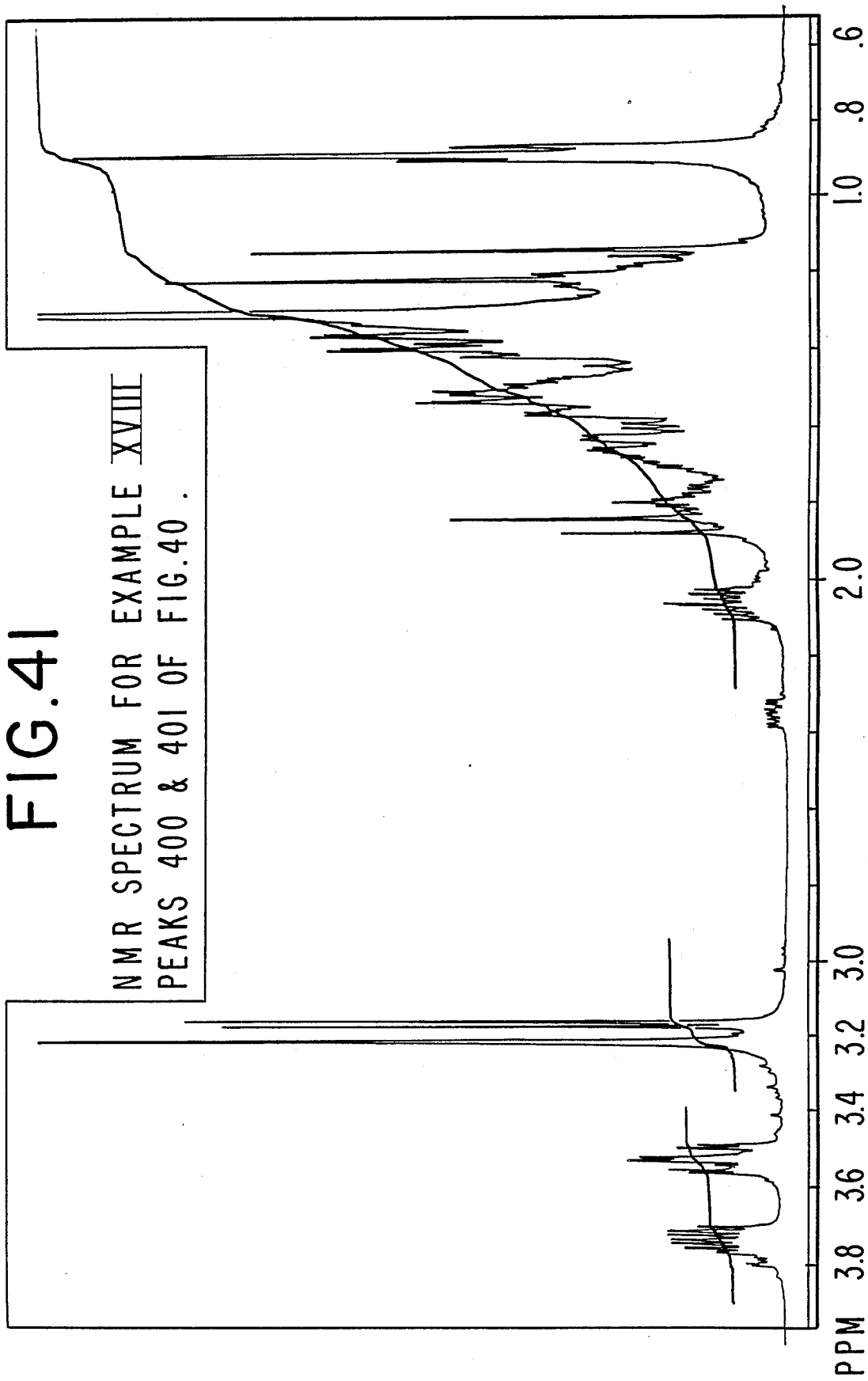

FIG. 41 is the NMR spectrum for peaks 400 and 401 of the GLC profile of FIG. 40 for the compound having the structure:

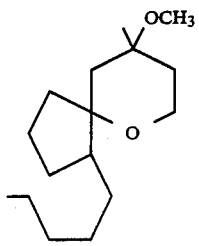

prepared according to Example XVIII.

Figure 42:
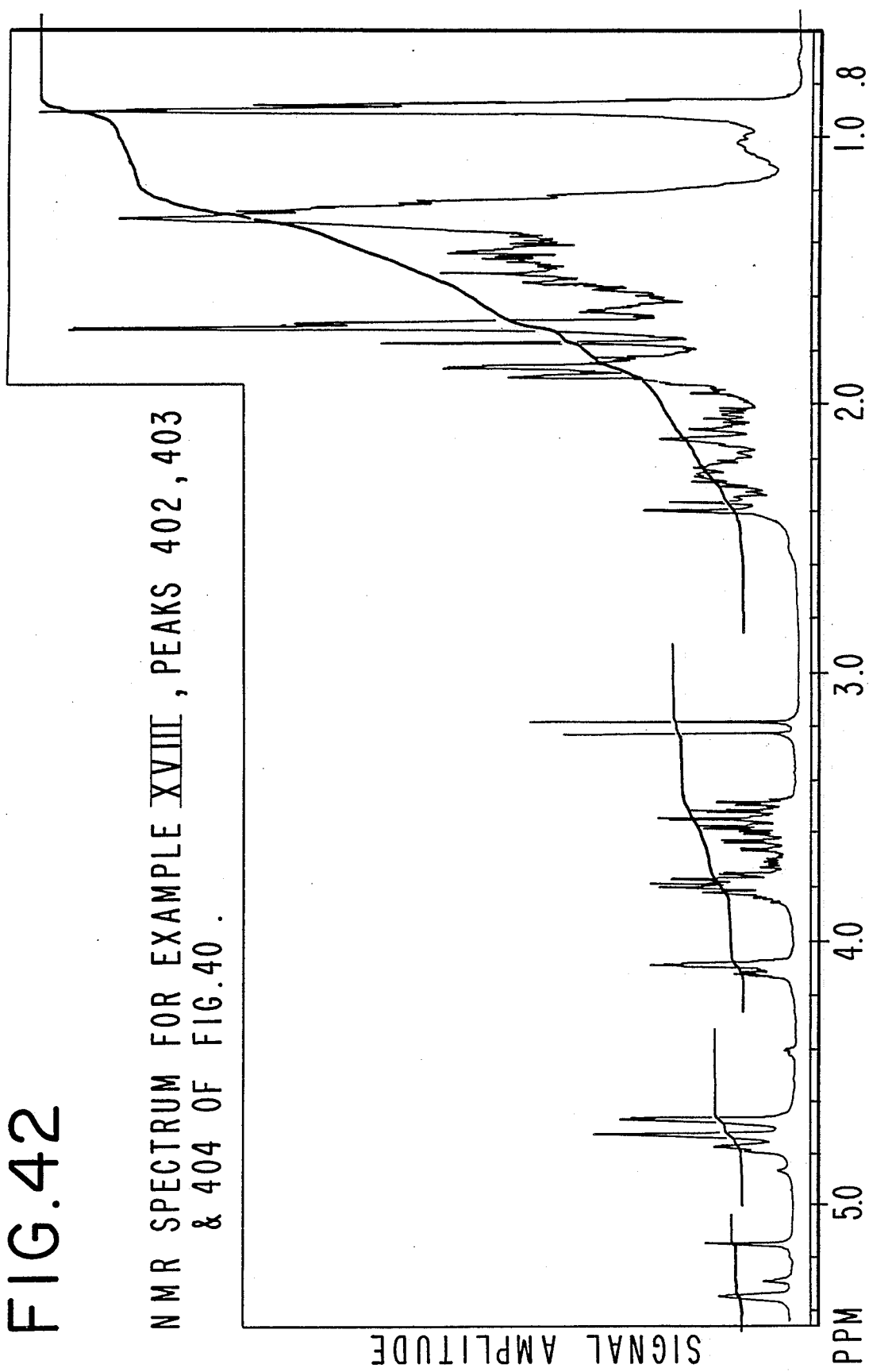

FIG. 42 is the NMR spectrum for the peaks indicated by reference numerals 402, 403 and 404 of the GLC profile of FIG. 40 for the compounds having the structure:

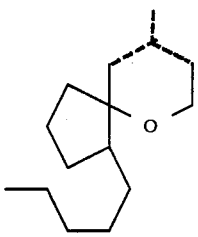

wherein in each of the compounds of the mixture one of the dashed lines represents a carbon-carbon double bond and each of the other of the dashed lines represents a carbon-carbon single bond.

Figure 43:
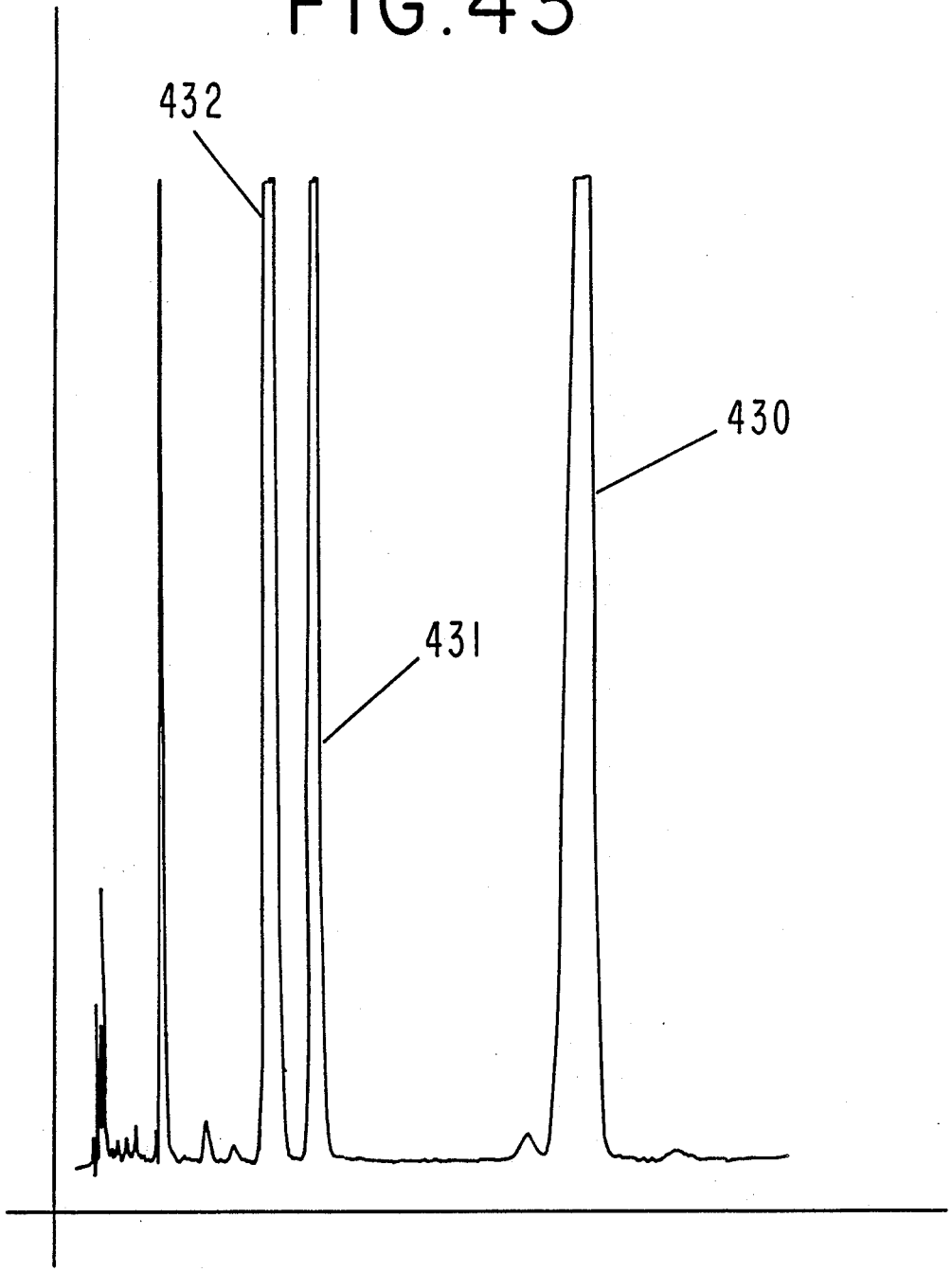

FIG. 43 is a GLC profile for the reaction product of Example XIX containing the compounds having the structures:

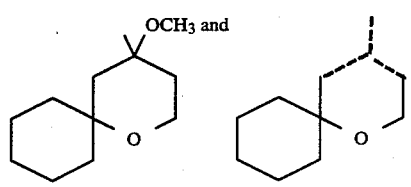

wherein in the compounds having the structure:

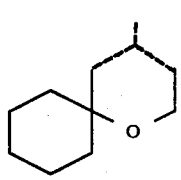

in each of the compounds of the mixture one of the dashed lines represents a carbon-carbon double bond and each of the other of the dashed lines represent carbon-carbon single bonds.

Figure 44:
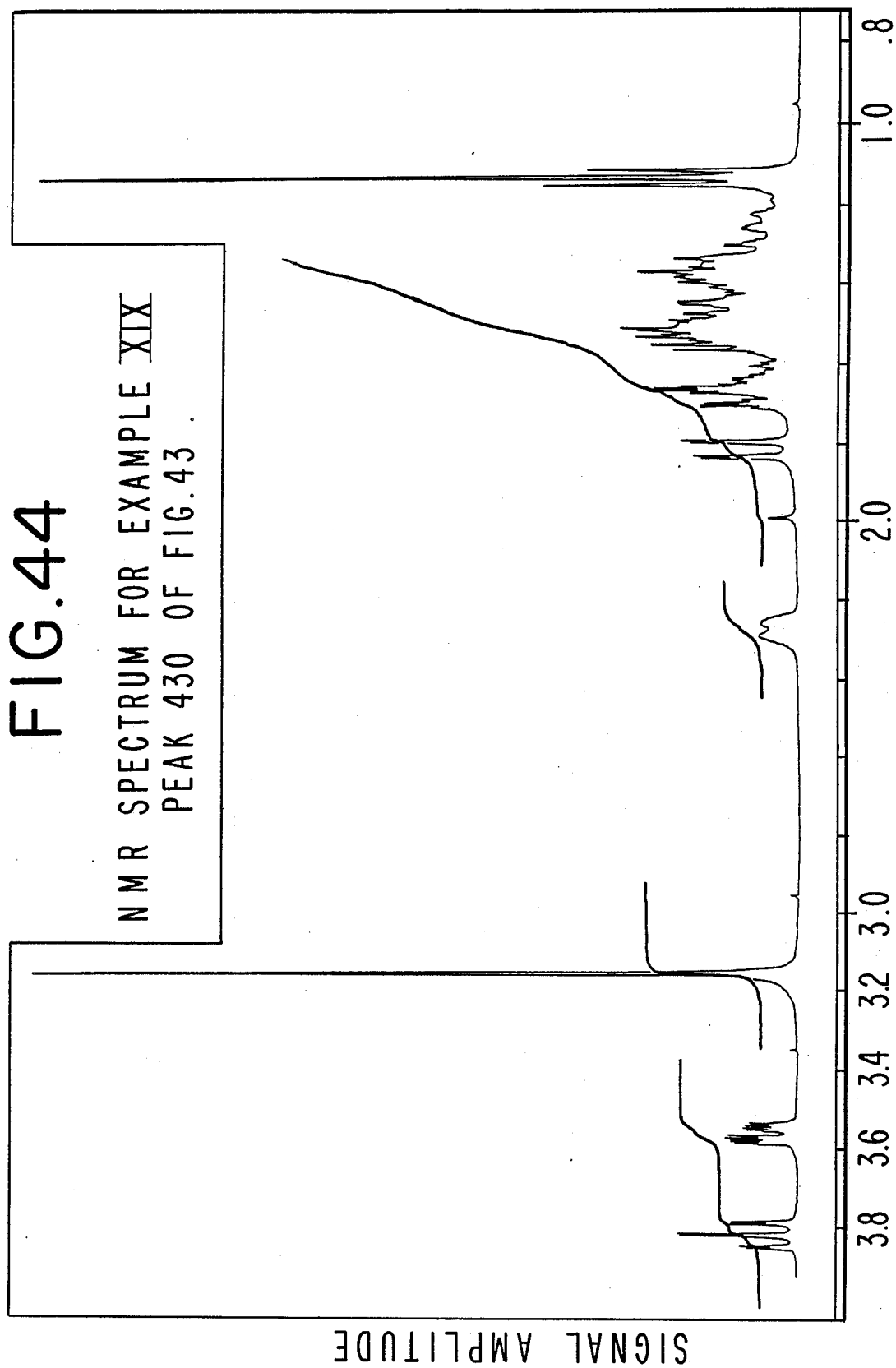

FIG. 44 is the NMR spectrum for the peak indicated by reference numeral 430 of the GLC profile of FIG. 43 and is for the compound having the structure:

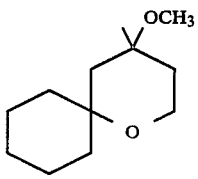

prepared according Example XIX.

Figure 45:
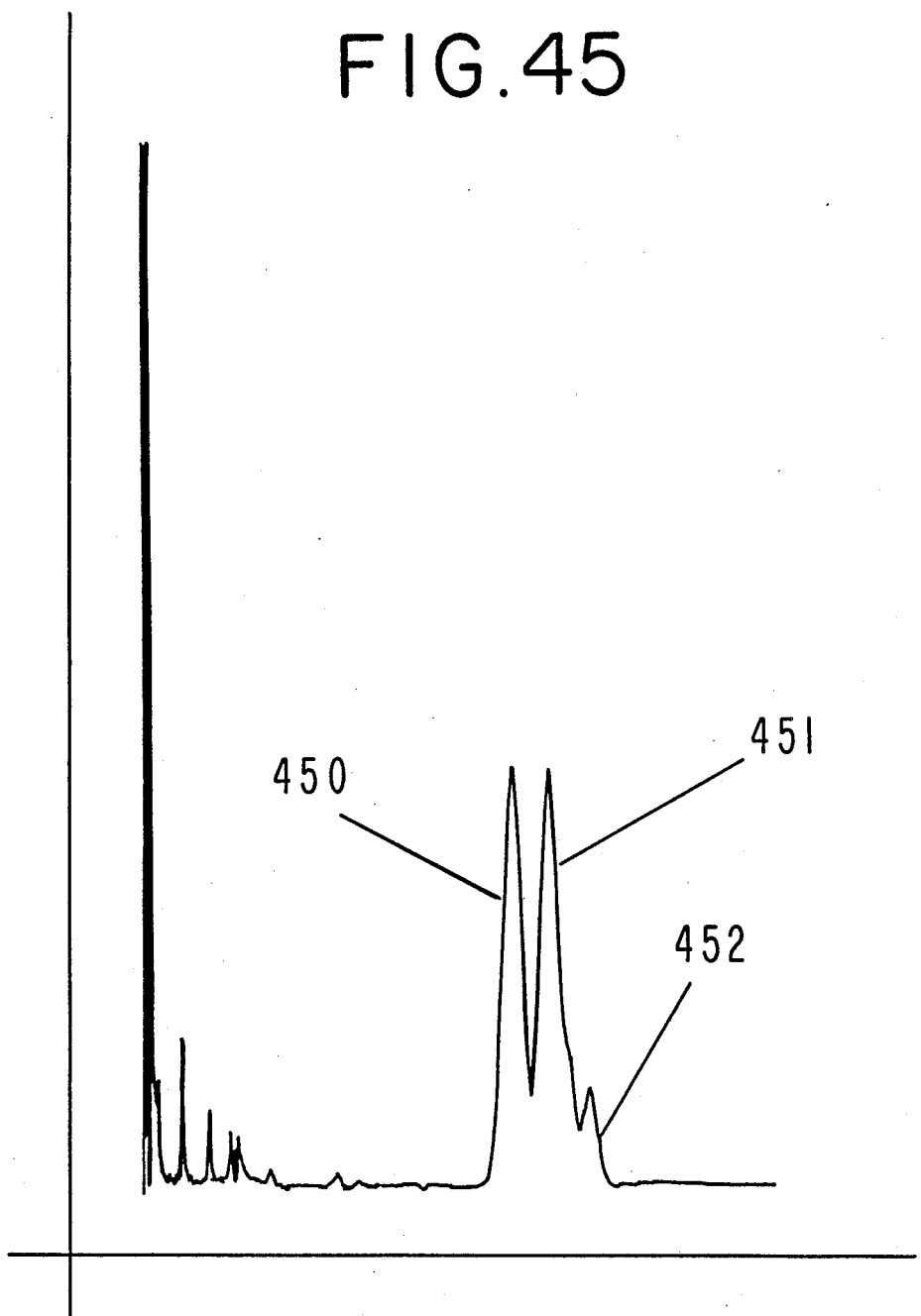

FIG. 45 is the GLC profile for the reaction product of Example XX containing the compounds having the structures:

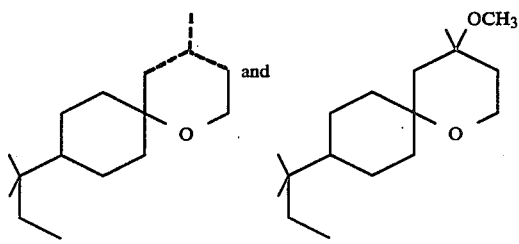

wherein in the compounds have the structure:

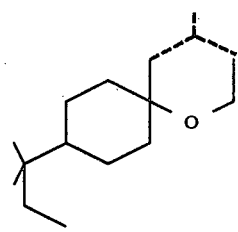

one of the dashed lines represents a carbon-carbon double bond and each of the other of the dashed lines represent carbon-carbon single bonds (Conditions: SE-30 column programmed at 200° C. isothermal).

FIG. 46 is the NMR spectrum for the peaks indicated by reference numerals 450, 451 and 452 of the GLC profile of FIG. 45 for the mixture of compounds having the structure:

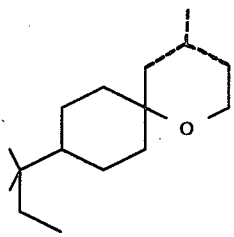

wherein in the mixture in each of the compounds one of the dashed lines represents a carbon-carbon double bond and each of the other of the dashed lines represent carbon-carbon single bonds.

FIG. 47 represents a cut-away side elevation view of apparatus used in forming perfumed polymers which contain imbedded therein at least one of the 2,4-disubstituted and 2,2,4-trisubstituted tetrahydropyranyl-4-ethers of our invention.

FIG. 48 is a front view of the apparatus of FIG. 47 looking in the direction of the arrows.

DETAILED DESCRIPTION OF THE DRAWINGS

Figure 1:
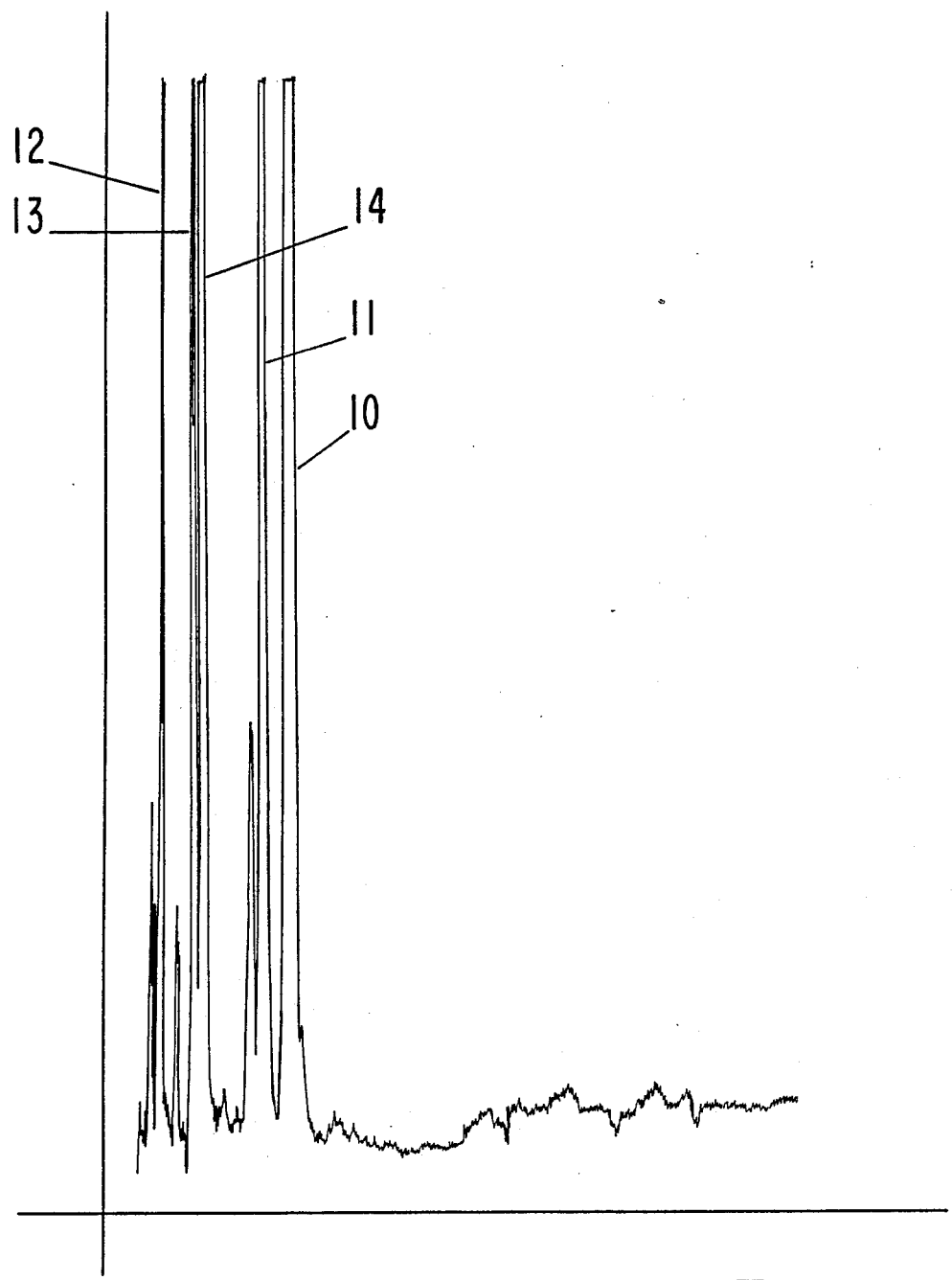
FIG. 1 is the GLC profile for the reaction product of Example I containing compounds having the structures.

FIG. 1 is the GLC profile for the reaction product of Example I. The peaks indicated by reference numerals 10 and 11 are the peaks for the compound having the structure:

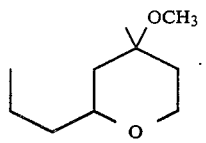

The peaks indicated by reference numerals 12, 13 and 14 are the peaks for the compounds defined according to the generic structure:

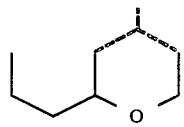

wherein in each of the compounds one of the dashed lines represents a carbon-carbon double bond and each of the other of the dashed lines represent carbon-carbon single bonds.

FIG. 3 is the GLC profile for the reaction product of Example II. The peaks indicated by reference numerals 31 and 32 are for the compound having the structure:

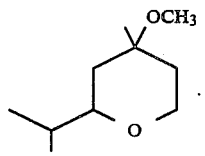

The peaks indicated by reference numerals 33, 34 and 35 are for compounds defined according to the generic structure:

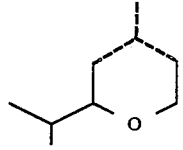

wherein in each of the compounds one of the dashed lines represents a carbon-carbon double bond and each of the other of the dashed lines represent carbon-carbon single bonds.

FIG. 5 is the GLC profile for the reaction product of Example III. The peaks indicated by reference numerals 51 and 52 are for the compound having the structure:

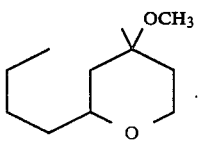

The peaks indicated by reference numerals 53, 54 and 55 are for the compounds represented by the generic structure:

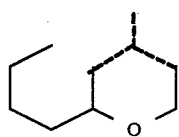

wherein in each of the compounds one of the dashed lines represents a carbon-carbon double bond and each of the other of the dashed lines represent carbon-carbon single bonds.

FIG. 8 is the GLC profile for the reaction product of Example IV. The peaks indicated by reference numerals 81 and 82 are for the compound having the structure:

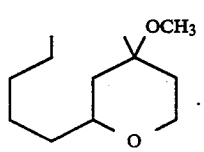

The peaks indicated by reference numerals 83, 84 and 85 are for the compounds defined according to the generic structure:

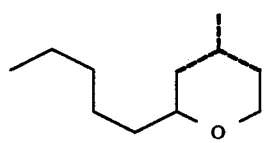

wherein in each of the compounds one of the dashed lines represents a carbon-carbon double bond and each of the other of the dashed lines represent carbon-carbon single bonds.

FIG. 10 is the GLC profile for the reaction product of Example V. The peak indicated by reference numeral 103 is for the compound having the structure:

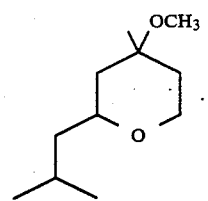

The peaks indicated by reference numerals 100, 101 and 102 are for the compounds defined according to the generic structure:

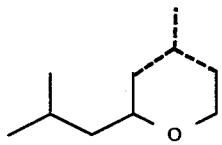

wherein in each of the compounds one of the dashed lines represents a carbon-carbon double bond and each of the other of the dashed lines represent carbon-carbon single bonds.

FIG. 12 is the GLC profile of the reaction product of Example VI. The peaks indicated by reference numerals 121 and 122 are for the compound having the structure:

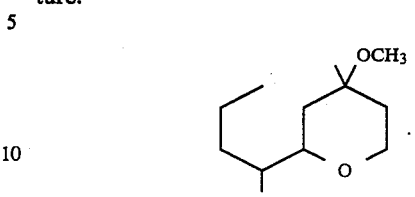

The peaks indicated by reference numerals 123, 124 and 125 are for the compounds of the genus of compounds having the structure:

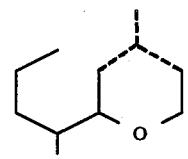

wherein in each of the compounds one of the dashed lines is a carbon-carbon double bond and each of the other of the dashed lines represent carbon-carbon single bonds.

FIG. 14 is the GLC profile for the reaction product of Example VII. The peaks indicated by reference numerals 140 and 141 are for the compound having the structure:

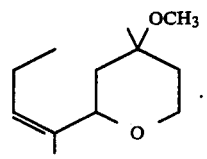

The peaks indicated by reference numerals 142, 143 and 144 are for the members of the genus having the structure:

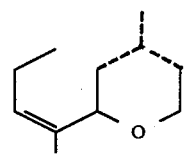

wherein in each of the compounds of the genus one of the dashed lines represents a carbon-carbon double bond and each of the other of the dashed lines represent carbon-carbon single bonds.

FIG. 16 is a GLC profile for the reaction product of Example VIII. The peaks indicated by reference numerals 160 and 161 are for the compound having the structure:

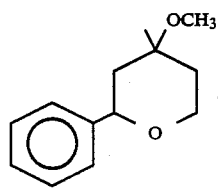

FIG. 18 is the GLC profile for the reaction product of Example IX. The peaks indicated by reference numerals 180 and 181 are for the compound having the structure:

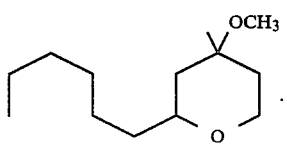

The peaks indicated by reference numerals 182, 183 and 184 are for the members of the genus of compounds having the structure:

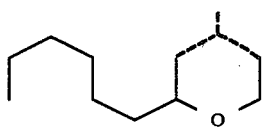

wherein in each of the compounds one of the dashed lines is a carbon-carbon double bond and each of the other of the dashed lines represent carbon-carbon single bonds.

FIG. 20 is the GLC profile for the reaction product of Example X. The peaks indicated by reference numerals 200 and 201 are for the compound having the structure:

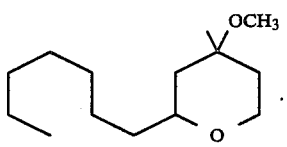

The peaks indicated by reference numerals 202, 203 and 204 are for the members of the genus of compounds having the structure:

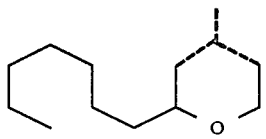

wherein in each of the compounds, one of the dashed lines represents a carbon-carbon double bond and each of the other of the dashed lines represent carbon-carbon single bonds.

FIG. 22 is the GLC profile for the reaction product of Example XI. The peaks indicated by reference numerals 2201 and 2200 are for the compound having the structure:

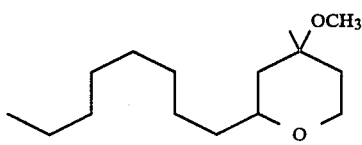

The peaks indicated by reference numerals 2202, 2203 and 2204 are for the members of the genus of compounds having the structure:

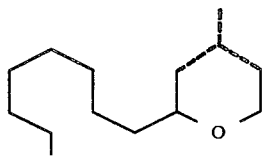

wherein in each of the compounds, one of the dashed lines represents a carbon-carbon double bond and each of the other of the dashed lines represent carbon-carbon single bonds.

FIG. 25 is the GLC profile for the reaction product of Example XII. The peaks indicated by reference numerals 2500 and 2501 are for the compound having the structure:

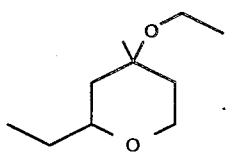

The peaks indicated by reference numerals 2502, 2503 and 2504 are for the members of the genus of compounds having the structure:

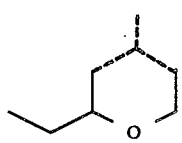

wherein in each of the compounds, one of the dashed lines represents a carbon-carbon double bond and each of the other of the dashed lines represent carbon-carbon single bonds.

FIG. 27 is the GLC profile for the reaction product of Example XIII. The peaks indicated by reference numerals 2700 and 2701 are for the compound having the structure:

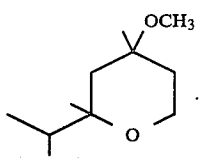

The peaks indicated by reference numerals 2702, 2703 and 2704 are for the members of the genus of compounds having the structure:

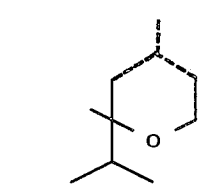

wherein in each of the compounds, one of the dashed lines represents a carbon-carbon double bond and each of the other of the dashed lines represent carbon-carbon single bonds.

FIG. 29 is the GLC profile for the reaction product of Example XIV. The peak indicated by reference numeral 290 is the peak for the compound having the structure:

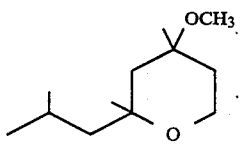

The peaks indicated by reference numerals 291, 292 and 293 are for the compounds defined according to the genus having the structure:

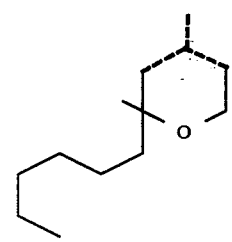

wherein in each of the compounds, one of the dashed lines represents a carbon-carbon double bond and each of the other of the dashed lines represent carbon-carbon single bonds.

FIG. 31 is the GLC profile for the reaction product of Example XV. The peaks represented by the numerals 310 and 311 are for the compound having the structure:

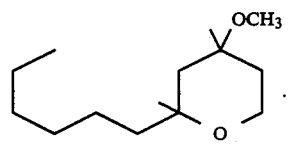

The peaks represented by reference numerals 312, 313 and 314 are for the compounds defined according to the genus:

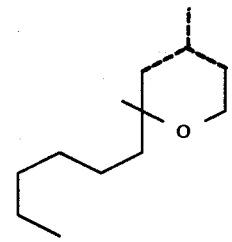

wherein in each of the compounds, one of the dashed lines represents a carbon-carbon double bond and each of the other of the dashed lines represent carbon-carbon single bonds.

FIG. 34 is the GLC profile for the reaction product of Example XVI. The peaks indicated by reference numerals 340 and 341 are for the compound having the structure:

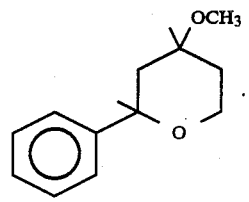

The peaks indicated by reference numerals 342 and 343 are for the members of the genus of compounds having the structure:

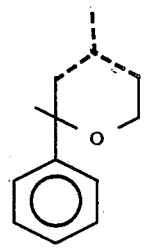

wherein in each of the compounds, one of the dashed lines represents a carbon-carbon double bond and the other two of the dashed lines represent carbon-carbon single bonds.

FIG. 37 is the GLC profile for the reaction product of Example XVII. The peaks indicated by reference numerals 373 and 374 are for the compound having the structure:

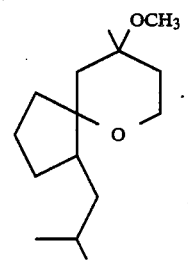

The peaks indicated by reference numerals 370, 371 and 372 are for the members of the genus of the compounds having the structure:

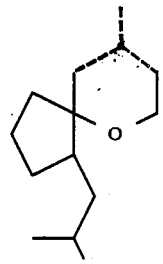

wherein in each of the compounds, one of the dashed lines represents a carbon-carbon double bond and each of the other two dashed lines represent carbon-carbon single bonds.

FIG. 40 is the GLC profile for the reaction product of Example XVIII. The peaks indicated by reference numerals 400 and 401 are for the compound having the structure:

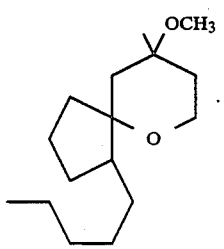

The peaks indicated by reference numerals 402, 403 and 404 are for the members of the genus of compounds having the structure:

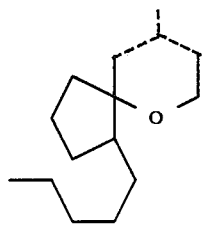

wherein in each of the compound is one of the dashed lines represents a carbon-carbon double bond and each of the other of the dashed lines represent carbon-carbon single bonds.

FIG. 43 is the GLC profile for the reaction product of Example XIX. The peak indicated by reference numeral 430 is the peak for the compound having the structure:

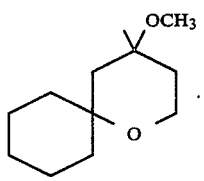

The peaks indicated by reference numerals 431 and 432 are for the members of the genus of compounds having the structure:

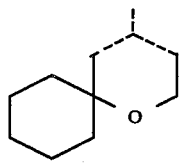

wherein in each of the compounds, one of the dashed lines represents a carbon-carbon double bond and each of the other two of the dashed lines represent carbon-carbon single bonds.

FIG. 45 is the GLC profile for the reaction product of Example XX. The peaks indicated by reference numerals 450, 451 and 452 are for the members of the genus of compounds having the structure:

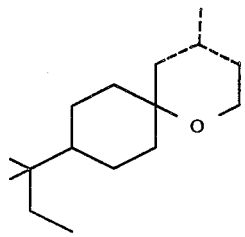

wherein in each of the compounds, one of the dashed lines represents a carbon-carbon double bond and each of the other of the dashed lines represents a carbon-carbon signal bond.

Referring to FIGS. 47 and 48, there is provided a process for forming scented polymer elements (wherein the polymer may be a thermoplastic polymer such as low density polyethylene or polypropylene or copolymers of ethylene and vinyl acetate or mixtures of polymers and copolymers such as copolymers of ethylene and vinyl acetate and polyethylene) such as pellets useful in the formation of plastic particles useful in fabricating certain articles which ay be perfumed (and, further, which may be exposed to chlorine bleaches). This process comprises heating the polymer or mixture of polymers to the melting point of said polymer or mixture of polymers, e.g., 250° C. in the case of low density polyethylene. The lower most portion of the container is maintained at a slightly lower temperature and the material in the container is taken off at such location for delivery through the conduit. Thus, referring to FIGS. 47 and 48, in particular, the apparatus used in producing such elements comprises a device for forming the polymer containing the perfume, e.g., polyethylene or polyethylene-polyvinyl acetate or mixtures of same or polyproylene, which comprises a vat or container 212 into which the polymer taken alone or in admixture with other copolymers and the perfuming substance which is at least one of the 2,4-disubstituted and 2,2,4-trisubstituted tetrahydropyranyl-4-ethers of our invention and other compatible perfumes is placed. The container is closed by means of an air-tight lid 228 and clamped to the container by bolts 265. The stirrer 273 traverses the lid or cover 228 in an air-tight manner and is rotatable in a suitable manner. A surrounding cylinder 212A having heating coils which are supplied with electric current through cable 214 from a rheostat or control 216 is operated to maintain the temperature inside the container 212 such that the polymer in the container will be maintained in the molten or liquid state. It has been found advantageous to employ polymers at such a temperature that the viscosity will be in the range of 90–100 sayboldt seconds. The heater 218 is operated to maintain the upper portion of the container 212 within a temperature range of, for example, 220°–270° C. in the case of low density polyethylene.

The bottom portion of the container 212 is heated by means of heating coils 212A regulated through the control 220 connected thereto through a connecting wire 222 to maintain the lower portion of the container 212 within a temperature range of 220°–270° C.

Thus, the polymer or mixture of polymers added to the container 212 is heated from 10–12 hours, whereafter the perfume composition or perfume material which contains one or more of the 2,4-disubstituted and 2,2,4-trisubstituted tetrahydropyranyl-4-ethers of our invention is quickly added to the melt. Generally, about 10-45 percent by weight of the resulting mixture of the perfumery substance is added to the polymer.

After the perfume material is added to the container 212, the mixturee is stirred for a few minutes, for example, 5-15 minutes and maintained within the temperature ranges indicated previously by the heating coil 212A. The controls 216 and 220 are connected through cables 224 and 226 to a suitable supply of electric current for supplying the power for heating purposes.

Thereafter, the valve "V" is opened permitting the mass to flow outwardly through conduit 232 having a multiplicity of orifices 234 adjacent to the lower side thereof. The outer end of the conduit 232 is closed so that the liquid polymer in intimate admixture with one or more of the 2,4-disubstituted and 2,2,4-trisubstituted tetrahydropyranyl-4-ethers of our invention and one or more other substances, will continuously drop through the orifices 234 downwardly from the conduit 232. During this time, the temperature of the polymer intimately admixed with the perfumery substance in the container 212 is accurately controlled so that a temperature in the range of from about 240°-250° C., for example, (in the case of low density polyethylene) will exist in the conduit 232. The regulation of the temperature through the controls 216 and 220 is essential in order to insure temperature balance to provide for the continuous dripping or dropping of molten polymer intimately admixed with the perfume substance which is all of or which contains one or more of the 2,4-disubstituted and 2,2,4-trisubstituted tetrahydropyranyl-4-ethers of our invention, through the orifices 234 at a rate which will insure the formation of droplets 236 which will fall downwardly onto a moving conveyor belt 238 caused to run between conveyor wheels 240 and 242 beneath the conduit 232.

When the droplets 236 fall onto the conveyor 238, they form pellets 244 which harden almost instantaneously and fall off the end of the conveyor 238 into a container 250 which is advantageously filled with water or some other suitable cooling liquid to insure the rapid cooling of each of the pellets 244. The pellets 244 are then collected from the container 250 and utilized for the formation of functional products, e.g., garbage bags and the like.

THE INVENTION

The present invention provides 2,4-disubstituted and 2,2,4-trisubstituted tetrahydropyranyl-4-ethers defined according to the structure:

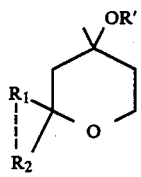

wherein R' represents methyl or ethyl and $R_1$ and $R_2$ taken alone are the same or different hydrogen, phenyl, $C_1-C_8$ alkyl or $C_2-C_8$ alkenyl (with the proviso that $R_1$ and $R_2$ are not both hydrogen) and $R_1$ and $R_2$ taken together are a $C_5-C_{12}$ cycloalkyl or alkyl cycloalkyl moiety. The present invention also provides mixtures of such 2,4-disubstituted and 2,2,4-trisubstituted tetrahydropyranyl-4-ethers with compounds having the structure:

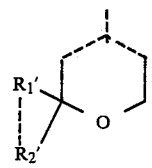

wherein $R_1'$ and $R_2'$ are the same as $R_1$ and $R_2$ defined, supra, and the moiety:

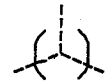

causes the structure:

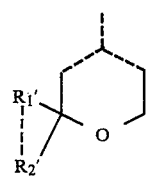

to represent a mixture wherein in the mixture, one of the dashed lines represents a carbon-carbon double bond and each of the other of the dashed lines in each of the compounds of the mixture represents a carbon-carbon single bond.

The 2,4-disubstituted and 2,2,4-trisubstituted tetrahydropyranyl-4-ethers of our invention may be produced according to three process steps:

(a) first reacting an aldehyde or a ketone with a reagent for effecting acetal or ketal formation according to the reaction:

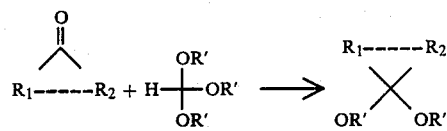

(b) then reacting the thus-formed ketal or acetal with prenyl alcohol according to the reaction:

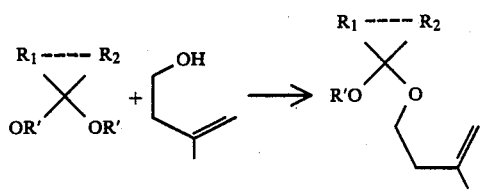

(c) the thus-formed prenyl acetal or ketal then rearranges to form a composition of matter containing the 2,4-disubstituted and 2,2,4-trisubstituted tetrahydropyranyl-4-ethers of our invention, thusly:

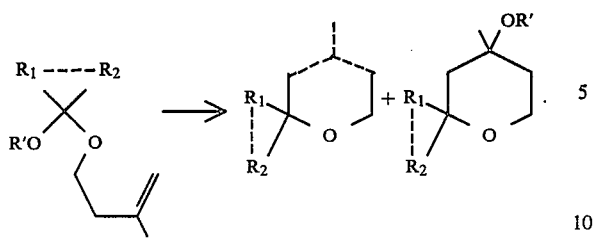

The mechanisms of the reaction whereby the prenyl alcohol is first reacted with the ketal or acetal and the resulting prenyl acetal or ketal is rearranged is as follows:

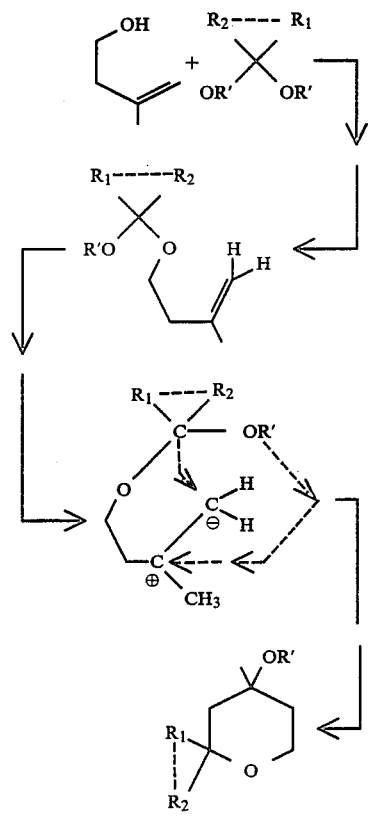

The aforementioned reaction between the prenyl alcohol and the acetal or ketal having the structure:

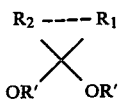

and resultant rearrangement is carried in the presence of from about 1% up to about 5% by weight of the reaction mass of a protonic acid, preferably sulfuric acid. The mole ratio of prenyl alcohol having the structure:

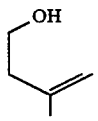

to acetal or ketal having the structure:

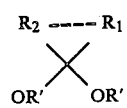

is preferably about 1:1. The reaction temperature may range from about 50° C. up to about 100° C. with a preferred reaction temperature of about 80° C.

At the end of the reaction, the reaction mass is fractionally distilled and, if desired, (from an organoleptic standpoint) the group of compounds having the structure:

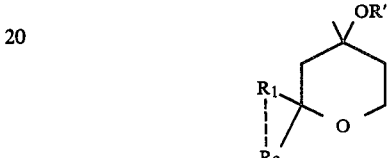

may be separated by means of distillation from the group of compounds having the structure:

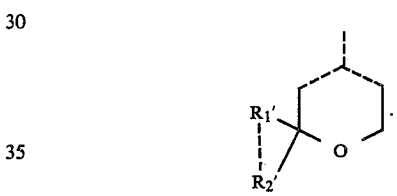

An alternative route to form the compounds having the structure:

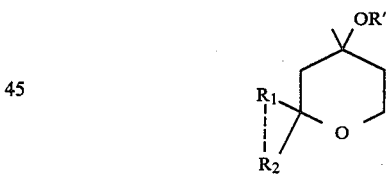

is to react the corresponding alcohols with an etherifying reagent such as dimethyl sulfate according to the reaction:

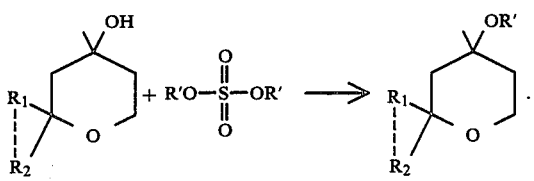

The pyranol reactants for the foregoing reaction may be produced using conditions as set forth in the prior art, for example, conditions set forth in USSR Patent No. 620,487 by means of reacting an aldehyde or a ketone with prenyl alcohol according to the reaction:

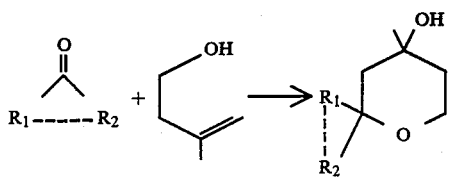

in the presence of an acid catalyst such as an inorganic acid or an acid anion exchange catalyst or phosphoric acid or sulfuric acid at a temperature in the range of from about 50 up to about 60° C. Examples of such reactions in the prior art to form pyranols are as follows:

(a) the reaction:

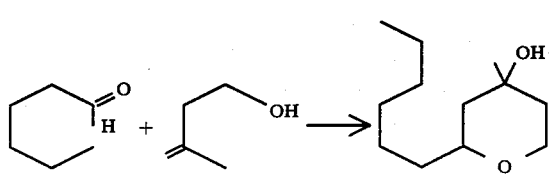

set forth in U.S.S.R. Patent 620,487;

(b) the reaction:

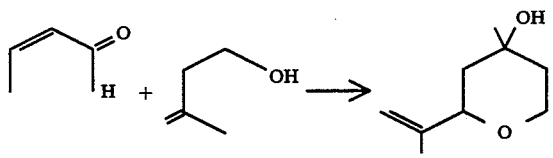

set forth in U.S.S.R. Patent 638,597.

Specific examples of the 2,4-disubstituted and 2,2,4-trisubstituted tetrahydropyranyl-4-ethers produced according to the foregoing processes and useful in the practice of our invention and their organoleptic properties are set forth in Table I below:

TABLE I

| Structure of Compound | Perfumery Evaluation |
|---|---|
| The compound having the structure: (Example I) | A green, herbaceous, parsley, rose, fruity, spicy, earthy and rooty aroma profile |
| The compound having the structure: (Example II) | A sauge sclaree, minty and woody aroma. |
| The compound having the structure: (continued) | A fruity, herbaceous, celery-like, citrusy |

TABLE I-continued

| Structure of Compound | Perfumery Evaluation |
|---|---|
| (Example III) | aroma with fruity, floral, jasmine, lily of the valley, green and herbaceous undertones. |
| The compound having the structure: (Example IV) | A fresh, clean, tangeine-like, fruity, jasmine aroma with galbanum, jasmine, celery-like, green and pineapple topnotes. |
| The compound having the structure (Example V) | A green, herbaceous, woody, aroma with floral undertones. |
| The compound having the structure (Example VI) | A spicy, dill, caraway, herbaceous aroma animalic, dill and caraway undertones. |
| The compound having the structure: (Example VII) | A nutty, coconut aroma with cinnamon and pineapple topnotes and floral, herbaceous undertones. |
| The compound having the structure (Example VIII) | A spicy aroma with oak moss topnotes |
| The compound having the structure: | A fruity, herbaceous, floral aroma with |

TABLE I-continued

| Structure of Compound | Perfumery Evaluation |
|---|---|
| produced according to Example IX. | citrusy, herbaceous and floral undertones. |
| The compound having the structure: produced according to Example X. | A fruity, peach and coconut-like aroma with almond oil topnotes. |
| The compound having the structure: produced according to Example XI. | A fresh, ozoney, seashore, aroma with animalic topnotes. |
| The compound having the structure: produced according to Example XII. | A caramel, maple syrup aroma with green, herbaceous topnotes. |
| The compound having the structure: produced according to Example XIII. | A minty, woody, green, herbaceous aroma with camphoraceous, eucalyptus-like topnotes. |
| The compound having the structure: produced according to Example XIV. | A citrusy, grapefruit, nootkatone-like aroma |
| The compound having the structure: produced according to Example XV. | A green, herbaceous, aroma with animalic undertones. |
| The compound having | A new moun hay aroma with green, herbaceous, straw-like undertones. |
| the structure: produced according to Example XVI. | |
| The compound having the structure: produced according to Example XVII. | A jasmine aroma. |
| The compound having the structure: produced according to Example XVIII. | A fruity, peach-like, apricot and jasmine aroma profile. |
| The compound having the structure: produced according to Example XIX. | A woody, citrusy, mandarine orange peel-like, floral, herbaceous and basil aroma with sweet citrus, bergamot and floral undertones. |
| The compound having the structure: prepared according to Example XX. | A herbaceous, plum aroma with fresh, ozoney undertones. |

The 2,4-disubstituted and 2,2,4-trisubstituted tetrahydropyranyl-4-ethers of our invention and one or more auxiliary perfume ingredients, including, for example, hydrocarbons, alcohols, ketones, aldehydes, nitriles, esters lactones, ethers other than the 2,4-disubstituted and 2,2,4-trisubstituted tetrahydropyranyl-4-ethers of our invention, hydrocarbons, synthetic essential oils and natural essential oils may be admixed so that the combined odors of the individual components produce a pleasant and desired fragrance, particularly and preferably in the citrusy and/or herbaceous and/or woody and/or piney and/or earthy fragrances.

Such perfume compositions usually contain (a) the main note or the "bouquet" or foundation stone of the composition; (b) modifiers which round off and accompany the main note; (c) fixatives which include odorous substances which lend a particular note to the perfume throughout all stages of evaporation and substances which retard evaporation; and (d) topnotes which are usually low boiling fresh smelling materials.

In perfume compositions, it is the individual components which contribute to their particular olfactory characteristics; however the overall sensory effect of the perfume composition will be at least the sum total of the effects of each of the ingredients. Thus, one or more of the 2,4-disubstituted and 2,2,4-trisubstituted tetrahydropyranyl-4-ethers of our invention can be used to alter, modify or enhance the aroma characteristics of a perfume composition, for example, by utilizing or moderating the olfactory reaction contributed by another ingredient in the composition.

The amount of one or more of the 2,4-disubstituted and 2,2,4-trisubstituted tetrahydropyranyl-4-ethers of our invention which will be effective in perfume compositions as well as in perfumed articles and colognes depends upon many factors, including the other ingredients, their amounts and the effects which are desired. It has been found that perfume compositions containing as little as 0.005% of the 2,4-disubstituted and 2,2,4-trisubstituted tetrahydropyranyl-4-ethers of our invention or even less (e.g., 0.002%) can be used to impart, augment or enhance green, herbaceous, basil, parsley, rose, fruity, mandarin orange peel, spicy, earthy, rooty, sauge sclaree, minty, woody, celery-like, citrusy, seashore, fresh, clean, ozoney, tangerine-like, grapefruit-like, Nootkatone-like, jasmine, dill, caraway, nutty, coconut, floral, peach-like, apricot-like, caramel-like, maple syrup and new moun hay aroma profiles with galbanum, jasmine, celery-like, green, cinnamon, pineapple, oak moss, almond oil, animalic, herbaceous, camphoraceous and eucalyptus-like topnotes and fruity, floral, jasmine, lily of the valley, green, herbaceous, animalic, dill, caraway, citrusy, sweet citrus, straw-like and bergamot undertones to soaps, cosmetics, detergents (including anionic, cationic, nonionic or zwitterionic solid or liquid detergents) or other products. The amount employed can range up to 70% of the fragrance components and will depend upon considerations of cost, nature of the end product, the effect desired on the finished product and the particular fragrance sought.

The 2,4-disubstituted and 2,2,4-trisubstituted tetrahydropyranyl-4-ethers of our invention are useful (taken alone or together with other ingredients in perfume compositions) in detergents and soaps, space odorants, perfumes, colognes, toilet water, bath preparations such as lacquers, brilliantines, pomades and shampoos; cosmetic preparations, such as creams, deodorants, hand lotions and sun screens; powders such as talcs, dusting powders, face powders and the like. As little as 0.25% of the 2,4-disubstituted and 2,2,4-trisubstituted tetrahydropyranyl-4-ethers of our invention will suffice to impart an intense and long-lasting green, herbaceous, basil, parsley, rose, fruity, mandarin orange peel, spicy, earthy, root, sauge sclaree, minty, woody, celery-like, citrusy, seashore, fresh, clean, ozoney, tangerine-like, grapefruit-like, Nootkatone-like, jasmine, dill, caraway, nutty, coconut, floral, peach-like, apricot-like, caramel-like, maple syrup and new moun hay aromas with galbanum, jasmine, celery-like, green, cinnamon, pineapple, oak moss, almond oil, animalic, herbaceous, camphoraceous and eucalyptus-like topnotes and with fruity, floral, jasmine, lily of the valley, green, herbaceous, animalic, dill, caraway, citrusy, sweet citrus, straw-like and bergamot undertones to citrusy, woody, floral, herbaceous and earthy perfume formulations. Generally, no more than 5% of the 2,4-disubstituted and 2,2,4-trisubstituted tetrahydropyranyl-4-ethers of our invention based on the ultimate end product is required to be used as is or in perfume compositions.

Furthermore, as little as 0.25% of the 2,4-disubstituted and 2,2,4-trisubstitued tetrahydropyranyl-4-ethers of our invention will suffice to impart such aroma to perfumed articles per se, whether in the presence of other perfume materials or whether used by themselves. Thus, the range of use of the 2,4-disubstituted and 2,2,4-trisubstituted tetrahydropyranyl-4-ethers of our invention in perfumed articles may vary from about 0.25% up to about 5% by weight based on the total weight of the perfumed article.

In addition, the perfume composition or fragrance composition of our invention can contain a vehicle or carrier for the 2,4-disubstituted and 2,2,4-trisubstituted tetrahydropyranyl-4-ethers of our invention. The vehicle can be a liquid such as a non-toxic alcohol, e.g., ethanol, a non-toxic glycol, e.g., propylene glycol or the like. The carrier can also be an absorbent solid, such as a gum (e.g., gum arabic), or components for encapsulating the composition by means of coacervation (such as gelatin).

It will thus be apparent that the 2,4-disubstituted and 2,2,4-trisubstituted tetrahydropyranyl-4-ethers of our invention can be utilized to alter, modify or enhance the aroma of perfume compositions, colognes or perfumed articles.

Furthermore, several processes may be used in order to produce a thickened, highly viscous hypochlorite bleaching or sterilizing solution whereby the desired aroma profiles are imparted to the articles treated with said hypochlorite solutions.

Thus, for example, the 2,4-disubstituted and 2,2,4-trisubstitued tetrahydropyranyl-4-ethers of our invention may be premixed with the diphenyl oxide derivative or diphenyl oxide derivative-amine oxide solubilizer-stabilizer (having the structures, respectively:

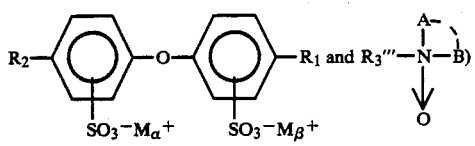

and the resulting 2,4-disubstituted and 2,2,4-trisubstituted tetrahydropyranyl-4-ethers/diphenyl oxide derivative or 2,4-disubstituted and 2,2,4-trisubstituted tetrahydropyranyl-4-ethers-diphenyl oxide derivative-amine oxide premix is then mixed with the hypochlorite bleaching or sterilzing solution with stirring. Immediately after such addition, an aqueous alkali metal hydroxide solution is added to the mixture to bring the pH to the range of 11–14.0. A pH of less than 11 is not desired since it is difficult to achieve a single phase stable system at low pH's. A pH higher than 14.0 will also create a system which (1) is unnecessarily corrosive; (2) will narrow the range of perfume oils useable (in conjunction wit the 2,4-disubstituted and 2,2,4-trisubstituted tetrahydropyranyl-4-ethers) of the system and (3) will limit the particular ingredients useable in such perfume oils in conjunction with the 2,4-disubstituted and 2,2,4-trisubstituted tetrahydropyranyl-4-ethers. On the other hand, if for example, the 2,4-disubstituted and 2,2,4-trisubstituted tetrahydropyranyl-4-ethers is used alone or further in combination with (i) diisoamylene epoxides; (ii) diisoamylenes as described in application for U.S. Letters Patent, Ser. No. 188,576 filed on Oct. 9, 1980; or (iii) acyl diisoamylene derivatives described in application for U.S. Letters Patent, Ser. No. 184,132 filed on Sept. 4, 1980 and/or (iv) ketal derivatives of acyl diisoamylene derivatives described in application for U.S. Letters Patent, Ser. No. 212,993 filed on Dec. 4, 1980, a pH of about 14.0 and even slightly higher (e.g., 14.1) is acceptable.

The aqueous alkali metal hydroxide can be added to the aqueous alkali metal hypochlorite solution before adding the diphenyl oxide derivatives (taken alone or in conjunction with the amine oxide) or the 2,4-disubstituted and 2,2,4-trisubstituted tetrahydropyranyl-4-ethers or mixtures of 2,4-disubstituted and 2,2,4-trisubstituted tetrahydropyranyl-4-ethers with other materials such as diisoamylene epoxides. Indeed, the ingredients: the 2,4-disubstituted and 2,2,4-trisubstituted tetrahydropyranyl-4-ethers; the alkali metal hydroxide and the diphenyl oxide derivative or diphenyl oxide derivative-amine oxide composition (having the structures, respectively:

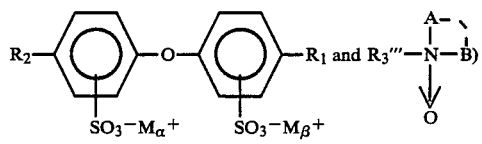

may be added or admixed in any order which is convenient to the formulator. One desirable process involves first forming the diphenyl oxide derivative or diphenyl oxide derivative-amine oxide composition-2,4-disubstituted and 2,2,4-trisubstituted tetrahydropyranyl-4-ethers "premix", mixing the premix with the alkali metal hypochlorite solution and finally adjusting the pH of the solution with alkali metal hydroxide to bring the pH to within the range of 11–14.0. A second, more preferable process, involves first adjusting the pH of the aqueous alkali metal hypochlorite solution to 11–14.0 and then admixing the solution with the aforedescribed "premix".

The alkali metal hypochlorites preferred in the practice of our invention are: sodium hypochlorite, potassium hypochlorite and lithium hypochlorite or mixtures of same. The alkali metal hypochlorites preferred in the practice of this invention are: lithium hydroxide, potassium hydroxide and sodium hydroxide, or, if desired, mixtures of such hydroxides.

The temperature at which the composition of our invention remains both substantially stable and commercially useful for the purposes set forth herein (that is, remains as a clear single aqueous or gel phase) and retains (1) the desired properties inherent in the known bleaching and sterilizing uses of aqueous alkali metal hypochlorite liquid or gel solutions, and (2) the properties imparted thereto as a result of the use of the 2,4-disubstituted and 2,2,4-trisubstituted tetrahydropyranyl-4-ethers which impart to articles previously subjected to the aqueous alkali metal hypochlorite gel or liquid solutions a desired aroma profile, varies from approximately 20° F. up to approximately 120° F. At temperatures below 20° F. a two-phase system usually occurs and at temperatures higher than 120° F. the bleaching or sterilizing efficiency of the compositions of our invention is diminished at an excessive rate.

When it is desired to (1) initially from the $C_{10}$–$C_{12}$ straight chain or branched chain diphenyl oxide alkali metal sulfonate or diphenyl oxide derivative-amine oxide-2,4-disubstituted and 2,2,4-trisubstituted tetrahydropyranyl-4-ether premix; (2) then combine the resulting premix with an alkali metal hypochlorite solution; (3) then add the thickening agent and then (4) adjust the pH of the resulting solution to the range of 11–14.0, then the temperature of mixing ranges are considered to be within the scope of this invention as follows:

| | | |
|---|---|---|
| (a) | Formation of the diphenyl oxide derivative or diphenyl oxide-amine oxide-2,4-disubstituted and 2,2,4-trisubstituted tetrahydropyranyl-4-ethers premix | 20° F.–150° F. |
| (b) | Mixing the premix with aqueous metal alkali hypochlorite solution followed by thickening agent | 20° F.–120° F. |
| (c) | Adjustment of pH of the solution to the range of 11–14.0 using aqueous alkali metal hydroxide solution. | 20° F.–120° F. |

In any event, wherever a mixing unit operation involves the aqueous alkali metal hypochlorite solution, the temperature of mixing is limited to the range of 20° F.–120° F. Where the mixing unit operation involves the mixing of 2,4-disubstituted and 2,2,4-trisubstituted tetrahydropyranyl-4-ethers, the upper bound of the temperature range is limited by the stability of the 2,4-disubstituted and 2,2,4-trisubstituted tetrahydropyranyl-4-ethers or other perfume ingredient mixed with the 2,4-disubstituted and 2,2,4-trisubstituted tetrahydropyranyl-4-ethers useable in the practice of our invention; and the lower bound of said temperature range is limited by the least temperature where a single liquid phase or gel phase including the 2,4-disubstituted and 2,2,4-trisubstituted tetrahydropyranyl-4-ethers or other ingredient admixed therewith will exist. Where a unit mixing operation of the process of our invention involves the mixing of one or more diphenyl derivatives having the generic structure:

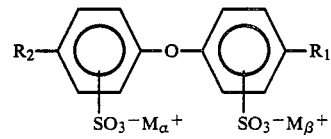

taken alone or taken together with one or more amine oxides having the generic structure:

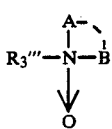

with other materials, the upper bound of the temperature range is the decomposition point of any one of the diphenyl oxide derivatives or amine oxide components and the lower bound is the least temperature where a single liquid phase or gel phase, including the diphenyl oxide derivatives or diphenyl oxide-amine mixture will exist.

Preferred diphenyl oxide derivative compositions from a practical standpont useful in the practice of our invention are compounds having the structure:

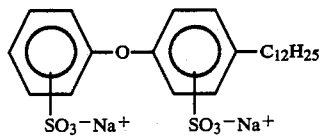

where the $C_{12}H_{25}$ moiety represents one or a series of different branched chains; compounds defined according to the structure:

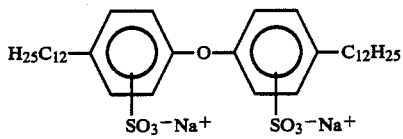

where the $C_{12}H_{25}$ moiety represents one or a series of different branched chains; compounds defined according to the structure:

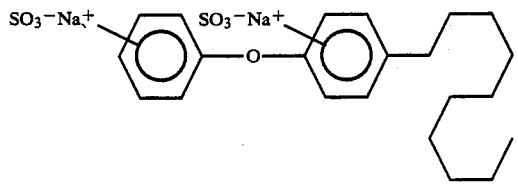

and compounds defined according to the structure:

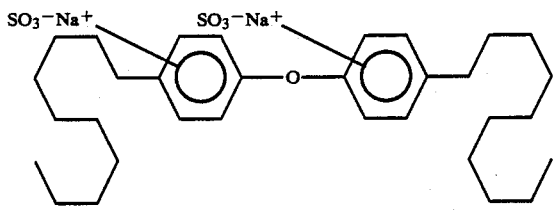

otherwise known as DOWFAX®2A1 in the case where one or $R_1$ or $R_2$ represents branched $C_{12}H_{25}$ alkyl chains and the other of $R_1$ or $R_2$ represents hydrogen, or DOWFAX®3B2 in the case where one of $R_1$ or $R_2$ represents straight $C_{10}$ alkyl chain and the other of $R_1$ or $R_2$ represents hydrogen (DOWFAX® being a registered trademark of the Dow Chemical Company of Midland, Mich.).

When used in conjunction with the diphenyl oxide derivatives preferred amine oxide compositions, from a practical standpoint, useful in the practice of our invention are the commercially available (1) dimethyl "cocoamine" oxide (a mixture which is dominated by dimethyl-$C_{12}$–$C_{16}$ straight chain alkyl amine oxides: more particularly a mixture containing approximately 70% $C_{12}$ straight chain alkyl amines oxides, approximately 25% of straight chain $C_{14}$ alkyl amine oxides and approximately 4% straight chain $C_{16}$ alkyl amine oxides) and (2) N-cocomorpholine oxide, a mixture dominated by straight chain $C_{12}$–$C_{16}$ alkyl morpholine oxides (specifically containing approximately 70% straight chain $C_{12}$ alkyl morpholine oxide, approximately 25% straight chain $C_{14}$ alkyl morpholine oxide, and approximately 4% straight chain $C_{16}$ alkyl morpholine oxide). Commercial examples of such amine oxide compositions are: AROMOX® DMC-W and AROMOX® DMMC-W which are 30% aqueous dimethyl cocoamine oxide solutions and AROMOX® NCMDW which is a 40% aqueous N-cocomorpholine oxide solution each of which is produced by the Armac Division of AKZO of Chicago, Ill. These materials are described in Brochure 68011, published by Armous Industrial Chemicals, P.O. Box 1805, Chicago, Ill. 60690. Other preferred amine oxides are n-undecyl dimethyl amine oxide and n-tridecyl dimethyl amine oxide.

The percentage of hypochlorite ion in the compositions of our invention may vary from about 1% up to about 20% for the desired effects to be produced using the diphenyl oxide derivative or diphenyl oxide derivative-amine-oxide 2,4-disubstituted and 2,2,4-trisubstituted tetrahydropyranyl-4-ethers compositions covered by our invention. The usual percent of alkali metal hypochlorite in solution is about 5%, the percentage of sodium hypochlorite in such mixtures as CLOROX® the registered trademark of the Clorox Corporation.

The perfume oil used in conjunction with the 2,2,4-trisubstituted tetrahydropyranyl-4-ethers of our invention which, in turn, is used in conjunction with the aqueous alkali metal hypochlorite solution must have such properties as to be able (1) to be compatible with the 2,4-disubstituted and 2,2,4-trisubstituted tetrahydropyranyl-4-ethers of our invention; (2) to impart to the resulting or "aqueous alkali metal hypochlorite" liquid or gel solution a pleasing aroma which harmonizes with the aroma of the 2,4-disubstituted and 2,2,4-trisubstituted tetrahydropyranyl-4-ethers; (3) to effect a substantial diminution or elimination of the disagreeable "hypochlorite" aroma which is imparted to surfaces (e.g., bleached laundry or the hands of the user which are in direct contact with the hypochlorite solution) on which known aqueous alkali metal hypochlorite solutions have been used; and (4) to impart to the surfaces with which such aqueous alkali metal hypochlorite solutions are in contact, a pleasant long lasting stable aroma. Examples of ingredients compatible with 2,4-disubstituted and 2,2,4-trisubstituted tetrahydropyranyl-4-ethers and suitable for the aforementioned purposes, that is, useable in conjunction with the hypochlorites, amine oxide derivatives and diphenyl oxide derivatives of our invention are as follows:

1. Cedryl alkyl ethers covered by U.S. Pat. No. 3,373,208 such as cedryl methyl ether;
2. Isochroman musks covered by U.S. Pat. Nos. 3,360,530 and 3,591,528 such as 6-oxa-1,1,3,3,8-pentamethyl-2,3,5,6,7,8-hexahydro-1H-benz(1)indene;

3. Polycyclic ethers covered by U.S. Pat. No. 3,281,432, such as octahydro-1,3a-6-trimethyl-1H-1,6a,ethanopentaleno-(1,2-C)furan;
4. Polycyclic ketones such as hexahydro-1,1,5,5-tetramethyl-2H-2,4a-methanonaphthalen-8-(5H)one;
5. Diisoamylenes described according to application for U.S. Letters Pateent, Ser. No. 188,576 filed on Sept. 18, 1980;
6. Acyldiisoamylene derivatives described according to application for U.S. Letters Patent, Ser. No. 184,132 filed on Sept. 4, 1980 and ketal derivatives thereof described according to application for U.S. Letters Patent, Ser. No. 212,993 filed on Dec. 4, 1980; and
7. Diisoamylene epoxide derivatives according to application for U.S. Letters Patent, Ser. No. 231,773 filed on Feb. 27, 1981.

It will be understood that a number of materials which impart to the citrusy or floral aromas of certain of the 2,4-disubstituted and 2,2,4-trisubstituted tetrahydropyranyl-4-ethers of our invention additional eucalyptol-like, or minty or woody nuances will not be useful for the practice of that aspect of our invention concerning perfumed hypochlorite bleaches because they are, interalia, easily oxidized by the alkali metal hypochlorite in the system. Examples are 1,5,9-trimethyl-12-acetyl-cyclododecatriene-1,5,8 and 1,5,9-trimethyl-12-cyclodeadiene-1,8 covered by British Patent No. 1,204,409.

A basic feature of our invention concerns the fact that the only detergent group needed or desirable in the composition of our invention is the class of diphenyl oxide derivatives defined according to the structure:

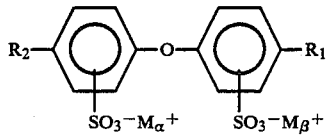

wherein $R_1$, $R_2$, M and N are defined, supra, taken alone or in conjunction with the class of morpholino and/or dimethyl $C_{11}$–$C_{13}$ straight chain alkyl amine oxides defined according to the structure:

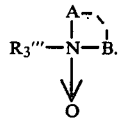

More specifically, such detergents as sodium decyl ether sulfate, sodium myristyl ether sulfate, sodium lauryl ether sulfate and lithium lauryl ether sulfate are neither desire nor are they required. Furthermore, the well known hydrotropes employed in prior art compositions such as the well known families of clarifying agents comprising the alkali metal or alkai earth metal salts of mono- and polyalkylated benzene or naphthalene sulfonates such as sodium xylene or magnesium toluene sulfonate are again neither desired nor are they required in the composition intended to be encompassed by the instant invention.

Another basic feature of our invention concerns the fact that when it is desired to have a gel phase composition, thickener agents may be employed in conjunction with the system; hypochlorite bleach-2,4-disubstituted and 2,2,4-trisubstituted tetrahydropyranyl-4-ethers-diphenyl oxide derivative or plain oxide derivative-amine oxide derivative (having the general structure)

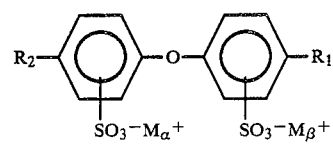

and having the structure:

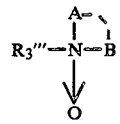

of our invention.

Still another basic feature of our invention concerns the fact that the gel phase compositions including thickener agents are employed with the "premix" system; 2,4-disubstituted and 2,2,4-trisubstituted tetrahydropyranyl-4-ethers-diphenyl oxide derivative or diphenyl oxide derivative-amine oxide of our invention.

Thus, sodium palmitate, sodium stearate, sodium laurate, potassium palmitate, potassium stearate, potassium laurate, lithium palmitate, lithium stearate and/or lithium laurate or combinations of the foregoing may be added to the compositions of matter of our invention to provide a thickened gel-type hypochlorite bleach which is, in addition to being a semi-solid state, is unobviously, advantageously and unexpectedly stable over long periods of time. Percentages of thickening agents such as sodium palmitate, sodium stearate, sodium laurate, potassium palmitate, potassium stearate, potassium laurate, lithium palmitate, lithium stearate or lithium laurate or combinations of these which may be used in the thickened compositions of our invention are from 1% by weight up to 12% by weight of the thickener based on the overall weight of hypochlorite bleach-diphenyl oxide-derivative (or diphenyl oxide derivative-amine oxide)2,4-disubstituted and 2,2,4-trisubstituted tetrahydropyranyl-4-ethers composition of our invention. When it is merely desired to have a thickened "premix" the percentage of thickening agent may very from about 5% up to about 40% by weight of thickener based on overall weight of "premix".

The following Examples I-XX serve to illustrate processes for producing the 2,4-disubstituted and 2,2,4-trisubstituted tetrahydropyranyl-4-ethers of our invention. Examples following Example XX, e.g., Examples XXI, et seq. illustrate the organoleptic uses of the 2,4-disubstituted and 2,2,4-trisubstituted tetrahydropyranyl-4-ethers of our invention.

It will be understood that these examples are illustrative and that the invention is to be considered restricted thereto only as indicated in the appended claims. All parts and percentages given herewith are by weight unless otherwise specified.

The following table illustrates organoleptic properties of certain precursor alcohols of the prior art compounds which may be used in producing certain of the 2,4-disubstituted and 2,2,4-trisubstituted tetrahydropyranyl-4-ethers of our invention:

TABLE II

| Prior Art Compound Structure | Organoleptic Utilities |
|---|---|
| The compound having the structure: 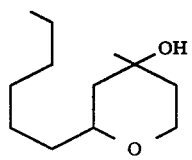 produced according to U.S.S.R. Patent No. 620,847 of July 17, 1987 the specification for wich is incorported by reference herein (abstracted at Chem. Abstracts, Volume 89, No. 185929p). | A nasturtium aroma profile. |
| The compound having the structure: 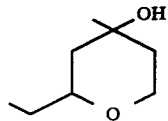 produced according to Example I of application for U.S. Letters Pat. Ser. No. 308,182 filed on February 9, 1989, the specification of which is incorporated by reference herein. | A nerol, caramel, methacrylate, chamomile aroma with a non descript undertone. |
| The compound having the structure: 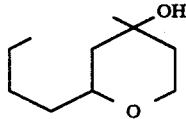 produced according to Example VII of application for U.S. Letters Pat. Ser. No. 308,182 filed on Feb. 9, 1989, the specification of which is incorporated by reference herein. | A floral (muguet), spicy (nutmeg) aroma profile with a weak muguet topnote. |
| The compound having the structure: 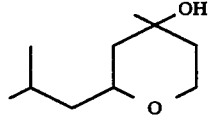 | A terpenic, flat floral (muguet) aroma profile with floral (muguet/freesia) undertones. |
| The compound having the structure: 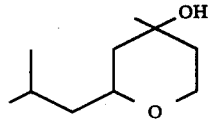 purchased under the name "FLORAL®" from the Firmenich, et Cie S.A. | A sweet, muguet, green aroma with floral (muguet) topnotes. | of Geneva, Switzerland.

EXAMPLE I

Preparation of Tetrahydro-4-Methoxy-4-Methyl-2-n-Propyl-2H-Pyran

Reactions:

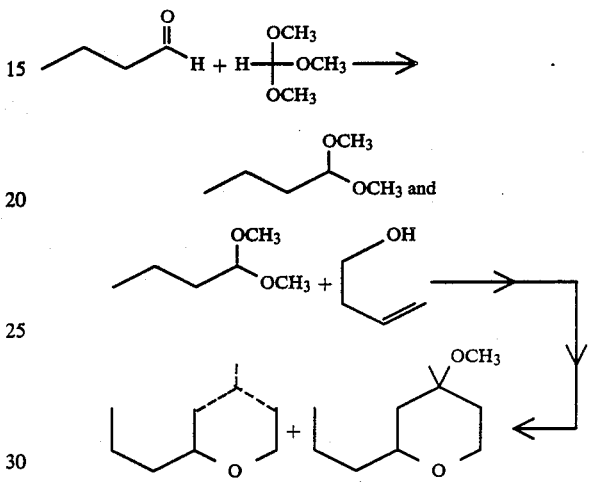

A solution of 7 grams of sulfuric acid is intimately admixed with 344 grams of isoprenol.

Into a 2 liter reaction vessel equipped with stirrer, thermometer and reflux condenser and cooling bath are placed 288 grams of butyraldehyde, 530 grams of trimethylorthoformate and 100 grams of methanol. The resulting mixture is cooled to −5° C. and then allowed to reach +10° C. While maintaining the reaction mass at 10° C., dropwise over a period of 0.5 hours, 8 grams of concentrated hydro-chloric acid is added thereto. The temperature of the reaction mass is then permitted to rise to room temperature.

The reaction mass is quenched by adding thereto 8 grams of sodium acetate followed by 600 ml water and stirring for ten minutes.

The resulting organic phase is separated from the aqueous phase.

The previously-prepared mixture containing 344 grams of isoprenol is then admixed with the reaction mass slowly over a two hour period.

The resulting reaction product is quenched with 60 grams of 50% aqueous sodium hydroxide followed by 300 grams of water. The organic phase is separated from the aqueous phase and the organic phase is distilled on a 1½"×12" Goodloe column yielding the following fractions:

| Fraction No. | Vapor Temp. (°C.) | Liquid Temp. (°C.) | Vacuum mm/Hg. Pressure |
|---|---|---|---|
| 1 | 45/ | 74/ | 3/30 |
| 2 | 48 | 74 | 10 |
| 3 | 48 | 74 | 10 |
| 4 | 48 | 77 | 10 |
| 5 | 48 | 80 | 10 |
| 6 | 55 | 83 | 10 |
| 7 | 70 | 85 | 10 |

-continued

| Fraction No. | Vapor Temp. (°C.) | Liquid Temp. (°C.) | Vacuum mm/Hg. Pressure |
|---|---|---|---|
| 8 | 74 | 86 | 10 |
| 9 | 75 | 93 | 10 |
| 10 | 75 | 92 | 10 |
| 11 | 75 | 103 | 10 |
| 12 | 77 | 106 | 10 |
| 13 | 90 | 130 | 10. |

FIG. 1 is the GLC profile for the reaction product prior to distillation.

The peaks indicated by reference numerals 10 and 11 are for the compound having the structure:

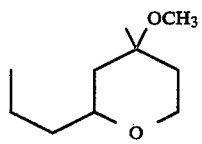

The peaks indicated by reference numerals 12 and 13 are for the mixture of compounds defined according to the structure:

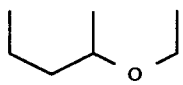

wherein in the mixture in each of the compounds one of the dashed lines represents a carbon-carbon double bond and each of the other of the dashed lines represent carbon-carbon single bonds.

Fractions 8–13 when bulked contain solely the compound having the structure:

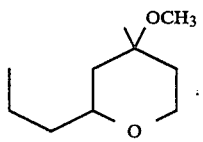

The compound having the structure:

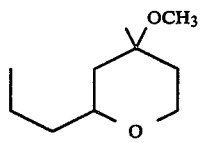

has a green, herbaceous, parsley, rose, fruity, spicy and earthy and rooty aroma profile, FIG. 2 is the NMR spectrum for distillation Fraction 11 which is for the compound having the structure:

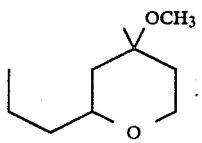

EXAMPLE II

Preparation of Tetrahydro-2-isopropyl-4-methoxy-4-methyl-2H-pyran

Reactions:

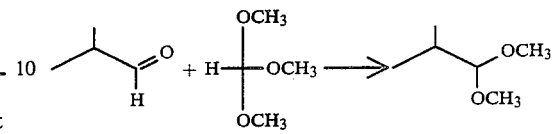

and

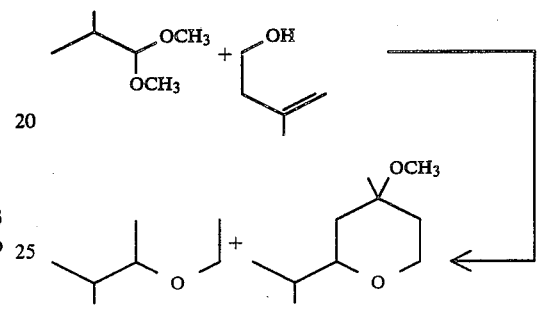

The procedure of Example I is carried out with the exception that the following ingredients (with their weights) are used in place of the reagents in Example I:

| Reagent | Weight |
|---|---|
| Isobutyraldehyde | 288 grams (4 moles) |
| Trimethylorthoformate | 530 grams (5 moles) |
| Concentrated hydrochloric acid | 4 ml |
| Sodium acetate | 8 grams |
| Isoprenol | 344 grams |
| Sulfuric acid concentracted | 6 grams |
| Sodium hydroxide (50% aqueous sodium solution) | 60 grams |

After the reaction mass is quenched, the organic phase is distilled on a 1½"×12" Goodloe column yielding the following fractions:

| Fraction No. | Vapor Temp. (°C.) | Liquid Temp. (°C.) | Vacuum mm/Hg. Pressure |
|---|---|---|---|
| 1 | 16/ | 18/ | 2.4 |
| 2 | 35 | 69 | 2.2 |
| 3 | 30 | 70 | 2.5 |
| 4 | 40 | 74 | 2.4 |
| 5 | 51 | 80 | 2.8 |
| 6 | 55 | 80 | 3.2 |
| 7 | 56 | 90 | 3.2 |
| 8 | 54 | 86 | 3.0 |
| 9 | 56 | 94 | 3.2 |
| 10 | 61 | 98 | 3.6 |
| 11 | 66 | 108 | 3.7 |
| 12 | 74 | 118 | 3.4. |

Fractions 7–12 contain solely the compound having the structure:

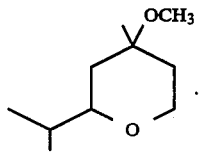

Fractions 2–5 contain solely the mixture of compounds having the structure:

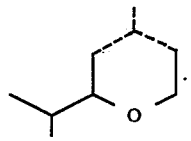

The compound having the structure:

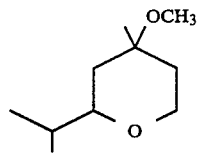

has a sauge sclaree, minty and woody aroma profile. The mixture of compounds having the structure:

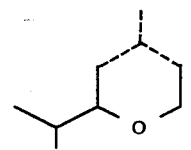

has a floral, green and minty aroma profile.

EXAMPLE III

Preparation of
2-Butyltetrahydro-4-methoxy-4-methyl-2H-pyran

Reactions:

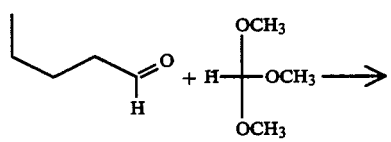

and

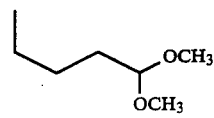

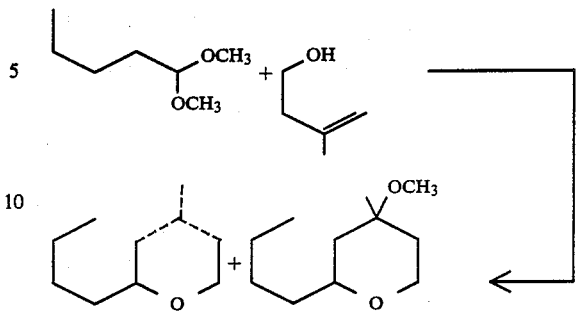

A procedure is carried out similar to the procedure of Example I with the exception that the following reagents are used:

| Reagent | Quantity |
|---|---|
| N-Pentanal | 344 grams |
| Trimethylorthoformate | 530 grams |
| Concentrated Hydrochloric acid | 4 ml |
| Methyl alcohol | 100 ml |
| Sodium Acetate | 8 grams |
| Isoprenol | 344 grams |
| Sulfuric acid (concentrated) | 8 grams |
| 50% Aqueous Sodium Hydroxide | 60 grams |

Subsequent to the workup, the organic phase is distilled on a 1½"×12" Goodloe column yielding the following fractions:

| Fraction No. | Vapor Temp. (°C.) | Liquid Temp. (°C.) | Vacuum mm/Hg. Pressure |
|---|---|---|---|
| 1 | 42/ | 78/ | 2.0 |
| 2 | 53 | 86 | 5.0 |
| 3 | 59 | 91 | 6.5 |
| 4 | 62 | 91 | 6.5 |
| 5 | 68 | 95 | 7.0 |
| 6 | 79 | 96 | 6.5 |
| 7 | 83 | 96 | 6.0 |
| 8 | 85 | 97 | 6.0 |
| 9 | 85 | 97 | 6.0 |
| 10 | 86 | 98 | 6.0 |
| 11 | 86 | 100 | 6.0 |
| 12 | 87 | 103 | 6.0 |
| 13 | 84 | 118 | 6.0 |
| 14 | 79 | 147 | 6.0 |
| 15 | 79 | 180 | 6.0. |

Fractions 12, 13 and 14 consist of the compound having the structure:

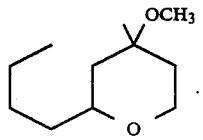

The compound having the structure:

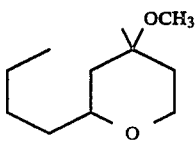

has a fruity, herbaceous, celery-like, citrusy aroma with fruity, floral, jasmine, lily of the valley, green and herbaceous undertones.

Fractions 2-10 consist of the mixture of compounds defined according to the generic structure:

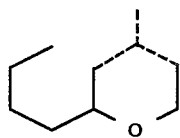

wherein in each of the compounds, one of the dashed lines is a carbon-carbon double bond and each of the other of the dashed lines represent carbon-carbon single bonds.

EXAMPLE IV

Preparation of Tetrahydro-4-methoxy-4-methyl-2-N-pentyl-2H-pyran

Reactions:

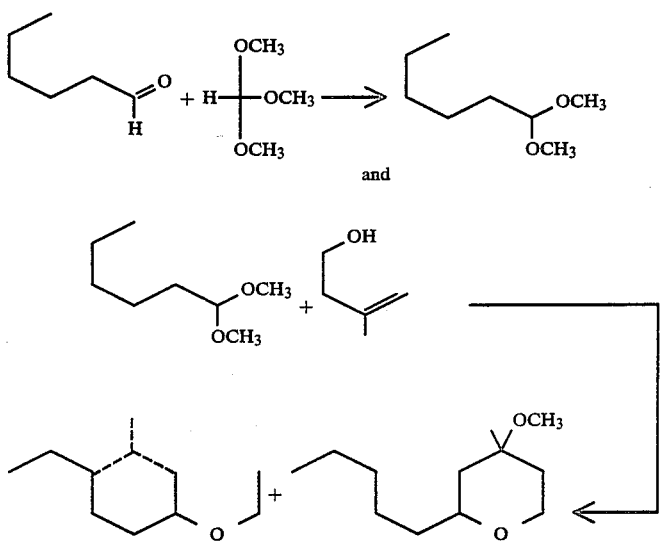

A procedure is carried out similar to that of Example I with the exception that the following reagents are used in the reactions:

| Reagent | Weight |
| --- | --- |
| n-Hexanal | 400 grams |
| Trimethylorthoformate | 530 grams |
| Methyl Alcohol | 100 grams |
| Sodium Acetate | 8 grams |
| Isoprenol | 344 grams |
| Sulfuric Acid (concentrated) | 8 grams |
| 50% Aqueous Sodium Hydroxide | 60 grams |

After the workup the organic phase is distilled on a micro vigreux column yielding the following fractions:

| Fraction No. | Vapor Temp. (°C.) | Liquid Temp. (°C.) | Vacuum mm/Hg. Pressure |
| --- | --- | --- | --- |
| 1 | 32/ | 88/ | 2.4 |
| 2 | 48 | 92 | 2.4 |
| 3 | 55 | 94 | 2.4 |
| 4 | 56 | 94 | 2.4 |
| 5 | 56 | 97 | 2.4 |
| 6 | 57 | 97 | 2.4 |
| 7 | 58 | 100 | 2.4 |
| 8 | 60 | 103 | 2.4 |
| 9 | 67 | 105 | 2.4 |
| 10 | 71 | 105 | 2.4 |
| 11 | 75 | 107 | 2.4 |
| 12 | 77 | 107 | 2.4 |
| 13 | 77 | 107 | 2.4 |
| 14 | 78 | 107 | 2.4 |
| 15 | 78 | 107 | 2.4 |
| 16 | 82 | 108 | 2.4 |
| 17 | 82 | 108 | 2.4 |
| 18 | 58 | 180 | 2.6. |

Fractions 10-18 consist of the compound having the structure:

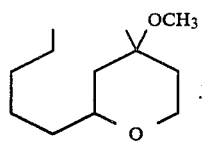

The compound having the structure:

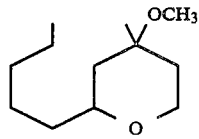

has a fresh, clean, tangerine-like, fruity, jasmine aroma with galbanum, jasmine, celery-like, green and pineapple topnotes.

EXAMPLE V

Preparation of Morflorate Methyl Ether

Reactions:

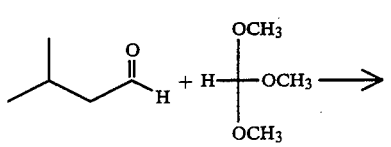

and

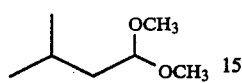

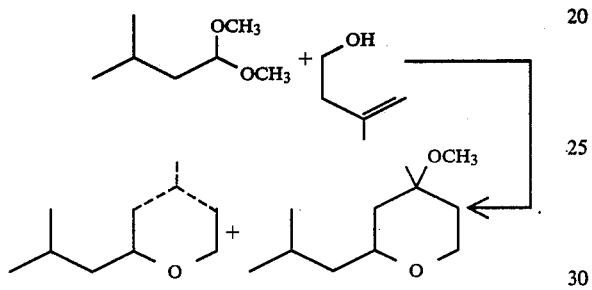

A procedure is carried out similar to the procedure of Example I with the exception that the following reagents are used in the reaction:

| Reagent | Weight |
|---|---|
| Isovaleraldehyde | 516 grams |
| Trimethylorthoformate | 756 grams |
| Concentrated Hydrochloric Acid | 12 ml |
| Sodium Acetate | 20 grams |
| Isoprenol | 602 grams |
| Sulfuric Acid (concentrated) | 5 grams |

After the reaction mass is quenched the organic phase is distilled on a 1½"×12" Goodloe column yielding the following fractions:

| Fraction No. | Vapor Temp. (°C.) | Liquid Temp. (°C.) | Vacuum mm/Hg. Pressure |
|---|---|---|---|
| 1 | 23/78 | 23/100 | 1.5 |
| 2 | 76 | 90 | 6.0 |
| 3 | 76 | 90 | 6.0 |
| 4 | 78 | 96 | 6.0 |
| 5 | 80 | 96 | 4.0 |
| 6 | 80 | 96 | 4.0 |
| 7 | 80 | 96 | 3.0 |
| 8 | 80 | 96 | 3.0 |
| 9 | 80 | 96 | 3.0 |
| 10 | 82 | 100 | 3.0 |
| 11 | 85 | 110 | 3.0 |
| 12 | 70 | 150 | 2.0 |
| 13 | 70 | 180 | 2.0 |

Fractions 2-5 consist of the mixture of compounds defined according to the structure:

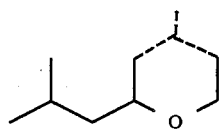

wherein in the mixture, one of the dashed lines is a carbon-carbon double bond and each of the other of the dashed lines represnt carbon-carbon single bonds.

Fractions 7-13 consist of the compound having the structure:

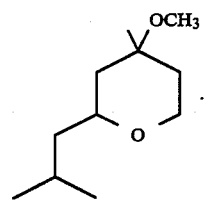

The compound having the structure:

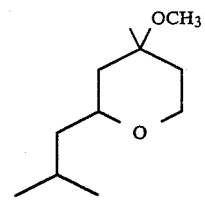

has a green, herbaceous and woody aroma profile with floral undertones.

EXAMPLE VI

Preparation of Tetrahydro-4-methoxy-4-methyl-2(1-methylbutyl)-2H pyran

Reactions:

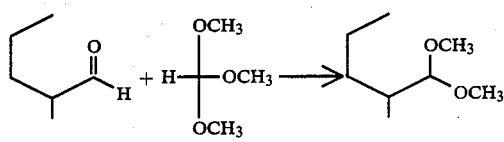

and

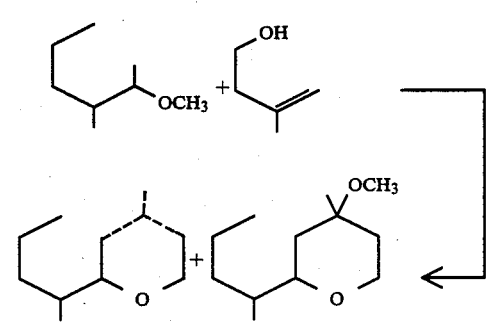

A procedure is carried out similar to that of Example I with the exception that the following reagents are used:

| Reagent | Weight |
|---|---|
| 2-Methylpentanal | 400 grams |
| Trimethylorthoformate | 530 grams |
| Methyl Alcohol | 100 grams |
| Concentrated Hydrochloric Acid | 4 ml |
| Sodium Acetate | 8 grams |
| Isoprenol | 344 grams |
| Sulfuric Acid (concentrated) | 7 grams |
| Sodium Hydroxide (50% Aqueous) | 60 grams |

After quenching the organic phase is distilled on a 1½"×15" Goodloe column yielding the following fractions:

| Fraction No. | Vapor Temp. (°C.) | Liquid Temp. (°C.) | Vacuum mm/Hg. Pressure |
|---|---|---|---|
| 1 | 56/ | 98/ | 6.0 |
| 2 | 72 | 100 | 6.0 |
| 3 | 74 | 103 | 5.5 |
| 4 | 75 | 103 | 6.0 |
| 5 | 77 | 105 | 6.0 |
| 6 | 78 | 106 | 6.0 |
| 7 | 80 | 108 | 6.0 |
| 8 | 85 | 108 | 6.0 |
| 9 | 94 | 110 | 6.0 |
| 10 | 100 | 110 | 6.0 |
| 11 | 101 | 112 | 6.0 |
| 12 | 102 | 112 | 6.0 |
| 13 | 102 | 112 | 6.0 |
| 14 | 103 | 115 | 6.0 |
| 15 | 104 | 120 | 6.0 |
| 16 | 64 | 164 | 6.5 |
| 17 | 140 | 180 | 6.5. |

Fractions 9-16 consist of the compound having the structure:

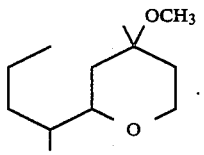

The compound having the structure:

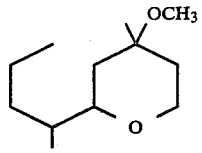

has a spicy, dill, caraway, herbaceous aroma with animalic, dill and caraway undertones.

Fractions 2-21 consist of the mixture of compounds defined according to the structure:

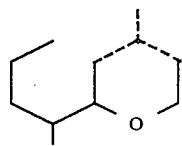

wherein in the mixture in each of the compounds one of the dashed lines is a carbon-carbon double bond and each of the other of the dashed lines are carbon-carbon single bonds. The mixture of compounds having the structure:

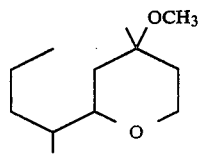

has a floral, green, minty, pepper and rose aroma profile.

EXAMPLE VII

Preparation of Tetrahydro-4-Methoxy-4-Methyl-2(1-Methyl-1-Butenyl)-2H-Pyran

Reactions:

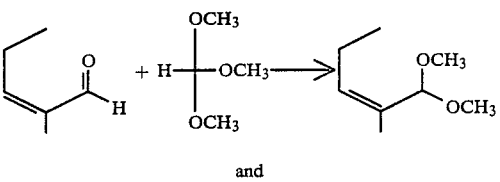

and

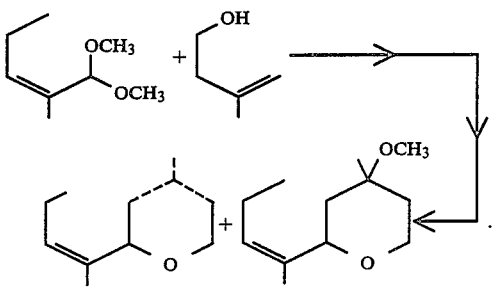

A procedure is carried out similar to that of Example I with the exception that the following reagents are used:

| Reagent | Weight |
|---|---|
| 2-Methyl-2-Pentenal | 392 grams |
| Trimethylorthoformate | 530 grams |
| Methyl Alcohol | 100 grams |
| Concentrated Hydrochloric Acid | 4 ml |
| Sodium Acetate | 8 grams |
| Isoprenol | 344 grams |
| Sulfuric Acid (concentrated) | 7 grams |
| 50% Aqueous Sodium Hydroxide | 60 grams |

After quenching the organic phase is distilled on a 1"×12" Goodloe column yielding the following fractions:

| Fraction No. | Vapor Temp. (°C.) | Liquid Temp. (°C.) | Vacuum mm/Hg. Pressure |
|---|---|---|---|
| 1 | 22/ | 115/ | |

-continued

| Fraction No. | Vapor Temp. (°C.) | Liquid Temp. (°C.) | Vacuum mm/Hg. Pressure |
|---|---|---|---|
| 2 | 20 | 110 | 4.0 |
| 3 | 50 | 112 | 5.5 |
| 4 | 73 | 117 | 5.0 |
| 5 | 83 | 122 | 5.0 |
| 6 | 96 | 127 | 5.0 |
| 7 | 97 | 125 | 5.0 |
| 8 | 106 | 127 | 5.0 |
| 9 | 104 | 152 | 5.0 |
| 10 | 110 | 168 | 6.0 |
| 11 | 114 | 182 | 6.0 |
| 12 | 116 | 185 | 6.0. |

Fractions 7–11 (bulked) consist of the compound having the structure:

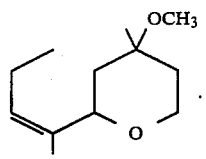

The compound having the structure:

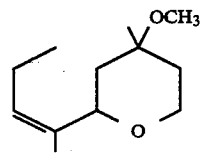

has a nutty and coconut aroma profile with cinnamon and pineapple topnotes and floral and herbaceous undertones.

EXAMPLE VIII

Preparation of Tetrahydro-4-Methoxy-4-Methyl-2-Phenyl-2H-Pyran

Reactions:

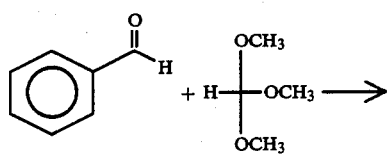

and

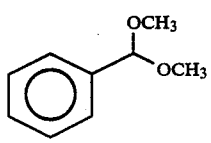

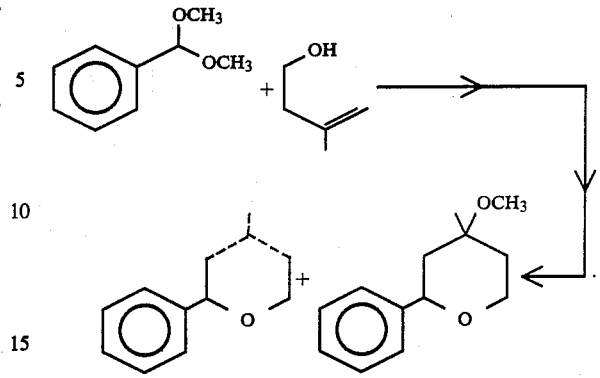

A procedure is carried out similar to that of Example I with the exception that the following reagents are used:

| Reagent | Weight |
|---|---|
| Benzaldehyde | 424 grams |
| Trimethylorthoformate | 530 grams |
| Methyl Alcohol | 110 grams |
| Sodium Acetate | 8 grams |
| Isoprenol | 344 grams |
| Sulfuric Acid | 8 grams |
| Isoprenol | 344 grams |
| Sulfuric Acid (concentrated) | 8 grams |
| Sodium Hydroxide (50% solution) | 60 grams |
| Concentrated Hydrochloric Acid | 4 ml |

After quenching the reaction mass is distilled on a 1½"×12" Goodloe column yielding the following fractions:

| Fraction No. | Vapor Temp. (°C.) | Liquid Temp. (°C.) | Vacuum mm/Hg. Pressure |
|---|---|---|---|
| 1 | 70/ | 123/ | 4.0 |
| 2 | 96 | 124 | 4.0 |
| 3 | 96 | 124 | 4.0 |
| 4 | 96 | 126 | 4.0 |
| 5 | 96 | 128 | 4.0 |
| 6 | 96 | 128 | 4.0 |
| 7 | 96 | 128 | 4.0 |
| 8 | 98 | 132 | 4.0 |
| 9 | 98 | 132 | 4.0 |
| 10 | 103 | 133 | 3.8 |
| 11 | 111 | 134 | 3.8 |
| 12 | 115 | 134 | 3.8 |
| 13 | 115 | 134 | 3.8 |
| 14 | 115 | 134 | 3.8 |
| 15 | 116 | 134 | 3.8 |
| 16 | 120 | 150 | 3.8 |
| 17 | 120 | 150 | 3.8 |
| 18 | 115 | 193 | 3.8 |
| 19 | 90 | 210 | 1.6. |

Fractions 12–18 consist of the compound having the structure:

EXAMPLE IX

Preparation of 2-Hexyltetrahydro-4-Methoxy-4-Methyl-2H-Pyran

Reactions:

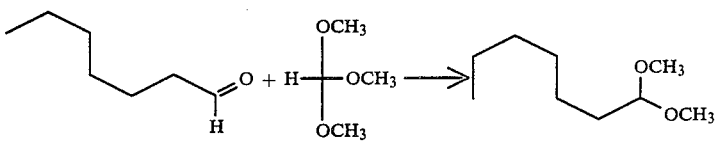

and

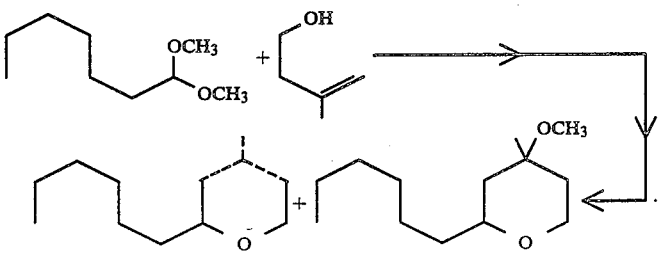

A procedure is carried out similar to that of Example I with the exception that the following reagents are used:

| Reagent | Weight |
|---|---|
| n-Heptaldehyde | 456 grams (4 moles) |
| Trimethylorthoformate | 530 grams (5 moles) |
| Concentrated Hydrochloric Acid | 4 ml |
| Sodium Acetate | 8 grams |
| Isoprenol | 344 grams (4 moles) |
| Sulfuric Acid (concentrated) | 8 grams |
| Sodium Hydroxide (50% Aqueous) | 70 grams |

After quenching the organic phase is distilled on a 1½"×12" Goodlow column yielding the following fractions:

| Fraction No. | Vapor Temp. (°C.) | Liquid Temp. (°C.) | Vacuum mm/Hg. Pressure |
|---|---|---|---|
| 1 | 48/ | 92/ | 4.0 |
| 2 | 45 | 93 | 3.0 |
| 3 | 45 | 93 | 3.0 |
| 4 | 49 | 93 | 6.0 |
| 5 | 47 | 94 | 6.0 |
| 6 | 56 | 104 | 6.0 |
| 7 | 50 | 104 | 6.0 |
| 8 | 78 | 108 | 6.0 |
| 9 | 83 | 108 | 6.0 |
| 10 | 85 | 112 | 6.0 |
| 11 | 85 | 114 | 6.0 |
| 12 | 85 | 114 | 6.0 |
| 13 | 86 | 115 | 6.0 |
| 14 | 91 | 128 | 6.0 |
| 15 | 93 | 119 | 6.0 |
| 16 | 100 | 121 | 6.0 |
| 17 | 105 | 122 | 6.0 |
| 18 | 108 | 125 | 6.0 |
| 19 | 109 | 128 | 6.0 |
| 20 | 108 | 127 | 6.0 |
| 21 | 108 | 130 | 6.0 |
| 22 | 108 | 139 | 6.0 |
| 23 | 108 | 160 | 6.0 |
| 24 | 112 | 170 | 6.0 |

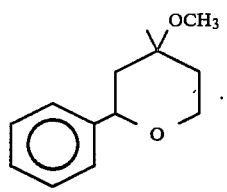

Fractions 3-8 consist of the mixture of compounds defined according to the structure:

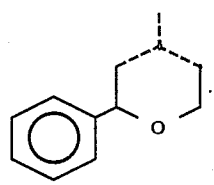

The compound having the structure:

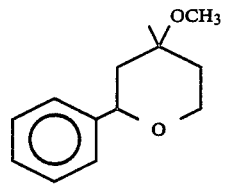

has a spicy aroma with oak moss topnotes.

The mixture of compounds having the structure:

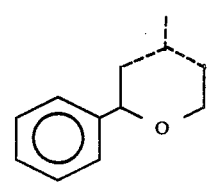

has a floral, sweet, rose aroma.

-continued

| Fraction No. | Vapor Temp. (°C.) | Liquid Temp. (°C.) | Vacuum mm/Hg. Pressure |
|---|---|---|---|
| 25 | 132 | 180 | 6.0 |
| 26 | 138 | 200 | 6.0 |
| 27 | 130 | 200 | 1.8 |

Fractions 10–15 consist of the mixture of compounds having the structure:

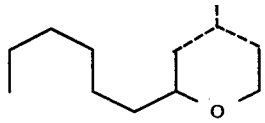

wherein in the mixture in each of the compounds, one of the dashed lines represents a carbon-carbon double bond and each of the other of the dashed lines represent carbon-carbon single bonds.

Fractions 17–23 consist of the compound having the structure:

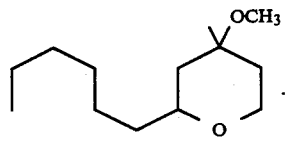

The compound having the structure:

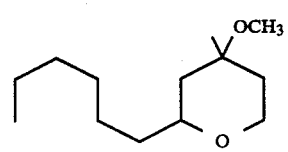

has a fruity, herbaceous, floral aroma with citrusy, herbaceous and floral undertones.

The mixture of compounds having the structure:

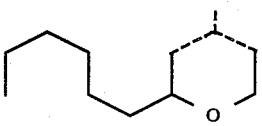

has a floral, green and galbanum aroma.

EXAMPLE X

Preparation of 2-n-Heptyltetrahydro-4-Methoxy-4-Methyl-2H-Pyran

Reactions:

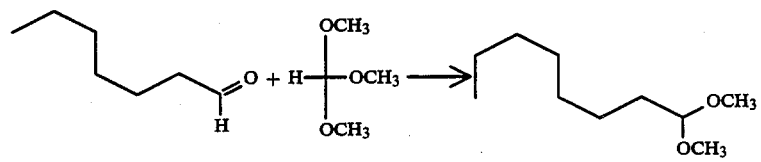

and

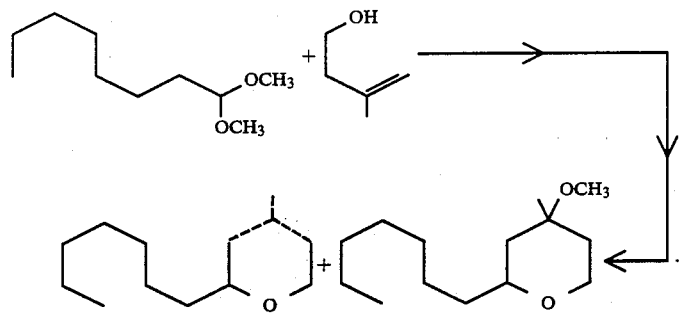

A procedure similar to that of Example I is carried out with the exception that the following reagents are used:

| Reagent | Weight |
|---|---|
| n-Octyl Aldehyde | 513 grams (4 moles) |
| Trimethylorthoformate | 530 grams (5 moles) |
| Methyl Alcohol | 100 grams |
| Concentrated Hydrochloric Acid | 5 ml |
| Sodium Acetate | 8 grams |
| Sulfuric Acid (concentrated) | 8 grams |
| Isoprenol | 344 grams (4 moles) |
| 50% Sodium Hydroxide | 60 grams |

After quenching the organic phase is distilled on a 1½"×12" Goodloe column yielding the following fractions:

| Fraction No. | Vapor Temp. (°C.) | Liquid Temp. (°C.) | Vacuum mm/Hg. Pressure |
|---|---|---|---|
| 1 | 65/ | 112/ | 5.0 |
| 2 | 91 | 115 | 5.0 |
| 3 | 92 | 118 | 5.0 |
| 4 | 93 | 118 | 5.0 |
| 5 | 94 | 118 | 5.0 |
| 6 | 94 | 121 | 5.0 |
| 7 | 96 | 124 | 5.0 |
| 8 | 97 | 128 | 5.0 |
| 9 | 98 | 130 | 5.0 |

-continued

| Fraction No. | Vapor Temp. (°C.) | Liquid Temp. (°C.) | Vacuum mm/Hg. Pressure |
|---|---|---|---|
| 10 | 116 | 134 | 5.0 |
| 11 | 122 | 138 | 5.5 |
| 12 | 120 | 138 | 5.3 |
| 13 | 115 | 136 | 4.6 |
| 14 | 117 | 142 | 4.6 |
| 15 | 118 | 162 | 4.6 |
| 16 | 114 | 182 | 4.6 |
| 17 | 128 | 200 | 4.6. |

Fractions 2-9 consist of the mixture of compounds having the structure:

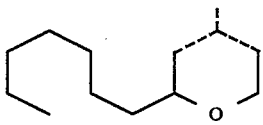

wherein in the mixture in each of the compounds one of the dashed lines represents a carbon-carbon double bond and each of the other of the dashed lines represent carbon-carbon single bonds.

Fractions 11-15 consist of the compound having the structure:

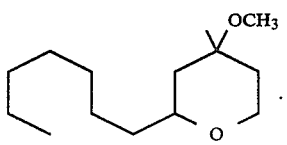

The compound having the structure:

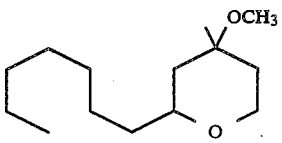

has a fruity, peach and coconut-like aroma profile with almond oil topnotes.

The mixture of compounds having the structure:

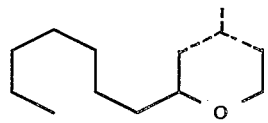

has a green, Rue oil-like aroma profile.

EXAMPLE XI

Preparation of Tetrahydro-4-Methoxy-4-Methyl-2-n-Octyl-2H-Pyran

Reactions:

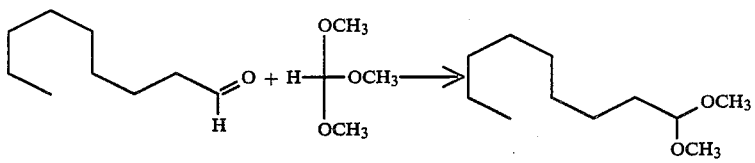

and

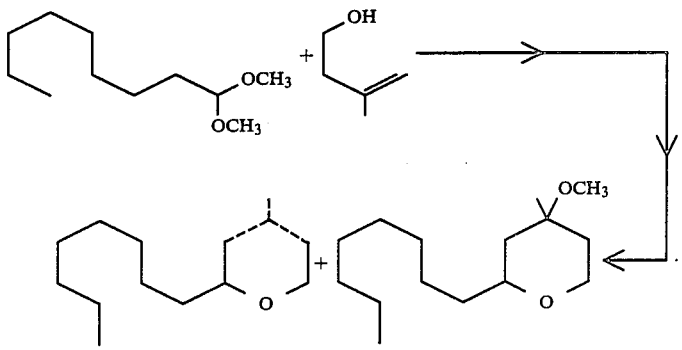

A procedure is carried out similar to that of Example I with the exception that the following reagents are used:

| Reagent | Weight |
|---|---|
| n-Nonyl Aldehyde (95%) | 250 grams (1.67 moles) |
| Trimethylorthoformate | 221 grams (2.09 moles) |
| Methyl Alcohol | 50 grams |
| Concentrated Hydrochloric Acid | 2 ml |
| Sodium Acetate | 4 grams |
| Isoprenol | 143 grams (1.67 moles) |
| Sulfuric Acid (concentrated) | 3.5 grams |
| Sodium Hydroxide (50% Aqueous) | 30 grams |

After quenching, the organic phase is distilled on a 1½"×15" Goodloe column yielding the following fractions:

| Fraction No. | Vapor Temp. (°C.) | Liquid Temp. (°C.) | Vacuum mm/Hg. Pressure |
| --- | --- | --- | --- |
| 1 | 80/ | 130/ | 4.0 |
| 2 | 101 | 126 | 3.5 |
| 3 | 105 | 130 | 3.5 |
| 4 | 105 | 131 | 3.5 |
| 5 | 105 | 133 | 3.5 |
| 6 | 105 | 133 | 3.5 |
| 7 | 107 | 142 | 3.5 |
| 8 | 102 | 144 | 3.5 |
| 9 | 125 | 155 | 3.2 |
| 10 | 125 | 170 | 3.2 |
| 11 | 125 | 185 | 3.2 |
| 12 | 125 | 200 | 3.2 |
| 13 | 124 | 215 | 1.9. |

The compound having the structure:

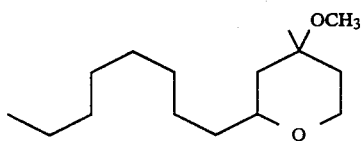

has a fresh, ozoney, seashore aroma with animalic topnotes.

The mixture of compounds defined according to the structure:

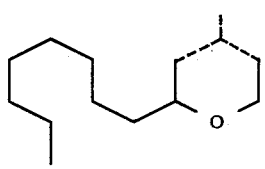

(wherein in the mixture in each of the compounds, one of the dashed lines is a carbon-carbon double bond and each of the other of the dashed lines represent carbon-carbon single bonds) has a citrusy, "air-dried clothing" aroma profile.

EXAMPLE XII

Preparation of 4-Ethoxy-2-Ethyltetrahydro-4-Methyl-2H-Pyran

Reaction:

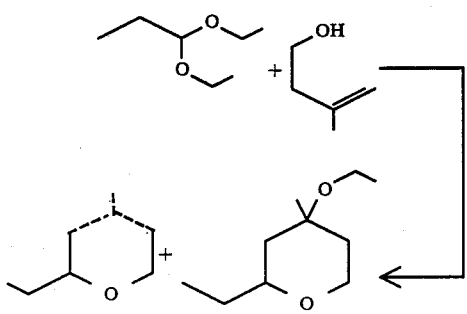

Into a 2 liter reaction vessel equipped with stirrer, thermometer and reflux condenser is added 508 grams of propionaldehyde diethyl acetal. The propionaldehyde diethyl acetal is heated to 80° C. with stirring.

Separately, a solution containing 8.6 grams of sulfuric acid and 330 grams of isoprenol is pre-prepared.

The pre-prepared sulfuric acid-isoprenol solution is added dropwise over a period of 1.5 hours to the propionaldehyde diethyl acetal.

After the addition of the isoprenol-sulfuric acid solution the reaction mass is stirred at a temperature of 80° C.

The reaction mass is then quenched with 58 grams of a 50% aqueous solution of sodium hydroxide followed by 500 ml water.

The crude reaction product is then distilled on a 1.5×12" Goodloe column yielding the following fractions:

| Fraction No. | Vapor Temp. (°C.) | Liquid Temp. (°C.) | Vacuum mm/Hg. Pressure |
| --- | --- | --- | --- |
| 1 | 34/ | 63/ | 6.0 |
| 2 | 34 | 67 | 6.0 |
| 3 | 49 | 71 | 6.0 |
| 4 | 55 | 73 | 6.0 |
| 5 | 57 | 74 | 6.0 |
| 6 | 60 | 76 | 6.0 |
| 7 | 60 | 78 | 6.0 |
| 8 | 63 | 85 | 6.0 |
| 9 | 63 | 101 | 6.0. |

The compound having the structure:

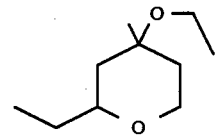

has a caramel, maple syrup aroma with green, herbaceous topnotes.

EXAMPLE XIII

Preparation of Tetrahydro-2-Isopropyl-4-Methoxy-2,4-Dimethyl-2H-Pyran

Reactions:

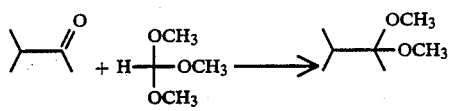

and

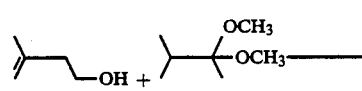

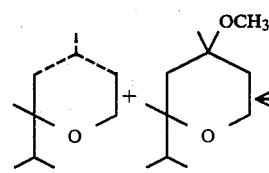

A procedure similar to that of Example I is carried out with the exception that the following reagents are used:

| Reagent | Weight |
|---|---|
| 3-Methylbutanone-2 | 344 grams |
| Trimethylorthoformate | 530 grams |
| Methyl Alcohol | 100 grams |
| Concentrated Hydrochloric Acid | 4 ml |
| Sodium Acetate | 8 grams |
| Concentrated Sulfuric Acid | 8 grams |
| Isoprenol | 344 grams |
| 50% Aqueous Sodium Hydroxide | 60 grams |

After quenching, the organic phase is distilled on a 1.5×12" Goodloe column yielding the following fractions:

| Fraction No. | Vapor Temp. (°C.) | Liquid Temp. (°C.) | Vacuum mm/Hg. Pressure |
|---|---|---|---|
| 1 | 42/ | 72/ | 4.0 |
| 2 | 42 | 72 | 4.0 |
| 3 | 42 | 72 | 5.0 |
| 4 | 42 | 72 | 6.0 |
| 5 | 44 | 72 | 6.0 |
| 6 | 48 | 74 | 6.0 |
| 7 | 50 | 76 | |
| 8 | 52 | 82 | 6.0 |
| 9 | 55 | 84 | 8.0 |
| 10 | 57 | 85 | 8.0 |
| 11 | 65 | 87 | 8.0 |
| 12 | 72 | 87 | 7.5 |
| 13 | 75 | 87 | 7.5 |
| 14 | 76 | 92 | 7.5 |
| 15 | 81 | 94 | 7.5 |
| 16 | 81 | 94 | 7.5 |
| 17 | 80 | 102 | 8.0 |
| 18 | 78 | 134 | 8.0 |
| 19 | 60 | 177 | 8.5 |
| 20 | 30 | 200 | 8.0. |

Fractions 11-20 consist of the compound having the structure:

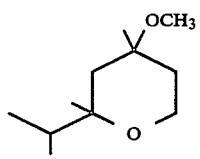

The compound having the structure:

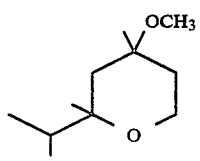

has a minty, woody, green, herbaceous aroma with camphoraceous and eucalyptus-like topnotes.

EXAMPLE XIV

Preparation of Tetrahydro-2-Isobutyl-4-Methoxy-2,4-Dimethyl 2H-Pyran

Reactions:

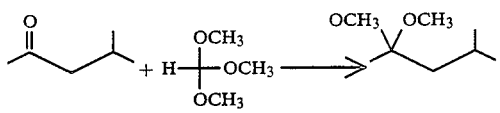

and

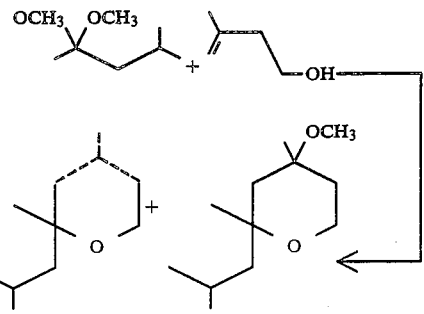

A procedure is carried out similar to that of Example XII except that the following reagents are used:

| Reagent | Weight |
|---|---|
| Methylpentanone Dimethyl Ketal | 600 grams |
| Isoprenol | 600 grams |
| Concentrated Sulfuric Acid | 6 grams |
| 10% Aqueous Sodium Carbonate Quench Solution | 1 liter |

After quenching the organic phase is distilled on a 1.5×12" Goodloe column yielding the following fractions:

| Fraction No. | Vapor Temp. (°C.) | Liquid Temp. (°C.) | Vacuum mm/Hg. Pressure |
|---|---|---|---|
| 1 | 23/65 | 23/90 | 25/10 |
| 2 | 65 | 90 | 10.0 |
| 3 | 68 | 93 | 8.0 |
| 4 | 70 | 72 | 8.0 |
| 5 | 70 | 96 | 3.0 |
| 6 | 70 | 96 | 2.0 |
| 7 | 78 | 98 | 2.0 |
| 8 | 78 | 96 | 2.0 |
| 9 | 78 | 96 | 2.0 |
| 10 | 78 | 95 | 2.0 |
| 11 | 78 | 98 | 2.0 |
| 12 | 70 | 116 | 1.0 |
| 13 | 65 | 122 | 1.0 |
| 14 | 65 | 165 | 2.0. |

The resulting compound having the structure:

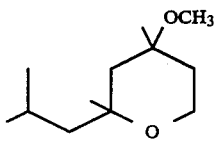

has a citrusy, grapefruit and nootkatone-like aroma profile.

EXAMPLE XV

Preparation of 2-n-Hexyltetrahydro-4-Methoxy-2,4-Dimethyl-2H-Pyran

Reactions:

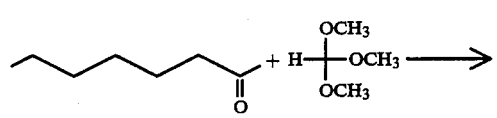

and

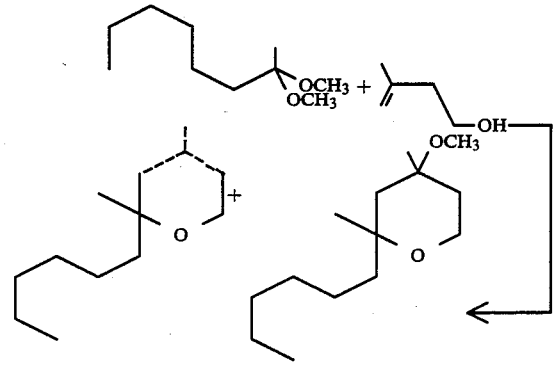

The procedure of Example I is utilized with the exception that the following reagents are used:

| Reagent | Weight |
| --- | --- |
| 2-Octanone | 512 grams |
| Trimethylorthoformate | 530 grams |
| Methyl Alcohol | 100 grams |
| Concentrated Hydrochloric Acid | 5 ml. |
| Sodium Acetate | 10 grams |
| Isoprenol | 344 grams (4 moles) |
| Concentrated Sulfuric Acid | 9 grams |
| 50% Aqueous Sodium Hydroxide | 60 grams |

After quenching the organic phase is distilled on a B 1"×12" Goodloe column yielding the following fractions:

| Fraction No. | Vapor Temp. (°C.) | Liquid Temp. (°C.) | Vacuum mm/Hg. Pressure | Reflux Ratio |
| --- | --- | --- | --- | --- |
| 1 | 58/ |  | 5.0 | 3:1 |
| 2 | 83 | 123 | 5.0 | 3:3 |
| 3 | 85 | 127 | 5.0 | 3:1 |
| 4 | 94 | 117 | 10.0 | 3:1 |
| 5 | 95 | 124 | 10.0 | 3:1 |
| 6 | 96 | 125 | 10.0 | 3:1 |
| 7 | 97 | 129 | 10.0 | 3:1 |
| 8 | 97 | 129 | 10.0 | 3:1 |
| 9 | 98 | 134 | 10.0 | 3:1 |
| 10 | 100 | 135 | 10.0 | 3:1 |
| 11 | 107 | 137 | 10.0 | 3:1 |
| 12 | 112 | 135 | 11.0 | 3:1 |
| 13 | 112 | 136 | 10.0 | 3:1 |
| 14 | 112 | 137 | 10.0 | 3:1 |
| 16 | 112 | 138 | 10.0 | 3:1 |
| 17 | 118 | 140 | 10.0 | 3:1 |
| 18 | 112 | 141 | 10.0 | 3:1 |
| 19 | 112 | 137 | 9.0 | 3:1 |
| 20 | 112 | 145 | 9.0 | 3:1. |

Fractions 4-9 bulked consist of the mixture of compounds defined according to the structure:

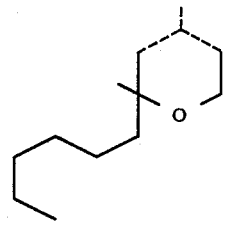

wherein in the mixture in each of the compounds, one of the dashed lines represents a carbon-carbon double bond and each of the other of the dashed lines represent carbon-carbon single bonds.

Fractions 12-19 consist of the compound having the structure:

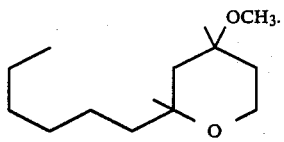

The compound having the structure:

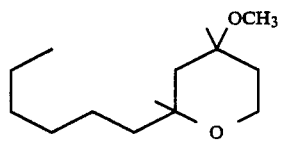

has a green, herbaceous aroma with animalic undertones.

The mixture of compounds having the structure:

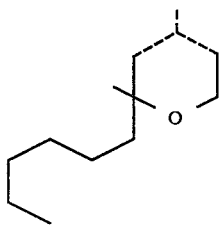

has a fruity, peach, coconut aroma profile with green and fruity topnotes.

EXAMPLE XVI

Preparation of Tetrahydro-4-Methoxy-2,4-Dimethyl-2-Phenyl-2H-Pyran

Reactions:

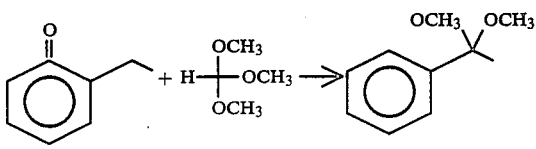

and

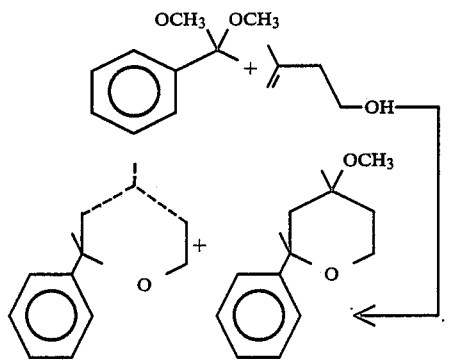

The procedure of Example I is carried with the exception that the following reagents are utilized:

| Reagent | Weight |
|---|---|
| Acetophenone | 464 grams (4 moles) |
| Trimethylorthoformate | 530 grams (5 moles) |
| Methyl Alcohol | 100 grams |
| Sodium Acetate | 8 grams |
| Concentrated Hydrochloric Acid | 5 ml |
| Isoprenol | 344 grams |
| Concentrated Sulfuric Acid | 9 grams |
| 50% Aqueous Sodium Hydroxide | 60 |

After quenching the organic phase is distilled on a 1½"×12" Goodloe column yielding the following fractions:

| Fraction No. | Vapor Temp. (°C.) | Liquid Temp. (°C.) | Vacuum mm/Hg. Pressure | Reflux Ratio |
|---|---|---|---|---|
| 1 | 74/ | 116/ | 5 0 | 3:1 |
| 2 | 93 | 116 | 5.0 | 3:1 |

-continued

| Fraction No. | Vapor Temp. (°C.) | Liquid Temp. (°C.) | Vacuum mm/Hg. Pressure | Reflux Ratio |
|---|---|---|---|---|
| 3 | 93 | 117 | 5.0 | 3:1 |
| 4 | 94 | 118 | 5.0 | 3:1 |
| 5 | 95 | 123 | 5.0 | 3:1 |
| 6 | 97 | 130 | 4.6 | 3:1 |
| 7 | 98 | 135 | 4.6 | 3:1 |
| 8 | 107 | 145 | 4.6 | 3:1 |
| 9 | 108 | 153 | 4.6 | 3:1 |
| 10 | 110 | 170 | 4.8 | 3:1 |
| 11 | 100 | 195 | 4.8 | 100% |
| 12 | 100 | 210 | 4.8 | 100%. |

Fractions 8–11, bulked consist of the compound having the structure:

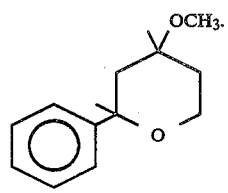

Fractions 2–5 (bulked) consist of the mixture of compounds having the structure:

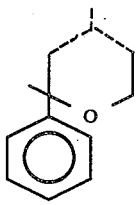

(wherein in the mixture, one of the dashed lines represents a carbon-carbon double bond and each of the other of the dashed lines represent carbon-carbon single bonds).

The mixture of compounds having the structure:

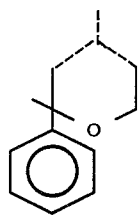

has a herbaceous, green, petitgrain, citrusy aroma profile.

The compound having the structure:

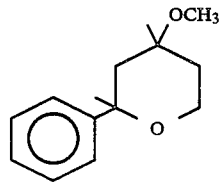

has a new mown hay aroma with green, herbaceous, straw-like undertones.

EXAMPLE XVII

Preparation of
1-Isobutyl-9-Methoxy-9-Methyl-Oxaspiro[4.5]Decane

Reactions:

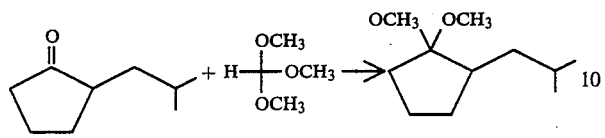

and

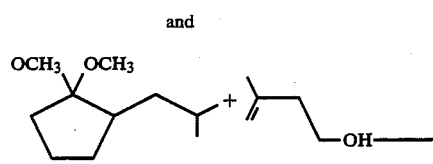

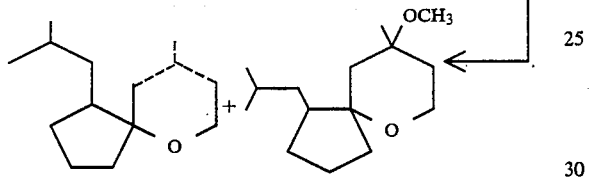

A procedure is carried out similar to that of Example I with the exception that the following reagents are used:

| Reagent | Weight |
| --- | --- |
| 2-Isobutylcyclopentanone | 236 grams |
| Trimethylorthoformate | 223 grams |
| Methyl Alcohol | 50 grams |
| Concentrated Hydrochloric Acid | 2 ml |
| Sodium Acetate | 4 grams |
| Isoprenol | 144 grams |
| Concentrated Sulfuric Acid | 4 grams |
| 50% Aqueous Sodium Hydroxide | 30 grams |

After quenching the organic phase is distilled on a 1½×12″ Goodloe column yielding the following fractions.

| Fraction No. | Vapor Temp. (°C.) | Liquid Temp. (°C.) | Vacuum mm/Hg. Pressure | Reflux Ratio |
| --- | --- | --- | --- | --- |
| 1 | 56/ | 115 | 6.0 | 3:1 |
| 2 | 64 | 115 | 6.0 | 3:1 |
| 3 | 79 | 115 | 4.0 | 3:1 |
| 4 | 84 | 113 | 3.5 | 3:1 |
| 5 | 87 | 119 | 3.5 | 3:1 |
| 6 | 88 | 123 | 3.5 | 3:1 |
| 7 | 93 | 125 | 3.5 | 3:1 |
| 8 | 102 | 128 | 3.5 | 3:1 |
| 9 | 107 | 128 | 3.5 | 3:1 |
| 10 | 108 | 130 | 3.5 | 3:1 |
| 11 | 108 | 144 | 3.5 | 100% |
| 12 | 108 | 158 | 3.5 | 100%. |

Fraction 3 consists of the mixture of compounds having the structure:

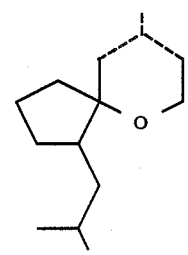

wherein in the mixture, one of the dashed lines represents a carbon-carbon double bond and each of the other of the dashed lines represent carbon-carbon single bonds.

Fractions 8-12 consist of the compound having the structure:

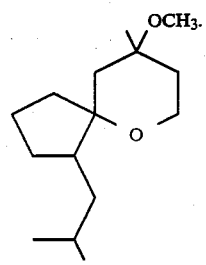

The compound having the structure:

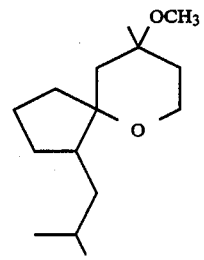

has a jasmine aroma.

The mixture of compounds having the structure:

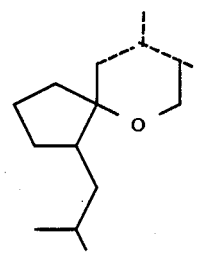

has a green, herbaceous aroma with green, herbaceous undertones.

EXAMPLE XVIII

Preparation of
9-Methoxy-9-Methyl-1-n-Pentyl-Oxaspiro[4.5]Decane

Reactions:

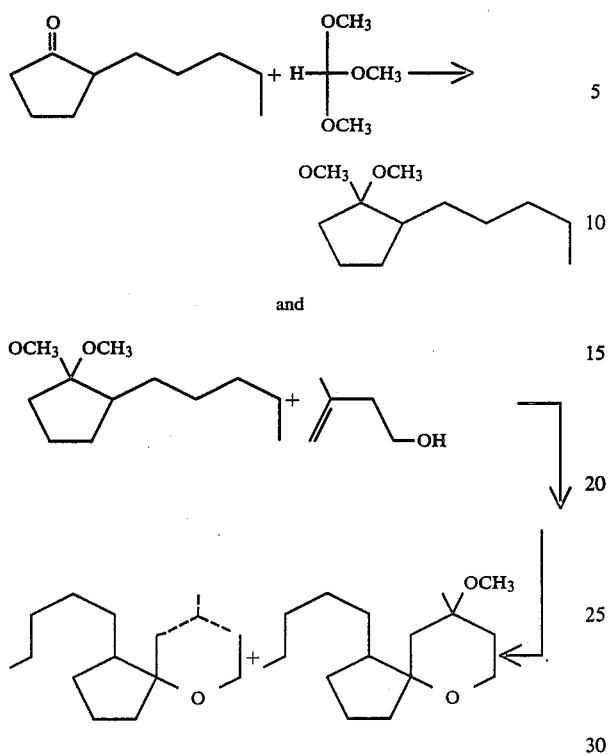

The procedure of Example I is carried out with the exception that the following reagents are utilized:

| Reagent | Weight |
|---|---|
| 2-Pentyl-Cyclopentanone | 238 grams |
| Trimethylorthoformate | 204 grams |
| Methyl Alcohol | 50 grams |
| Concentrated Hydrochloric Acid | 2 ml |
| Sodium Acetate | 4 grams |
| Isoprenol | 132 grams |
| Concentrated Sulfuric Acid | 4 grams |
| 50% Aqueous Sodium Hydroxide | 30 grams |

After quenching the organic phase is distilled on a 1"×12" Goodloe column yielding the following fractions:

| Fraction No. | Vapor Temp. (°C.) | Liquid Temp. (°C.) | Vacuum mm/Hg. Pressure | Reflux Ratio |
|---|---|---|---|---|
| 1 | 62/ | 107/ | 3.0 | 4:1 |
| 2 | 70 | 112 | 4.0 | 3:1 |
| 3 | 68 | 117 | 2.2 | 3:1 |
| 4 | 66 | 126 | 1.6 | 3:1 |
| 5 | 74 | 138 | 3.0 | 3:1 |
| 6 | 94 | 142 | 2.4 | 3:1 |
| 7 | 97 | 144 | 2.0 | 3:1 |
| 8 | 100 | 144 | 2.0 | 3:1 |
| 9 | 108 | 146 | 2.6 | 3:1 |
| 10 | 113 | 156 | 3.4 | 1:1 |
| 11 | 115 | 158 | 3.4 | 1:1 |
| 12 | 132 | 162 | 3.4 | 100% |
| 13 | 124 | 167 | 2.4 | 100% |
| 14 | 124 | 175 | 2.6 | 100%. |

Fractions 5-9 (bulked) consist of the mixture of compounds having the structure:

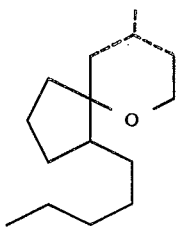

wherein in the mixture in each of the compounds, one of the dashed lines represents a carbon-carbon double bond and each of the other of the dashed lines represent carbon-carbon single bonds.

Fractions 10-14 (bulked) consist of the compound having the structure:

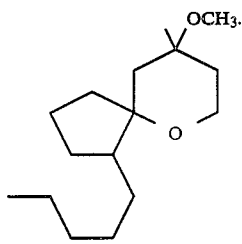

The compound having the structure:

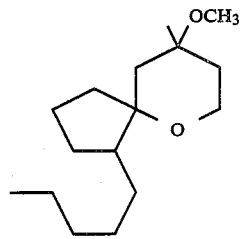

has a fruity, peach-like, apricot and jasmine aroma profile.

The mixture of compounds having the structure:

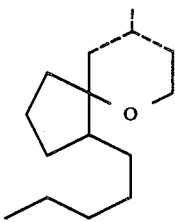

has a fruity, peach, jasmine, cocoa aroma profile with costus oil-like and jasmine topnotes.

EXAMPLE XIX

Preparation of 10-Methoxy-10-Methyl-7-Oxaspiro[5.5]Undecane

Reactions:

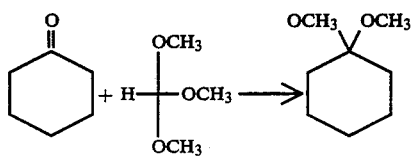

and

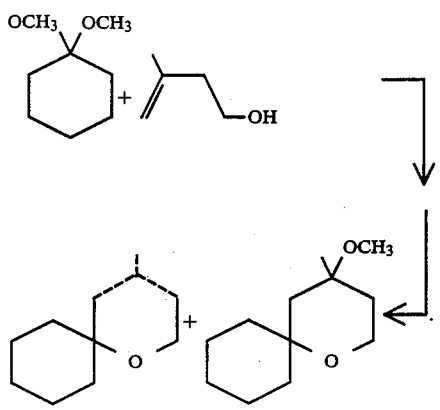

The procedure of Example I is carried out with the exception that the following reagents are used:

| Reagent | Weight |
|---|---|
| Cyclohexanone | 392 grams (4 moles) |
| Trimethylorthoformate | 530 grams (5 moles) |
| Isoprenol | 344 grams (4 moles) |
| Concentrated Hydrochloric Acid | 4 ml |
| Sodium Acetate | 8 grams |
| Concentrated Sulfuric Acid | 8 grams |
| 50% Aqueous Sodium Hydroxide | 60 grams |

After quenching the organic phase is distilled on a 1½×12″ Goodloe column yielding the following fractions:

| Fraction No. | Vapor Temp. (°C.) | Liquid Temp. (°C.) | Vacuum mm/Hg. Pressure | Reflux Ratio |
|---|---|---|---|---|
| 1 | 43/ | 89/ | 8.0 | 3:1 |
| 2 | 73 | 93 | 8.0 | 3:1 |
| 3 | 73 | 95 | 8.0 | 3:1 |
| 4 | 73 | 97 | 8.0 | 3:1 |
| 5 | 79 | 103 | 8.0 | 3:1 |
| 6 | 79 | 105 | 8.0 | 3:1 |
| 7 | 80 | 105 | 8.0 | 3:1 |
| 8 | 84 | 108 | 8.0 | 3:1 |
| 9 | 100 | 109 | 8.0 | 3:1 |
| 10 | 101 | 112 | 8.0 | 3:1 |
| 11 | 103 | 117 | 8.0 | 3:1 |
| 12 | 95 | 116 | 7.0 | 3:1 |
| 13 | 97 | 126 | 7.8 | 3:1 |

Fractions 9-13 (bulked) consist of the compound having the structure:

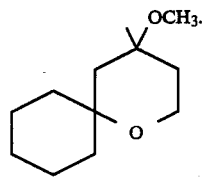

The compound having the structure:

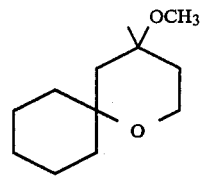

has a woody, citrusy, mandarine orange peel-like, floral, herbaceous and basil aroma profile with sweet, citrus, bergamot and floral undertones.

EXAMPLE XX

Preparation of 3(or 4)-Methyl-9-Tertiarypental-3-Methoxy-1-Oxaspiro[5.-5]Undecan and 3(or 4)-Methyl-9 Tertiarypental-1-Oxaspiro[5.5]-Undec-3-Enes Reactions:

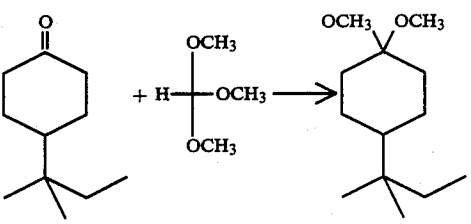

and

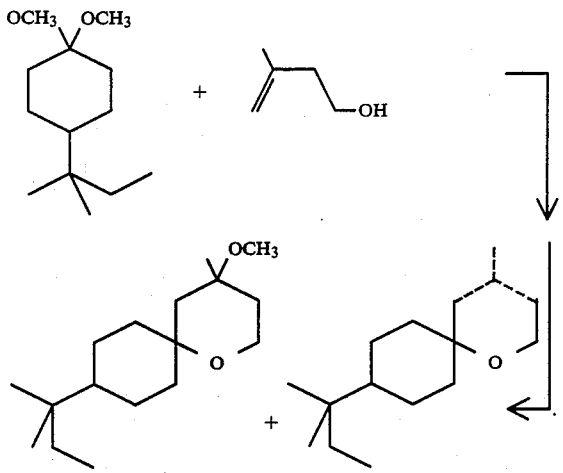

Into a 2 liter reaction vessel is placed the mixture of 300 grams of 4-tertiarypentyl-1-cyclohexanone; 270 ml toluene; and 9 grams of paratoluene sulfonic acid. The reaction mass is brought to reflux and during refluxing over a period of three hours, dropwise, 159 grams of isoprenol is added.

The reaction mass is then stirred at 80° C. for a period of one hour.

The reaction mass is then quenched with 200 ml water followed by 200 ml 10% aqueous sodium hydroxide.

The organic phase is separated from the aqueous phase and the organic phase is fractionally distilled on a 1½×12" Goodloe column yielding the following fractions:

| Fraction No. | Vapor Temp. (°C.) | Liquid Temp. (°C.) | Vacuum mm/Hg. Pressure | Reflux Ratio |
|---|---|---|---|---|
| 1 | 34/ | 53/ | 2.0 | 3:2 |
| 2 | 21 | 95 | 2.0 | 3:2 |
| 3 | 106 | 144 | 3.0 | 3:2 |
| 4 | 122 | 151 | 3.0 | 100% |
| 5 | 122 | 159 | 3.0 | 100% |
| 6 | 122 | 170 | 3.0 | 100% |
| 7 |  | 210 | 3.0 | 100%. |

The compound having the structure:

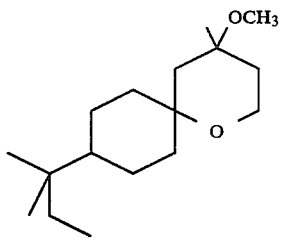

has a herbaceous aroma with fresh, ozoney undertones.

The mixture of compounds having the structure:

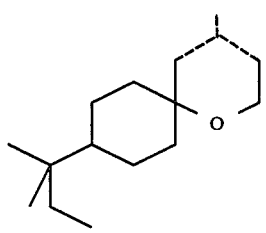

(wherein in the mixture in each of the compounds, one of the dashed lines represents a carbon-carbon double bond and each of the other of the dashed lines represent carbon-carbon single bonds) has a herbaceous, fruity, plum, prune aroma with ozoney and tea-like undertones.

EXAMPLE XXI

The following Chypre formulations are prepared:

| Ingredients | Parts by Weight | | | |
|---|---|---|---|---|
| | XXI(A) | XXI(B) | XXI(C) | XXI(D) |
| Musk ambrette | 40 | 40 | 40 | 40 |
| Musk ketone | 60 | 60 | 60 | 60 |
| Coumarin | 30 | 30 | 30 | 30 |
| Oil of bergamot | 150 | 150 | 150 | 150 |
| Oil of lemon | 100 | 100 | 100 | 100 |
| Methyl ionone | 50 | 50 | 50 | 50 |
| Hexyl cinnamic aldehyde | 100 | 100 | 100 | 100 |
| Hydroxycitronellal | 100 | 100 | 100 | 100 |
| Oil of Lavender | 50 | 50 | 50 | 50 |
| Texas cedarwood oil | 85 | 85 | 85 | 85 |
| Virginia cedarwood oil | 30 | 30 | 30 | 30 |
| Oil of sandalwood (East Indies) | 40 | 40 | 40 | 40 |
| Isoeugenol | 20 | 20 | 20 | 20 |
| Eugenol | 10 | 10 | 10 | 10 |
| Benzyl acetate | 30 | 30 | 30 | 30 |
| α-phenyl ethyl alcohol | 40 | 40 | 40 | 40 |
| β-phenyl ethyl alcohol | 30 | 30 | 30 | 30 |
| Oakmoss absolute | 30 | 30 | 30 | 30 |
| Vetiver oil Venezuela | 25 | 25 | 25 | 25 |
| The compound having the structure: prepared to according to Example I. | 62 | 0 | 0 | 0 |
| The compound having the structure: prepared according to Example II. | 0 | 62 | 0 | 0 |
| The compound having the structure: prepared according to Example III. | 0 | 0 | 62 | 0 |
| The compound having the structure: prepared according to Example IV. | 0 | 0 | 0 | 62 |

The compound having the structure:

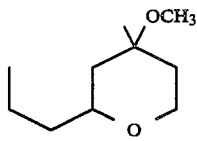

prepared according to Example I imparts to this Chypre formulation an intense and long-lasting green, herbaceous, parsley, rose, fruity, spicy, earthy and rooty undertones. Accordingly, the formulation of Example XXI(A) can be described as "Chypre having a green, herbaceous, parsley, rose, fruity, spicy, earthy and rooty" undertones.

The compound having the structure:

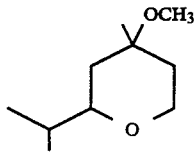

prepared according to Example II imparts to this Chypre formulation, an intense and long-lasting sauge sclaree, minty and woody undertones. Accordingly, the formulation of Example XXI(B) can be described as "Chypre having sauge sclaree, minty and woody" undertones.

The compound having the structure:

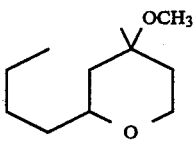

imparts to this Chypre formulation, fruity, herbaceous, celery-like and citrusy topnotes with fruity, floral, jasmine, lily of the valley, green and herbaceous undertones. Accordingly, the perfume formulation of Example XXI(C) can be described as "Chypre having fruity, herbaceous, celery-like and citrusy" topnotes with fruity, floral, jasmine, lily of the valley, green and herbaceous" undertones.

The compound having the structure:

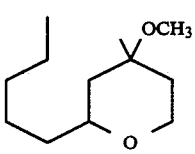

prepared according to Example IV imparts to this Chypre formulation, fresh, clean, tangerine-like, fruity and jasmine undertones with galbanum, jasmine, celery-like, green and pineapple" topnotes. Accordingly, the perfume formulation of Example XXI(D) can be described as "Chypre having fresh, clean, tangerine-like, fruity and jasmine" undertones and galbanum, jasmine, celery-like, green and pineapple" topnotes.

EXAMPLE XXII

Preparation of Cosmetic Powder Compositions

Cosmetic powder compositions are prepared by mixing in a ball mill 100 grams of talcum powder with 0.25 grams of each of the substances set forth in Table III below. Each of the cosmetic powder compositions has an excellent aroma as described in Table III below:

TABLE III

| Substance | Aroma Description |
|---|---|
| The compound having the structure: 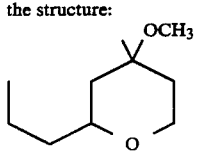 prepared according to Example I. | A green, herbaceous, parsley, rose, fruity, spicy, earthy and rooty aroma profile. |

TABLE III-continued

| Substance | Aroma Description |
|---|---|
| The compound having the structure: 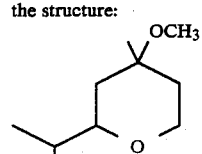 prepared according to Example II. | A sauge sclaree, minty and woody aroma profile. |
| The compound having the structure: 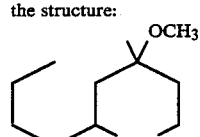 prepared according to Example III. | A fruity, herbaceous, celery-like and citrusy aroma profile with fruity, floral, green, jasmine, lily of the valley, green and herbaceous undertones. |
| The compound having the strucure: 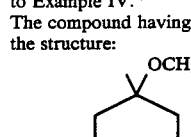 prepared according to Example IV. | A fresh, clean, tangerine-like, fruity, jasmine aroma with galbanum, jasmine, celery-like, green and pineapple topnotes. |
| The compound having the structure: 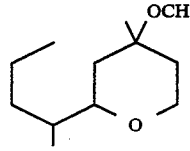 prepared according to Example V. | A green, herbaceous and woody aroma with floral undertones. |
| The compound having the structure: 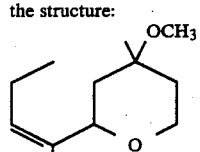 prepared according to Example VI. | A spicy, dill, caraway and herbaceous aroma profile with animalic, dill and caraway undertones. |
| The compound having the structure: 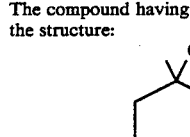 prepared according to Example VII. | A nutty, coconut aroma with cinnamon and pineapple topnotes and floral and herbaceous undertones. |
| The compound having the structure:  prepared according | A spicy aroma with oak moss topnotes. |

TABLE III-continued

| Substance | Aroma Description |
|---|---|
| to Example VIII. | |
| The compound having the structure: 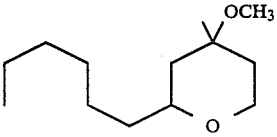 prepared according to Example IX. | A fruity, herbaceous, floral aroma with citrusy, herbaceous and floral undertones. |
| The compound having the structure: 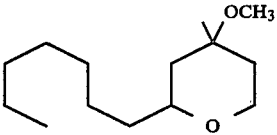 prepared according to Example X. | A fruity, peach, coconut-like aroma with almond oil topnotes. |
| The compound having the structure: 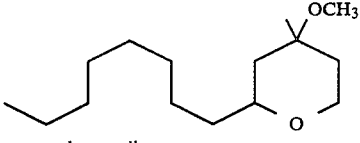 prepared according to Example XI. | A fresh, ozoney, seashore aroma with animalic topnotes. |
| The compound having the structure: 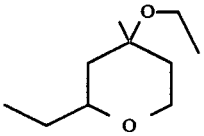 prepared according to Example XII. | A caramel, maple syrup aroma with green, herbaceous topnotes. |
| The compound having the structure: 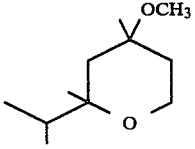 prepared according to Example XIII. | A minty, woody, green and herbaceous aroma profile with camphoraceous, eucalyptus-like topnotes. |
| The compound having the structure: 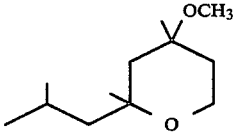 prepared according to Example XIV. | A citrusy, grapefruit, nootkatone-like aroma profile. |
| The compound having the structure: 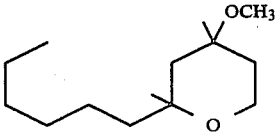 prepared according to Example XV. | A green, herbaceous aroma with animalic undertones. |
| The compound having the structure: | A new mown hay aroma with green, |

TABLE III-continued

| Substance | Aroma Description |
|---|---|
|  prepared according to Example XVI. | herbaceous and straw-like undertones. |
| The compound having the structure: 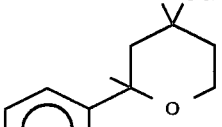 prepared according to Example XVII. | A jasmine aroma. |
| The compound having the structure: 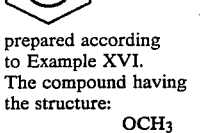 prepared according to Example XVIII. | A fruity, peach-like, apricot and jasmine aroma profile. |
| The compound having the structure: 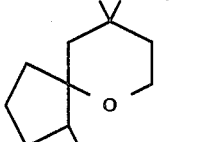 prepared according to Example XIX. | A woody, citrusy, mandarin, orange peel, floral and herbaceous and basil aroma profile with sweet, citrus, bergamot and floral undertones. |
| The compound having the structure: 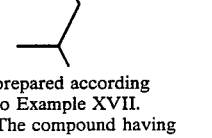 prepared according to Example XX. | A herbaceous, plum aroma with fresh, ozoney undertones. |
| Perfume composition of Example XXI(A). | Chypre having a green, herbaceous, parsley, rose, fruity, spicy, earthy and rooty undertones. |
| Perfume composition of Example XXI(B). | Chypre having sauge sclaree, minty and woody undertones. |
| Perfume composition of Example XXI(C). | Chypre having fruity, herbaceous, |

TABLE III-continued

| Substance | Aroma Description |
|---|---|
|  | celery-like and citrusy topnotes with fruity, floral, jasmine, lily of the valley, green and herbaceous undertones. |
| Perfume composition of Example XXI(D). | Chypre having fresh, clean, tangerine-like, fruity and jasmine undertones and galbanum, jasmine, celery-like, green and pineapple topnotes. |

EXAMPLE XXIII

Perfumed Liquid Detergents

Concentrated liquid detergents (Lysine salt of n-dodecylbenzene sulfonic acid as more specifically described in U.S. Pat. No. 3,948,818 issued on Apr. 6, 1976) with aroma nuances as set forth in Table III of Example XXII are prepared containing 0.10%, 0.15%, 0.20%, 0.25%, 0.30% and 0.35% of the substance set forth in Table III of Example XXII. They are prepared by adding and homogeneously mixing the appropriate quantity of substance set forth in Table III of Example XXII in the liquid detergent. The detergents all possess excellent aromas as set forth in Table III of Example XXII, the intensity increasing with greather concentrations of substance as set forth in Table III of Example XXII.

EXAMPLE XXIV

Preparation of Colognes and Handkerchief Perfumes

Compositions as set forth in Table III of Example XXII are incorporated into colognes at concentrations of 2.0%, 2.5%, 3.0%, 3.5%, 4.0%, 4.5% and 5.0% in 80%, 85%, 90% and 95% aqueous food grade ethanol solutions; and into handkerchief perfumes at concentrations of 15%, 20%, 25% and 30% (in 80%, 85%, 90% and 95% aqueous food grade ethanol solutions). Distinctive and definitive fragrances as set forth in Table III of Example XXII are imparted to the colognes and to the handkerchief perfumes at all levels indicated.

EXAMPLE XXV

Preparation of Soap Compositions

One hundred grams of soap chips [per sample] (IVORY ®, produced by the Procter & Gamble Company of Cincinnati, Ohio), are each mixed with one gram samples of substances as set forth in Table III of Example XXII until homogeneous compositions are obtained. In each of the cases, the homogeneous compositions are heated under 8 atmospheres pressure at 180° C. for a period of three hours and the resulting liquids are placed into soap molds. The resulting soap cakes, on cooling, manifest aromas as set forth in Table III of Example XXII.

EXAMPLE XXVI

Preparation of Solid Detergent Compositions

Detergents are prepared using the following ingredients according to Example I of Canadian Patent No. 1,007,948:

| Ingredient | Percent By Weight |
|---|---|
| "NEODOL ® 45-11" (a $C_{14}$-$C_{15}$ alcohol ethoxylated with 11 moles of ethylene oxide) | 12 |
| Sodium carbonate | 55 |
| Sodium citrate | 20 |
| Sodium sulfate, water brighteners | q.s. |

This detergent is a phosphate-free detergent. Samples of 100 grams each of this detergent are admixed with 0.10, 0.15, 0.20 and 0.25 grams of each of the substances as set forth in Table III of Example XXII. Each of the detergent samples has an excellent aroma as indicated in Table III of Example XXII.

EXAMPLE XXVII

Utilizing the procedure of Example I at column 15 of U.S. Pat. No. 3,632,396, non-woven cloth substrates useful as dry-added fabric softening articles of manufacture are prepared wherein the substrate, the substrate coating and the outer coating and the perfuming material are as follows:
1. A water "dissolvable" paper ("Dissolvo Paper");
2. Adogen 448 (m.p. about 140° F.) as the substrate coating; and
3. An outer coating having the following formulation (m.p. about 150° F.):
   15%-$C_{20-22}$ HAPS
   22%-isopropyl alcohol
   20%-antistatic agent
   1%-of one of the substances as set forth in Table III of Example XXII.

Fabric softening compositions prepared according to Example I at column 15 of U.S. Pat. No. 3,632,396 having aroma characteristics as set forth in Table III of Example XXII, consist of a substrate coating having a weight of about 3 grams per 100 square inches of substrate; a first coating on the substrate coating consisting of about 1.85 grams per 100 square inches of substrate; and an outer coating coated on the first coating consisting of about 1.4 grams per 100 square inches of substrate. One of the substances of Table III of Example XXII is admixed in each case with the outer coating mixture, thereby providing a total aromatized outer coating, the weight ratio to substrate of about 0.5:1 by weight of the substrate. The aroma characteristics are imparted in a pleasant manner to the head space in a dryer on operation thereof in each case using said dryer-added fabric softener non-woven fabrics aand these aroma characteristics are described in Table III of Example XXII.

EXAMPLE XXVIII

Hair Spray Formulations

The following hair spray formulation is prepared by first dissolving PVP/VA E-735 copolymer manufactured by the GAF Corporation of 140 West 51st Street, New York, N.Y., in 91.62 grams of 95% food grade ethanol, 8.0 grams of the polymer is dissolved in the alcohol. The following ingredients are added to the PVP/VA alcoholic solution:

| Ingredients | Weight Percent |
|---|---|
| Dioctyl sebacate | 0.05 |
| Benzyl alcohol | 0.10 |
| Dow Corning 473 fluid (prepared by the Dow Corning Corporation) | 0.10 |
| Tween 20 surfactant (prepared by ICI America Corporation) | 0.03 |
| One of the perfumery substances as set forth in Table III of Example XXII. | 0.10 |

The perfuming substances as set forth in Table III of Example XXII add aroma characteristics as set forth in Table III of Example XXII which are rather intense and aesthetically pleasing to the users of the soft-feel, good-hold pump hair sprays.

EXAMPLE XXIX

Conditioning Shampoos

Monoamid CMA (prepared by the Mona Industries Company) (3.0 weight percent) is melted with 2.0 weight percent coconut fatty acid (prepared by Procter & Gamble Company of Cincinnati, Ohio); 1.0 weight percent ethylene glycol distearate (prepared by the Armak Corporation) and triethanolamine (a product of Union Carbide Corporation) (1.4 weight percent). The resulting melt is admixed with Stepanol WAT produced by the Stepan Chemical Company (35.0 weight percent). The resulting mixture is heated to 60° C. and mixed until a clear solution is obtained (at 60° C.).

GAFQUAT®755N polymer (manufactured by GAF Corporation of 140 West 51st Street, New York, N.Y.) (5.0 weight percent) is admixed with 0.1 weight percent sodium sulfite and 1.4 weight percent polyethylene glycol 6000 distearate produced by Armak Corporation.

The resulting material is then mixed and cooled to 45° C. and 0.3 weight percent of perfuming substance as set forth in Table III of Example XXII is added to the mixture. The resulting mixture is cooled to 40° C. and blending is carried out for an additional one hour in each case. At the end of this blending period, the resulting material has a pleasant fragrance as indicated in Table III of Example XXII.

EXAMPLE XXX

Four drops of each of the substances as set forth in Table III of Example XXII, supra, is added separately to two grams of AROMOX® DMC-W to produce a clear premix. The clear premix is added to 200 grams of CLOROX® with stirring resulting in a clear stable, single phase solution. Sufficient 1M aqueous NaOH is added to bring the pH of the mixture up to 12.8. The solution remains substantially stable at 120° F. for a period of seven days. When the 5% aqueous sodium hypochlorite solution is used as a laundry bleach, the resulting laundry, on dry-out in an atmosphere of 65% relative humidity yields substantially no characteristic "hypochlorite" odor, but does have a faint pleasant aroma as set forth in Table III of Example XXII. Furthermore, no such characteristic "hypochlorite" aroma is retained on the hands of the individual handling such laundry in both the wet and the dry states.

EXAMPLE XXXI

AROMOX® DMMC-W in various quantities is mixed with 0.1 grams of one of the substances set forth in Table III of Example XXII, supra. The resulting premixes are then added to 200 grams of an aqueous 5% sodium hypochlorite solution. Sufficient 12.5M aqueous NaOH is added to bring the pH of the mixture up to 13. The following results are obtained:

| Percentage AROMOX® DMMC-W | Clarity of Hypochlorite Solution after addition of Premix |
|---|---|
| 0.23% | Clear after three days |
| 0.15% | Clear after three days |
| 0.08% | Initially slightly turbid; two phases exist after three days. |

When the 5% aqueous sodium hypochlorite solution is used as a laundry bleach, the resulting laundry on dry-out, in an atmosphere of 65% relative humidity, yields substantially no characteristic "hypochlorite" odor, but does have a faint, pleasant aroma as set forth in Table III of Example XXII. Furthermore, no such characteristic "hypochlorite" aroma is retained on the hands of the individual handling such laundry in both the wet and dry states.

EXAMPLE XXXII

Two grams of AROMOX® DMMC-W is admixed with eight drops of one of the substances set forth in Table III of Example XXII, supra. The premix is then added with stirring to 200 grams of a 7% aqueous solution of lithiumn hypochlorite. Sufficient 3M aqueous LiOH is added to bring the pH of the solution to 13.4. The mixture is then heated to 120° F. and maintained at the temperature with stirring for a period of one week. The resulting solution remains clear in a single phase. When used as a laundry bleach, the resulting bleached laundry, on dry-out in an atmosphere of 50% relative humidity retains a "clean" warm aroma as set forth in Table III of Example XXII, supra; whereas without the use of the substance set forth in Table III of Example XXII, supra, the bleached laundry has a faint characteristic disagreeable "hypochlorite" aroma.

EXAMPLE XXXIII

Two grams of AROMOX® DMMC-W is admixed with eight drops of one of the substances of Table III of Example XXII, supra. This premix is then added, with stirring to 200 grams of a mixture containing 4.5% aqueous sodium hypochlorite. Sufficient 4M aqueous LiOH is added to bring the pH of the solution to 13.4. The mixture is then heated to 120° F. and maintaining at that temperature for a period of one week. The resulting solution remains clear in a single phase. when used as a laundry bleach, the resulting bleached laundry on dry-out in an atmosphere of 50% relative humidity retains a "clean fresh" warm aroma as set forth in Table III of Example XXII, supra; whereas without the use of the substance set forth in Table III of Example XXII, supra, the bleached laundry has a faint characteristic disagreeable "hypochlorite" aroma.

EXAMPLE XXXIV

Two grams of AROMOX ® DMMC-W is admixed with eight drops of one of the substances as set forth in Table III of Example XXII, supra. This premix is then added with stirring to 200 grams of a mixture containing 4.5% aqueous sodium hypochlorite and 4.5% aqueous lithium hypochlorite. Sufficient 2M aqueous NaOH is added to bring the pH of the solution to 13.4. The mixture is then heated to 110° F. and maintained at that temperature with stirring for a period of 2 weeks. The resulting solution remains clear as a single phase when used as a laundry bleach. The resulting laundry bleach, on dry-out in an atmosphere of 50% relative humidity, retains an aroma as set forth in Table III of Example XXII, supra, whereas without the use of the substance set forth in Table III of Example XXII, supra, the bleached laundry has a faint characteristic disagreeable "hypochlorite" aroma.

EXAMPLE XXXV

Four drops of one of the substances set forth in Table III of Example XXII, supra, is added to 1.5 grams of AROMOX ® to produce a clear premix is added to 200 grams of CLOROX ® with stirring resulting in a clear stable single phase solution. Sufficient 1M aqueous NaOH is added to bring the pH of the mixture up to 12.8. The solution remains substantially stable at 120° F. for a period of 7 days. When the 5% aqueous sodium hypochlorite solution is used as a laundry bleach, the resulting laundry on dry-out in an atmosphere of 65% relative humidity yields substantially no characteristic "hypochlorite" odor but does have a faint pleasant warm, long-lasting aroma as set forth in Table III of Example XXII, supra. Furthermore, no such characteristic "hypochlorite" aroma is retained on the hands of the individual handling such laundry in both the wet and dry states.

EXAMPLE XXXVI

Four drops of one of the substances set forth in Table III of Example XXII, supra, is added to 1 gram n-undecyl dimethyl amine oxide to produce a clear premix. The clear premix is added to 200 grams of CLOROX ® with stirring resulting in a clear stable single phase solution. Sufficient 1M aqueous NaOH is added to bring the pH of the mixture up to 12.8. The solution remains substantially stable at 120° F. for a period of 7 days. When the 5% aqueous sodium hypochlorite solution is used as a laundry bleach, the resulting laundry on dry-out in an atmosphere of 65% relative humidity yields substantially no characteristic "hypochlorite" odor but does have a faint pleasant warm aroma as set forth in Table III of Example XXII, supra. Furthermore, no such characteristic "hypochlorite" aroma is retained on the hands of the individual handling such laundry in both the wet and the dry states.

EXAMPLE XXXII

Four drops of one of the substances as set forth in Table III of Example XVII, supra, are added to 1 gram of n-dedecyl dimethyl amine oxide to produce a clear premix. The clear premix is added to 200 grams of CLOROX ® with stirring resulting in a clear, stable single phase solution. Sufficient 1M aqueous NaOH is added to bring the pH of the mixture up to 12.8. The solution remains substantially stable at 120° F. for a period of 7 days. When the 5% aqueous sodium hypochlorite solution is used as a laundry bleach, the resulting laundry on dry-out in an atmosphere of 65% relative humidity yields substantially no characteristic "hypochlorite" aroma, but does have a warm, pleasant, long-lasting aroma as set forth in Table III of Example XVII, supra. Furthermore, no such characteristic "hypochlorite" aroma is retained on the hands of the individual handling such laundry in both the wet and dry states.

EXAMPLE XXXVIII

One gram of n-tridecyl dimethyl amine oxide is admixed with eight drops of one of the substances as set forth in Table III of Example XVII, supra. This premix is then added with stirring to 200 grams of a 7% aqueous solution of lithium hypochlorite. Sufficient 3M aqueous LiOH is added to bring the pH of the solution to 13.4. The mixture is then heated to 120° F. and maintained at that temperature with stirring for a period of one week. The resulting solution remains clear in a single phase. When used as a laundry bleach, the resulting bleached laundry on dry-out in an atmosphere of 50% relative humidity retains a warm, fresh aroma described in Table III of Example XVII, supra, whereas without the use of one of the substances of Table III of Example XVII, supra, the bleached laundry has a faint characteristic disagreeable "hypochlorite" aroma.

EXAMPLE XXXIX

One gram of n-tridecyl dimethyl amine oxide is admixed with eight drops of one of the substances as set forth in Table III of Example XXII, supra. This premix is then added with stirring to 200 grams of a 7% aqueous solution of lithium hypochlorite. Sufficient 3M aqueous LiOH is added to bring the pH of the solution to 13.4. The mixture is then heated to 120° F. and maintained at that temperature with stirring for a period of one week. The resulting solution remains clear in a single phase. When used as a laundry bleach, the resulting bleached laundry on dry-out in an atmosphere of 50% relative humidity retains a warm, fresh aroma described in Table III of Example XXII, supra, whereas without the use of one of the substances of Table III of Example XXII, supra, the bleached laundry has a faint characteristic disagreeable "hypochlorite" aroma.

EXAMPLE XL

AROMOX ® DMMC-W in various quantities is mixed with 0.1 grams of the compound having the structure:

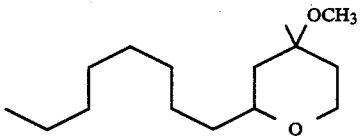

prepared according to Example XI. The resulting premix is then added to 200 grams of an aqueous 5% sodium hypochlorite solution. Sufficient 12.5M aqueous NaOH is added to bring the pH of the mixture up to 13. The following results are obtained:

| Percentage AROMOX ® DMMC-W | Clarity of Hypochlorite Solution After Addition of Premix |
| --- | --- |
| 0.23% | Clear after three days. |
| 0.15% | Clear after three days. |

-continued

| Percentage AROMOX ® DMMC-W | Clarity of Hypochlorite Solution After Addition of Premix |
| --- | --- |
| 0.08% | Initially slightly turbid; two phases exist after three days. |

When the 5% aqueous sodium hypochlorite solutions are used as laundry bleaches, the resulting laundry batches on dry-out in an atmosphere of 65% relative humidity yields substantially no characteristic "hypochlorite" odor, but have fresh, ozoney, seashore aromas. Furthermore, no such characteristics "hypochlorite" aroma is retained on the hands of the individual handling such laundry batches in both the wet and the dry states.

EXAMPLE XLI

Two grams of AROMOX ® DMMC-W are admixed with eight drops of the the compound having the structure:

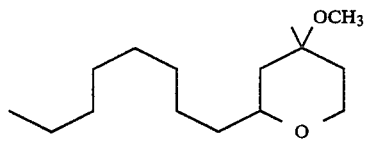

prepared according to Example XI. The premix is then added with stirring to 200 grams of a 7% aqueous solution of lithium hypochlorite. Sufficient 3M aqueous LiOH is added to bring the pH of the solution to 13.4. The mixtures are then heated to 120° F. and maintained at that temperature with stirring for a period of one week. The resulting solution remains clear in a single phase. When used as laundry bleaches, the resulting bleached laundry batches on dry-out in an atmosphere of 50% relative humidity retain a fresh, ozoney, seashore aroma; whereas without the compound having the structure:

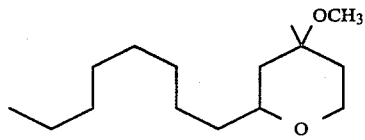

prepared according to Example XI, the bleached laundry batches have a faint characteristic disagreeable "hypochlorite" aroma.

EXAMPLE XLII

Two grams of AROMOX ® DMMC-W are admixed with eight drops of the compound having the structure:

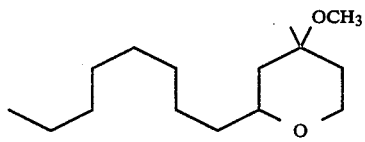

prepared according to Example XI. The premix is then added with stirring to 200 grams of a mixture containing 4.5% aqueous sodium hypochlorite and 4.5% aqueous lithium hypochlorite, Sufficient 4M aqueous LiOH is added to bring the pH of the solution to 13.4. The mixture is then heated to 120° F. and maintained at that temperature for a period of one week. The resulting solution remains clear in a single phase. When used as a laundry bleach, the resulting bleached laundry batches on dry-out in an atmosphere of 50% relative humidity retain a fresh, ozoney, seashore aroma; whereas without the use of the the compound having the structure:

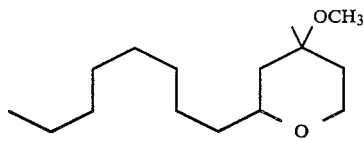

prepared according to Example XI, the bleached laundry dry batches having faint characteristic disagreeable "hypochlorite" aroma.

EXAMPLE XLIII

Two grams of AROMOX ® DMMC-W are admixed with eight drops of either (a) the the compound having the structure:

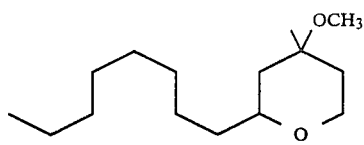

prepared according to Example XI; or (b) a 50-50 mixture of the compound having the structure:

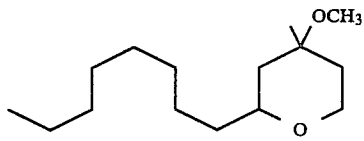

prepared according to Example XI, and diisoamylene epoxide produced according to Example II of application for U.S. Letters Patent, Ser. No. 277,131 filed on June 25, 1981, the disclosure of which is incorporated herein by reference. These premixes are then added with stirring to 200 grams of a mixture containing 4% aqueous sodium hypochlorite and 4% aqueous lithium hypochlorite. Sufficient 2M aqueous NaOH is added to bring the pH of the solutions to 13.4. The mixtures are then heated to 110° F. and maintained at that temperature with stirring for a period of two weeks. The resulting solutions remain clear as a single phase when used as laundry bleaches. The resulting bleached laundry batches on dry-out in an atmosphere of 50% relative humidity retain either a "fresh, ozoney, seashore" aromas (when using the the compound having the structure:

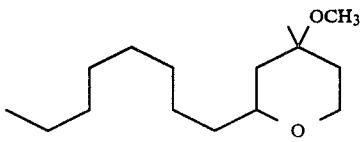

prepared according to Example XI, or retain fresh, ozoney, seashore aromas, when using the mixture of the diisoamylene epoxide and the compound having the structure:

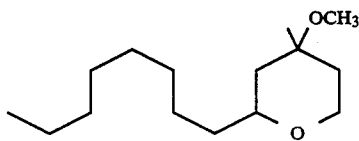

prepared according to Example XI; whereas without the use of the compound having the structure:

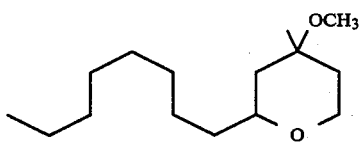

prepared according to Example XI, containing compositions of matter the bleached laundry batches have faint characteristic disagreeable "hypochlorite" aromas.

EXAMPLE XLIV

Four drops of the compound having the structure:

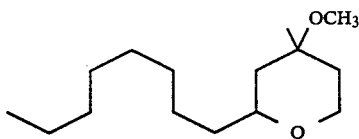

prepared according to Example XI, are added to 1.5 grams of AROMOX® NCMD-W to produce a clear premix. The clear premix is added to 200 grams of CLOROX® with stirring resulting in a clear stable single phase solution. Sufficient 1M aqueous NaOH is added to bring the pH of the mixture up to 12.8. The solution remains substantially stable at 120° F. for a period of seven days. When the 5% aqueous sodium hypochlorite solution is used as a laundry bleach, the resulting laundry on dry-out in an atmosphere of 65% relative humidity yields substantially no characteristic "hypochlorite" odor but does have fresh, ozoney, seashore aromas. Furthermore, no such characteristic "hypochlorite" aroma is retained on the hands of the individual handling such laundry in both the wet and the dry states.

EXAMPLE XLV

Four drops of the compound having the structure:

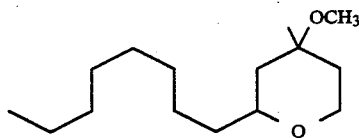

prepared according to Example XI, is added to 1 gram of n-undecyl dimethyl amine oxide to produce a clear premix. The clear premix is added to 200 grams of CLOROX® with stirring resulting in a clear stable single phase solution. Sufficient 1M aqueous NaOH is added to bring the pH of the mixture to 12.8. The solution remains sbstantially stable at 120° F. for a period of seven days. When the 5% aqueous sodium hypochlorite solution is used as a laundry bleach the resulting laundry on dry-out in an atmosphere of 65% relative humidity yields substantially no characteristic "hypochlorite" odor but does have a "fresh, ozoney, seashore" aroma. Furthermore, no such characteristic "hypochlorite" aroma is retained on the hands of the individual handling such laundry in both the wet and the dry states.

EXAMPLE XLVI

One drop of n-tridecyl dimethyl amine oxide is admixed with eight drops of a 50:50 mixture of the diisoamylene epoxide prepared according to Example II of application for U.S. Letters Patent, Ser. No. 277,131 filed on June 25, 1981 and the compound having the structure:

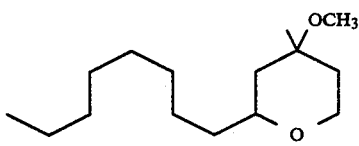

prepared according to Example XI, supra. This premix is then added with stirring to 200 grams of a 7% aqueous solution of lithium hypochlorite. Sufficient 3M aqueous LiOH is added to bring the pH of the solution to 13.4. The mixture is then heated to 120° F. and maintained at that temperature with stirring for a period of one week. The resulting solution remains clear in a single phase. When used as a laundry bleach, the resulting bleached laundry on dry-out in an atmosphere of 50% relative humidity retains a "fresh, ozoney, seashore" aroma; whereas without the use of the mixture of diisoamylene epoxide and the compound having the structure:

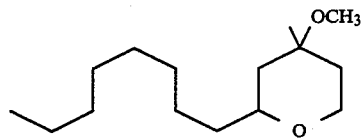

prepared according to Example XI, bleached laundry has a faint characteristic disagreeable "hypochlorite" aroma.

EXAMPLE XLVII

AROMOX® DMMC-W in various quantities is mixed with 0.1 gram of a 25:75 weight:weight mixture of diisoamylene epoxide:

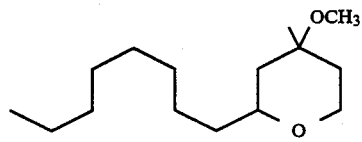

prepared according to Example XI.

The resulting premixes are then added to 200 grams of an aqueous 5% sodium hypochlorite solution. Sufficient 12.5M aqueous NaOH is added to bring the pH of the mixture up to 13. The following results are obtained:

| Percentage AROMOX ®DMMC-W | Clarity of Hypochlorite Solution After Addition of Premix |
| --- | --- |
| 0.23% | Clear after three days. |
| 0.15% | Clear after three days. |
| 0.08% | Initially slightly turbid: two phases exist after three days. |

When used as laundry bleaches, the resulting bleached laundries on dry-out in an atmosphere of 50% relative humidity in each of the three cases above retain a "fresh, ozoney, seashore aroma", whereas without the use of the composition of matter set forth above containing diisoamylene epoxide and the compound having the structure:

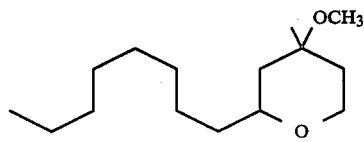

prepared according to Example XI, the bleached laundry has the same characteristic disagreeable "hypochlorite" aroma.

EXAMPLE XLVIII

DOWFAX® 2A1 (see Note 1, infra) in various quantities, as set forth below, is mixed with 0.1 grams of a 50:50 mixture of (a) one of the diisoamylene epoxide compositions prepared according to Example II of application for U.S. Letters Patent, Ser. No. 277,131 filed on June 25, 1981 and (b) the compound having the structure:

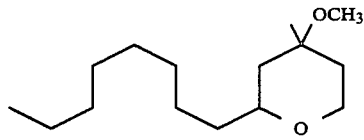

prepared according to Example XI. The resulting premixes are then added to 200 grams of an aqueous 7% sodium hypochlorite solution. Sufficient 12.5M aqueous sodium hydroxide is added to bring the pH of the mixture up to 13.5. The following results are obtained:

| Percentage of DOWFAX ® 2Al | Clarity of Hypochlorite Solution After Addition of Premix |
| --- | --- |
| 0.23% | Clear after seven days. |
| 0.15% | Clear after five days. |
| 0 08% | Clear after three days. |
| 0.01% | Initially slightly turbid: two phases exist after three days. |

EXAMPLE XLIX

Four drops of a 25:75 weight/weight mixture of diisoamylene epoxide prepared according to Example II of application for U.S. Letters Patent, Ser. No. 277,131 and the compound having the structure:

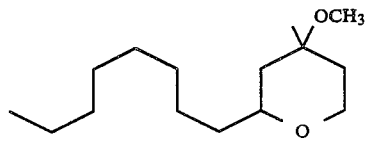

prepared according to Example XI, supra, is added to grams of DOWFAX® 3B2 and 0.5 grams of AROMOX® DMC-W to produce a clear premix. The clear premix is added to 200 grams of CLOROX® with stirring resulting in a clear stable single phase solution. Sufficient 1M aqueous NaOH is added to bring the pH of the mixture of 12.8. The solution remains substantially stable at 120° F. for a period of seven days. When the 5% aqueous sodium hypochlorite solution is used as a laundry bleach, the resulting laundry on dry-out in an atmosphere of 65% relative humidity yields substantially no characteristic "hypochlorite" odor a but does have a fresh, ozoney, seashore aroma. Furthermore, no such characteristic "hypochlorite" aroma is retained on the hands of the individual handling such laundry in both the wet and the dry states.

EXAMPLE L

One gram of DOWFAX® 3B2; one gram of DOWFAX® 2A1 and 0.25 grams of AROMOX® DMMC-W is admixed with eight drops of the compound having the structure:

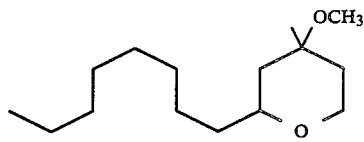

prepared according to Example XI. This premix is then added, with stirring to 200 grams of a mixture containing 4.5% aqueous sodium hypochlorite and 4.5% aqueous lithium hypochlorite. Sufficient 4M aqueous LiOH is added to bring the pH of the solution to 13.4. The mixture is then heated to 120° F. and maintained at that temperature for a period of one week. The resulting solution remains clear in a single pase. When used as a laundry bleach, the resulting bleached laundry on dryout in an atmosphere of 50% relative humidity retains a fresh, ozoney, seashore aroma; whereas without the use of the compound having the structure:

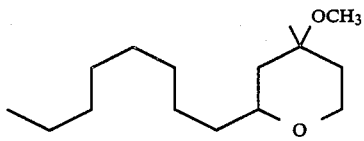

prepared according to Example XI, supra, the bleached laundry has a faint characteristic disagreeable "hypochlorite" aroma.

EXAMPLE LI

One gram of DOWFAX® 2A1 and one gram of DOWFAX® 3B2 is admixed with weight drops of a 50:50 mixture of one of the diisoamylene epoxide compositions of Example II of application for U.S. Letters Patent, Ser. No. 277,131 filed on June 25, 1981 and the compound having the structure:

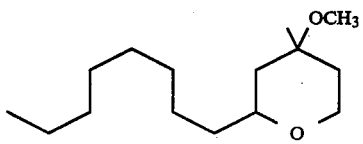

prepared according to Example XI. This premix is then added, with stirring to 200 grams of a mixture containing 4.5% aqueous sodium hypochlorite. Sufficient 4M aqueous LiOH is added to bring the pH of the solution to 13.4. The mixture is then heated to 120° F. and maintained at that temperature for a period of one week. The resulting solution remains clear in a single phase. When used as a laundry bleach, the resulting bleached laundry on dry-out in an atmosphere of 50% relative humidity remains a fresh, ozoney, seashore aroma; whereas without the use of the perfume composition which is a mixture of diisoamylene epoxide and the compound having the structure:

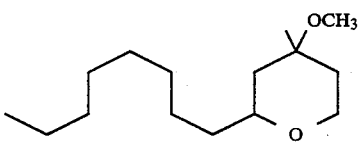

prepared according to Example XI, the bleached laundry has a faint characteristic disagreeable "hypochlorite" aroma.

EXAMPLE LII

Four drops of a 50:50 mixture of one of the diisoamylene epoxide mixtures produced according to Example II of application for U.S. Letters Patent, Ser. No. 277,131 filed on June 25, 1981 and the compound having the structure:

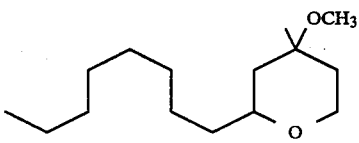

prepared according to Example XI, supra, is added to 1.0 grams of DOWFAX ® 3B2 and 0.25 grams of AROMOX ® NCMD-W to produce a clear premix. The clear premix is added to 200 grams of CLOROX ® resulting in a clear stable single phase solution. Sufficient 1M aqueous NaOH is added to bring the pH of the mixture up to 12.8. The solution remains substantially stable at 120° F. for a period of seven days. When the 5% aqueous sodium hypochlorite solution is used as a laundry bleach, the resulting laundry on dry-out in an atmosphere of 65% relative humidity yields substantially no characteristic "hypochlorite" odor, but does have a fresh, ozoney, seashore aroma. Furthermore, no such characteristic "hypochlorite" aroma is retained on the hands of the individual handling such laundry in both the wet and the dry states.

EXAMPLE LIII

Four drops of the compound having the structure:

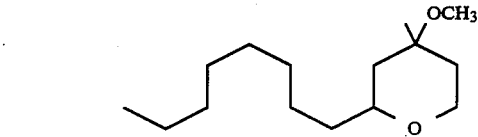

prepared according to Example XI is added to 0.1 grams n-undecyl dimethyl amine oxide and 0.9 grams of DOWFAX ® 3B2 to produce a clear premix. The clear premix is added to 200 grams of CLOROX ® with stirring resulting in a clear single phase solution. Sufficient 1M aqueous NaOH is added to bring the pH of the mixture up to 12.8. The solution remains substantially stable at 120° F. for a period of seven days. When the 5% aqueous sodium hypochlorite solution is used as a laundry bleach, the resulting laundry on dry-out in an atmosphere of 65% relative humidity yields substantially no characteristic "hypochlorite" odor, but does have a fresh, ozoney, seashoe aroma. Furthermore, no such characteristic "hypochlorite" aroma is retained on the hands of the individual handling such laundry in both the wet and the dry states.

EXAMPLE LIV

Four drops of a 50:50 mixture of diisoamylene epoxide produced according to Example II of application for U.S. Letters Patent, Ser. No. 277,131 filed on June 25, 1981 and the compound having the structure:

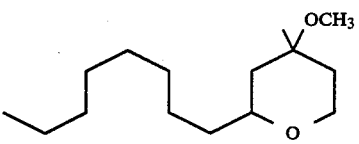

prepared according to Example XI, supra, is added to 0.1 gram of n-dodecyl dimethyl amine oxide and 0.9 grams of DOWFAX ® 2A1 to produce a clear premix. The clear premix is added to 200 grams of CLOROX ® with stirring resulting in a clear stable single phase solution. Sufficient 1M aqueous NaOH is added to bring the pH of the mixture up to 12.8. The solution remains substantially stable at 120° F. for a period of seven days. When the 5% aqueous sodium hypochlorite solution is used as a laundry bleach, the resulting laundry on dry-out in an atmosphere of 65% relative humidity yields substantially no characteristic "hypochlorite" odor but does have fresh, ozoney, seashore aromas. Furthermore, no such characteristic "hypochlorite" aroma is retained on the hands of the individual handling such laundry in both the wet and the dry states.

EXAMPLE LV 0.2 Grams of n-tridecyl dimethyl amine oxide and 0.7 grams of DOWFAX ® 3B2 are admixed with eight drops of the compound having the structure:

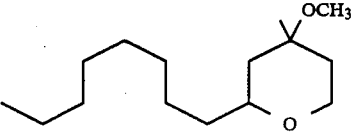

prepared according to Example XI, supra. This premix is then added with stirring to 200 grams of a 7% aqueous solution of lithium hypochlorite. Sufficient 3M aqueous LiOH is added to bring the pH of the solution to 13.4. The mixture is then heated to 120° F. and maintained at that temperature with stirring for a period of one week. The resulting solution remains clear in a single phase. When used as a laundry bleach, the resulting bleached laundry on dry-out in an atmosphere of 50% relative humidity retains a fresh, ozoney, seashore aroma; whereas without the use of the compound having the structure:

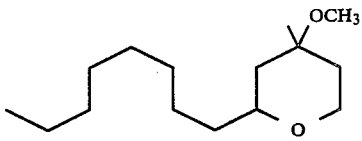

prepared according to Example XI, bleached laundry has a faint characteristic disagreeable "hypochlorite" aroma.

EXAMPLE LVI

A mixture is prepared consisting of 39 grams of DOWFAX® 2A1 (60.75%); 4.5 grams of sodium palmitate (7.00%); and 20.7 grams of water (32.25%). The mixture is heated while stirring followed by ultrasonic dispersion thereby yielding a homogeneous gel. 64.2 Grams of this material is used as follows: 4 drops of the compound having the structure:

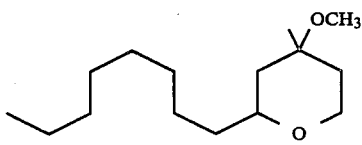

prepared according to Example XI is added to 2.0 grams of the foregoing gel to produce a clear premix. The clear premix is added to 200 grams of CLOROX® with stirring resulting in a clear stable phase solution. Sufficient 1M aqueous NaOH is added to bring the pH of the mixture up to 12.8. The solution remains substantially stable at 120° F. for a period of seven days. When the 5% aqueous sodium hypochlorite solution is used as a laundry bleach, the resulting laundry on dry-out in an atmosphere of 65% relative humidity yields substantially no characteristic "hypochlorite" odor but does have fresh, ozoney, seashore aromas. Furthermore, no such characteristic "hypochlorite" aroma is retained on the hands of the individual handling such laundry in both the wet and the dry states.

EXAMPLE LVII

A mixture is prepared consisting of 39 grams of DOWFAX® 2A1 (60.75); 4.5 grams sodium laurate (7.00%); and 20.7 grams of water (32.25%). The mixture is heated while stirring followed by ultrasonic dispersion thereby yielding a homogeneous gel. 64.2 Grams of this material is used as follows: 4 drops of (a) one of the diisoamylene epoxide mixtures produced according to Example II of application for U.S. Letters Patent, Ser. No. 277,131 filed on June 25, 1981 and (b) the compound having the structure:

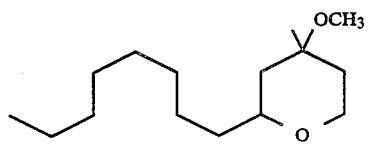

prepared according to Example XI, supra, is added to 2.0 grams of the foregoing gel to produce a clear premix. The clear premix is added to 200 grams of CLOROX® with stirring resulting in a clear stable single phase solution. Sufficient 1M aqueous NaOH is added to bring the pH of the mixture up to 12.8. The solution remains substantially stable at 120° F. for a period of seven days. When the 5% aqueous sodium hypochlorite solution is used as a laundry bleach, the resulting laundry on dry-out in an atmosphere of 65% relative humidity yields substantially no characteristic "hypochlorite" odor but does have fresh, ozoney, seashore aromas. Furthermore, no such characteristic "hypochlorite" aroma is retained on the hands of the individual handling such laundry in both the wet and the dry states.

EXAMPLE LVIII

A mixture is prepared consisting of 20.1 grams DOWFAX®2A1 (60.75%); 2.0 grams of sodium palmitate (7.00%); and 20.0 grams of water (32.25%). The mixture is heated while stirring followed by ultrasonic dispersion thereby yielding a homogeneous gel. 64.2 Grams of this material is used as follows: 4 drops of the compound having the structure:

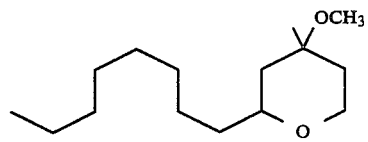

prepared according to Example XI, supra, is added to 2.0 grams of the foregoing gel to produce a clear premix. The clear premix is added to 200 grams of CLOROX® with stirring resulting in a clear stable single phase solution. Sufficient 1M aqueous NaOH is added to bring the pH of the mixture up to 12.8. The solution remains substantially stable at 120° F. for a period of seven days. When the 5% aqueous medium hypochlorite solution is used as a laundry bleach, the resulting laundry on dry-out is an atmosphere of 65% relative humidity yields substantially no characteristic "hypochlorite" odor but does have fresh, ozoney, seashore aromas. Furthermore, no such characteristic "hypochlorite" aroma is retained on the hands of the individual handling such laundry in both the wet and the dry states.

EXAMPLE LIX

A mixture is prepared consisting of 10 grams of DOWFAX®2A1 and 10 grams of DOWFAX®3B1 (60.75); and 2.0 grams of sodium laurate (7.00%); and 20.0 grams of water (32.25%). The mixture is heated while stirring followed by ultrasonic dispersion thereby yielding a homogeneous gel. 64.2 Grams of this material is used as follows: 4 drops of the compound having the structure:

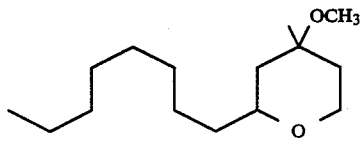

prepared according to Example XI, supra, is added to 2.0 grams of the foregoing gel to produce a clear premix. The clear premix is added to 200 grams of CLOROX ® with stirring resulting in a clear stable single phase solution. Sufficient 1M aqueous NaOH is added to bring the pH of the mixture up to 12.8. The solution remains substantially stable at 120° F. for a period of seven days. When the 5% aqueous sodium hypochlorite solution is used as a laundry bleach, the resulting laundry on dry-out is an atmosphere of 65% relative humidity yields substantially no characteristic "hypochlorite" odor but does have a fresh, ozoney, seashore aroma. Furthermore, no such characteristic "hypochlorite" aroma is retained on the hands of the individual handling such laundry in both the wet and the day states.

EXAMPLE LX

A mixture is prepared consisting of 60 grams of AROMOX ® DMMC-W, 30 grams DOWFAX ® 2A1; 6.0 grams lauric acid; 9.0 grams KOH; and 500 grams water. The mixture is heated while stirring followed by ultrasonic dispersion thereby yielding a homogeneous gel. 64.2 Grams of this material is used as follows: 4 drops of the compound having the structure:

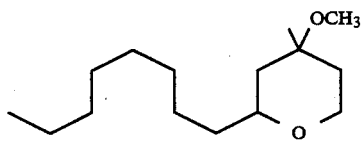

prepared according to Example XI, is added to 2.0 grams of the foregoing gel to produce a clear premix. The clear premix is added to 200 grams of CLOROX ® with stirring resulting in a clear stable single phase solution. Sufficient 1M aqueous NaOH is added to bring the pH of the mixture up to 12.8. The solution remains substantially stable at 120° F. for a period of seven days. When the 5% aqueous sodium hypochlorite solution is used as a laundry bleach, the resulting laundry on dry-out in an atmosphere of 65% relative humidity yields substantially no characteristic "hypochlorite" odor but does have a fresh, ozoney, seashore aromas. Furthermore, no such characteristic "hypochlorite" aroma is retained on the hands of the individual handling such laundry in both the wet and the dry states.

It is noteworthy that the viscosity of the solution subsequent to heating is 26.75 centiposies.

EXAMPLE LXI

A mixture is prepared consisting of 60 grams of AROMOX ® DMMC-W, 21 grams of DOWFAX ® 2A1; 3.6 grams of lauric acid; 10.5 grams of KOH and 508 grams of water. The mixture is heated while stirring followed by ultrasonic dispersion thereby yielding a homogeneous gel having a viscosity of 23.45 centipoises. 64.2 Grams of this material is used as follows: 4 drops of a 50:50 mixture of (a) one of the diisoamylene epoxide mixtures produced according to Example II of application for U.S. Letters Patent, Ser. No. 277,131 filed on June 25, 1981 and (b) the compound having the structure:

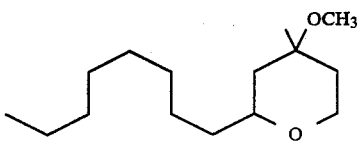

prepared according to Example XI, supra, is added to 2.0 grams of the foregoing gel to produce a clear premix. The clear premix is added to 200 grams of CLOROX ® with stirring resulting in a clear stable single phase solution. Sufficient 1M aqueous NaOH is added to bring the pH of the mixture up to 12.8. The solution remains substantially stable at 120° F. for a period of seven days. When the 5% aqueous sodium hypochlorite solution is used as a laundry bleach, the resulting laundry on dry-out in an atmosphere of 65% relative humidity yields substantially no characteristic "hypochlorite" odor but does have fresh, ozoney, seashore aromas. Furthermore, no such characteristic "hypochlorite" aroma is retained on the hands of the individual handling such laundry in both the wet and the dry states.

What is claimed is:

1. At least one 2,4-disubstituted or 2,2,4-trisubstituted tetrahydropyranyl-pyranyl-4-ether defined according to the structure:

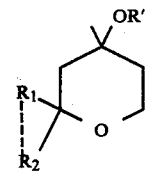

wherein R' is selected from the group consisting of methyl and ethyl and $R_1$ and $R_2$ taken alone are the same or different hydrogen, phenyl, $C_1$–$C_8$ alkyl or $C_2$–$C_8$ alkenyl, with the proviso that $R_1$ and $R_2$ are not both hydrogen, and $R_1$ and $R_2$ taken together represent a $C_5$–$C_{12}$ cycloalkyl or alkyl cycloalkyl moiety.

2. A mixture of compounds comprising at least one compound defined according to claim 1 and a compound having the structure:

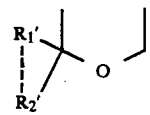

wherein $R_1'$ and $R_2'$ taken alone are the same or different hydrogen, phenyl, $C_1$–$C_8$ alkyl or $C_2$–$C_8$ alkenyl, with the proviso that $R_1$ and $R_2$ are not both hydrogen and $R_1$ and $R_2$ taken together represent a $C_5$–$C_{12}$ cycloalkyl or alkyl cycloalkyl moiety, and wherein the moiety:

is indicative of a mixture of compounds wherein in the mixture one of the dashed lines in the moiety:

is a carbon-carbon double bond and each of the other two of the dashed lines represent carbon-carbon single bonds.

3. A compound of claim 1 having the structure:

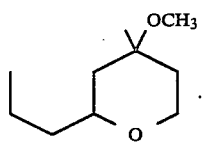

4. A compound of claim 1 having the structure:

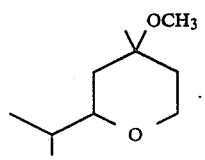

5. A compound of claim 1 having the structure:

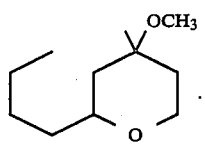

6. A compound of claim 1 having the structure:

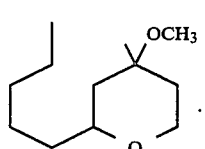

7. A compound of claim 1 having the structure:

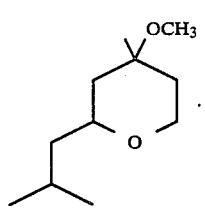

8. A compound of claim 1 having the structure:

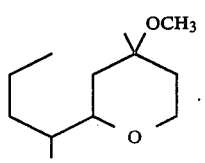

9. A compound of claim 1 having the structure:

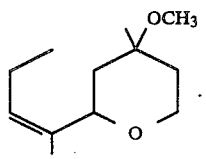

10. A compound of claim 1 having the structure:

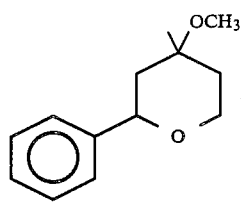

11. A compound of claim 1 having the structure:

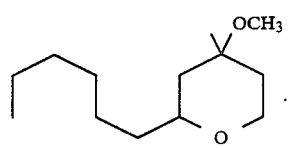

12. A compound of claim 1 having the structure:

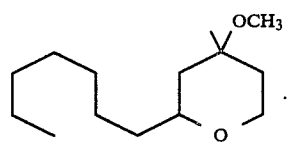

13. A compound of claim 1 having the structure:

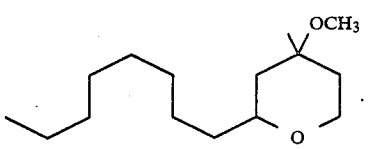

14. A compound of claim 1 having the structure:

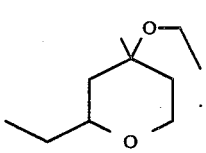

15. A compound of claim 1 having the structure:

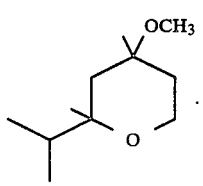

16. A compound of claim 1 having the structure:

17. A compound of claim 1 having the structure:

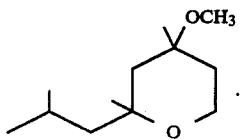

18. A compound of claim 1 having the structure:

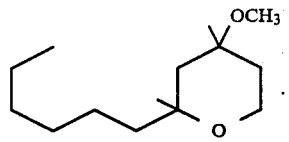

19. A compound of claim 1 having the structure:

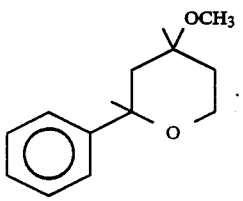

20. A compound of claim 1 having the structure:

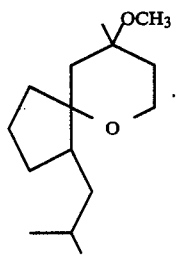

21. A compound of claim 1 having the structure:

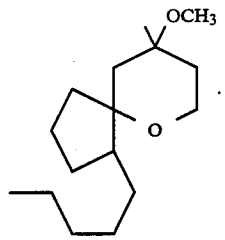

22. A compound of claim 1 having the structure:

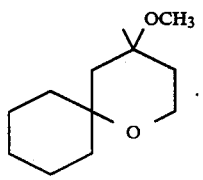

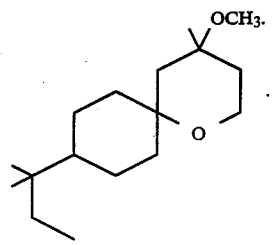

23. A process for augmenting or enhancing the aroma of a consumable material selected from the group consisting of perfume compositions, perfumed articles and perfumed polymers comprising the step of intimately admixing with said consumable material, an aroma augmenting or enhancing quantity of at least one compound defined according to claim 1.

24. A process for augmenting or enhancing the aroma of a consumable material selected from the group consisting of perfume compositions, perfumed articles and perfumed polymers comprising the step of intimately admixing with said consumable material, an aroma augmenting or enhancing quantity of at least one composition of matter defined according to claim 2.

25. A process for augmenting or enhancing the aroma of a consumable material selected from the group consisting of perfume compositions, perfumed articles and perfumed polymers comprising the step of intimately admixing with said consumable material, an aroma augmenting or enhancing quantity of at least one compound defined according to claim 3.

26. A process for agumenting or enhancing the aroma of a consumable material selectedfrom the group consisting of perfume compositions, perfumed articles and perfumed polymers comprising the step of intimately admixing with said consumable material, an aroma augmenting or enhancing quantity of at least one compound defined according to claim 4.

27. A process for augmenting or enhancing the aroma of a consumable material selected from the group consisting of perfume compositions, perfumed articles and perfumed polymers comprising the steps of intimately admixing with said consumable material, an aroma augmenting or enhancing quantity of at least one compound defined according to claim 5.

28. A process for augmenting or enhancing the aroma of a consumable material selected from the group consisting of perfume compositions, perfumed articles and perfumed polymers comprising the step of intimately admixing with said consumable material, an aroma augmenting or enhancing quantity of at least one compound defined according to claim 6.

29. A process for augmenting or enhancing the aroma of a consumable material selected from the group consisting of perfume compositions, perfumed articles and perfumed polymers comprising the step of intimately admixing with said consumable material, an aroma augmenting or enhancing quantity of at least one compound defined according to claim 7.

30. A process for augmenting or enhancing the aroma of a consumable material selected from the group consisting of perfume compositions, perfumed articles and perfumed polymers comprising the step of intimately admixing with said consumable material, an aroma augmenting or enhancing quantity of at least one compound defined according to claim 8.

31. A process for augmenting or enhancing the aroma of a consumable material selected from the group consisting of perfume compositions, perfumed articles and perfumed polymers comprising the step of intimtely admixing with said consumable material, an aroma augmenting or enhancing quantity of at least one compound defined according to claim 9.

32. A process for augmenting or enhancing the aroma of a consumable material selected from the group consisting of perfume compositions, perfumed articles and perfumed polymers comprising the step of intimately admixing with said consumable material, an aroma augmenting or enhancing quantity of at least one compound defined according to claim 10.

33. A process for augmenting or enhancing the aroma of a consumable material selected from the group consisting of perfume compositions, perfumed articles and perfumed polymers comprising the step of intimately admixing with said consumable material, an aroma augmenting or enhancing quantity of at least one compound defined according to claim 11.

34. A process for augmenting or enhancing the aroma of a consumable material selected from the group consisting of perfume compositions, perfumed articles and perfumed polymers comprising the step of intimately admixing with said consumable material, an aroma augmenting or enhancing quantity of at least one compound defined according to claim 12.

35. A process for augmenting or enhancing the aroma of a consumable material selected from the group consisting of perfume compositions, perfumed articles and perfumed polymers comprising the step of intimately admixing with said consumable material, an aroma augmenting or enhancing quantity of at least one compound defined according to claim 13.

36. A process for augmenting or enhancing the aroma of a consumable material selected from the group consisting of perfume compositions, perfumed articles and perfumed polymers comprising the step of intimately admixing with said consumable material, an aroma augmenting or enhancing quantity of at least one compound defined according to claim 14.

37. A process for augmenting or enhancing the aroma of a consumable material selected from the group consisting of perfume compositions, perfumed articles and perfumed polymers comprising the step of intimately admixing with said consumable material, an aroma augmenting or enhancing quantity of at least one compound defined according to claim 15.

38. A process for augmenting or enhancing the aroma of a consumable material selected from the group consisting of perfume compositions, perfumed articles and perfumed polymers comprising the step of intimately admixing with said consumable material, an aroma augmenting or enhancing quantity of at least one compound defined according to claim 16.

39. A process for augmenting or enhancing the aroma of a consumable material selected from the group consisting of perfume compositions, perfumed articles and perfumed polymers comprising the step of intimately admixing with said consumable material, an aroma augmenting or enhancing quantity of at least one compound defined according to claim 17.

40. A process for augmenting or enhancing the aroma of a consumable material selected from the group consisting of perfume compositions, perfumed articles and perfumed polymers comprising the step of intimtely admixing with said consumable material, an aroma augmenting or enhancing quantity of at least one compound defined according to claim 18.

41. A process for augmenting or enhancing the aroma of a consumable material selected from the group consisting of perfume compositions, perfumed articles and perfumed polymers comprising the step of intimately admixing with said consumable material, an aroma augmenting or enhancing quantity of at least one compound defined according to claim 19.

42. A process for augmenting or enhancing the aroma of a consumable material selected from the group consisting of perfume compositions, perfumed articles and perfumed polymers comprising the step of intimately admixing with said consumable material, an aroma augmenting or enhancing quantity of at least one compound defined according to claim 20.

43. A process for augmenting or enhancing the aroma of a consumable material selected from the group consisting of perfume compositions, perfumed articles and perfumed polymers comprising the step of intimately admixing with said consumable material, an aroma augmenting or enhancing quantity of at least one compound defined according to claim 21.

44. A process for augmenting or enhancing the aroma of a consumable material selected from the group consisting of perfume compositions, perfumed articles and perfumed polymers comprising the step of intimately admixing with said consumable material, an aroma augmenting or enhancing quantity of at least one compound defined according to claim 22.

45. A chlorine-containing bleach composition comprising:
   (a) a chlorine bleach base; and
   (b) intimately admixed therewith at least one compound defined according to claim 1.

46. A perfumed aqueous alkali metal hypochlorite solution comprising as a sole detergent a composition of matter selected from the group consisting of (1) at least one substance defined according to the structure:

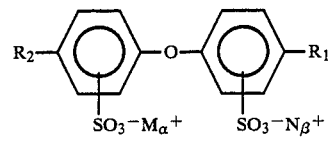

wherein at least one of $R_1$ and $R_2$ is $C_{10}$–$C_{12}$ straight chain or branched chain alkyl; when one of $R_1$ or $R_2$ is $C_{10}$–$C_{12}$ straight chain or branched chain alkyl and the other of $R_1$ or $R_2$ is hydrogen; wherein $M_\alpha$ and $M_\beta$ are the same or different and each represents alkali metal selected from the group consisting of sodium, potassium and lithium and (2) a mixture comprising a material having the structure:

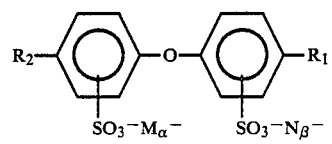

and intimately admixed therewith a substance having the structure:

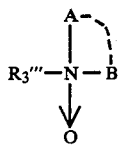

wherein $R_3'''$ is straight chain alkyl; wherein more than 55% of the $R_3'''$ moieties consist of straight chain alkyl having from 11 up to 13 carbon atoms and wherein "A" and "B" are each separately methyl up to 0.2% of one or more compatible perfume oils, such hypochlorite solution having a pH of 11 up to 14.0 and an aroma augmenting or enhancing quantity of at least one compound defined according to claim 1.

47. The composition of matter of claim 46 which is thickened using a thickening quantity of $C_{10}$ alkanoic acid salt thickener in a concentration such that the viscosity of the composition is 20–60 centipoises at a temperature of 20°–40° C.

48. The composition of claim 46 wherein the compound having the structure:

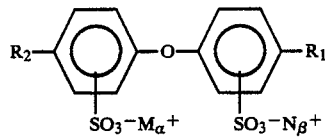

is selected from the group of materials having the structures:

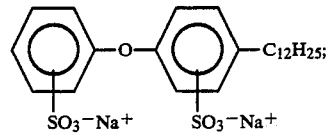

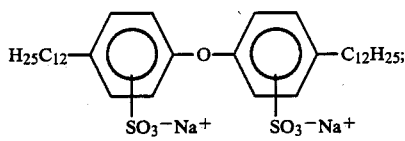

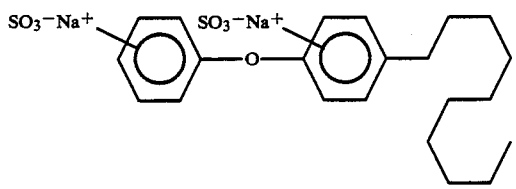

and

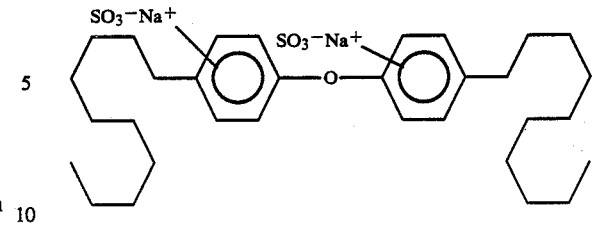

49. A process for producing a stable single phase aqueous alkaline metal hypochlorite solution having a pleasant fragrance consisting, in sequential order, of the steps of (a) adjusting the pH of an aqueous alkali metal hypochlorite solution to the range of 11–14.0; (b) admixing a composition of matter selected from the group consisting of: (i) a chemical compound having the structure:

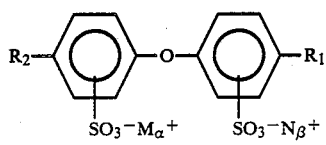

wherein at least one of $R_1$ and $R_2$ is $C_{10}$–$C_{12}$ straight chain or branched chain alkyl and $M_\alpha$ and $M_\beta$ are the same or different and each represents lithium, potassium or sodium; and (ii) a mixture of at least one compound having the structure:

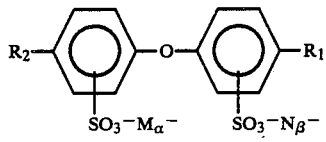

and a compound having the structure:

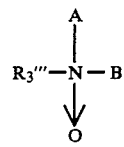

wherein $R_3'''$ is straight chain alkyl; wherein more than 55% of the $R_3'''$ moieties consist of straight chain alkyl having from 11 to 13 carbon atoms and wherein "A" and "B" are each separately methyl or taken together complete a morpholine ring with at least one compound defined according to claim 1 and (c) adding said premix to the pH adjusted hypochlorite solution.

50. The process of claim 49 wherein the perfuming material in addition to being at least one compound defined according to claim 1 also includes diisoamylene epoxide.

* * * * *